(12) United States Patent
Hellerstein

(10) Patent No.: US 7,262,020 B2
(45) Date of Patent: *Aug. 28, 2007

(54) METHODS FOR COMPARING RELATIVE FLUX RATES OF TWO OR MORE BIOLOGICAL MOLECULES IN VIVO THROUGH A SINGLE PROTOCOL

(75) Inventor: Marc K. Hellerstein, Kensington, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 10/872,280

(22) Filed: Jun. 17, 2004

(65) Prior Publication Data

US 2005/0019251 A1    Jan. 27, 2005

Related U.S. Application Data

(60) Provisional application No. 60/484,626, filed on Jul. 3, 2003.

(51) Int. Cl.
*C12Q 1/02* (2006.01)
(52) U.S. Cl. ................. 435/29; 435/4; 435/6
(58) Field of Classification Search ............ 435/4, 435/6, 29; 424/1.81; 536/17.4, 23.1, 24.5
See application file for complete search history.

(56) References Cited

U.S. PATENT DOCUMENTS

| | | | |
|---|---|---|---|
| 4,065,552 A | 12/1977 | Costa | |
| 4,332,784 A | 6/1982 | Smith et al. | |
| 4,889,126 A | 12/1989 | Doddrell et al. | |
| 4,940,658 A | 7/1990 | Allen et al. | |
| 5,042,488 A | 8/1991 | Ackerman | |
| 5,167,948 A | 12/1992 | Wenzel | |
| 5,209,919 A | 5/1993 | Turteltaub et al. | |
| 5,317,098 A | 5/1994 | Shizuya et al. | |
| 5,338,686 A * | 8/1994 | Hellerstein | 436/173 |
| 5,354,662 A | 10/1994 | Stone et al. | |
| 5,376,355 A | 12/1994 | Turteltaub et al. | |
| 5,394,236 A | 2/1995 | Murnick | |
| 5,439,803 A | 8/1995 | Ross et al. | |
| 5,506,147 A | 4/1996 | Kolhouse et al. | |
| 5,597,548 A | 1/1997 | Sherry et al. | |
| 5,783,445 A | 7/1998 | Murnick | |
| 5,910,403 A * | 6/1999 | Hellerstein | 435/4 |
| 5,961,470 A | 10/1999 | Wagner et al. | |
| 6,010,846 A * | 1/2000 | Hellerstein | 435/4 |
| 6,071,245 A | 6/2000 | Kohno et al. | |
| 6,329,208 B1 | 12/2001 | Jones et al. | |
| 6,461,806 B1 * | 10/2002 | Hellerstein | 435/4 |
| 6,461,870 B2 | 10/2002 | Yatscoff et al. | |
| 6,468,802 B1 | 10/2002 | Yatscoff et al. | |
| 6,599,750 B2 | 7/2003 | Yatscoff et al. | |
| 6,602,715 B2 | 8/2003 | Yatscoff et al. | |
| 6,610,270 B1 | 8/2003 | Ajami | |
| 6,625,547 B1 | 9/2003 | Korzekwa et al. | |
| 6,653,090 B1 | 11/2003 | Lopaschuk | |
| 6,764,817 B1 | 7/2004 | Schneider | |
| 6,783,751 B2 | 8/2004 | Heumann | |
| 6,808,875 B2 * | 10/2004 | Hellerstein | 435/4 |
| 6,872,575 B2 | 3/2005 | Regnier | |
| 6,887,712 B1 | 5/2005 | Medford et al. | |
| 2003/0068634 A1 | 4/2003 | Hellerstein | |
| 2003/0133871 A1 * | 7/2003 | Hellerstein | 424/1.11 |
| 2003/0148533 A1 | 8/2003 | Malloy et al. | |
| 2003/0180710 A1 | 9/2003 | Lee et al. | |
| 2003/0180800 A1 | 9/2003 | Lee et al. | |
| 2003/0224420 A1 * | 12/2003 | Hellerstein et al. | 435/6 |
| 2003/0228259 A1 * | 12/2003 | Hellerstein | 424/9.1 |
| 2004/0081994 A1 * | 4/2004 | Hellerstein | 435/6 |
| 2004/0091943 A1 | 5/2004 | Schneider | |
| 2004/0115131 A1 * | 6/2004 | Hellerstein | 424/1.73 |
| 2004/0152994 A1 | 8/2004 | Meier-Augenstein | |
| 2004/0253647 A1 | 12/2004 | Mathews et al. | |
| 2005/0003375 A1 | 1/2005 | Franza et al. | |
| 2005/0019251 A1 | 1/2005 | Hellerstein | |
| 2005/0053992 A1 * | 3/2005 | Hellerstein | 435/6 |
| 2006/0008796 A1 | 1/2006 | Hellerstein | |
| 2006/0029549 A1 | 2/2006 | Hellerstein | |
| 2006/0257576 A1 | 11/2006 | Hellerstein | |
| 2006/0280882 A1 | 12/2006 | Hellerstein | |

FOREIGN PATENT DOCUMENTS

| | | |
|---|---|---|
| EP | 086377 | 11/2002 |
| WO | WO-90/11371 | 10/1990 |
| WO | 93/20800 | 10/1993 |
| WO | WO-93/25705 | 12/1993 |
| WO | 95/13096 | 5/1995 |

(Continued)

OTHER PUBLICATIONS

Hsieh, E. Dynamics of Keratinocytes in Vivo Using 2H20 Labeling. J Invest Dermatol 123(3)530-536, 2004.*
Neese R. Measurement in Vivo of Proliferation Rates of Slow Turnover Cells . . . PNAS 99(24)15345-15350, 2002.*
Hellerstein M. Mass Isotopomer Distribution Analysis at Eight Years. Am J Physiol 276 E1146-1170, 1999.*

(Continued)

*Primary Examiner*—Ralph Gitomer
(74) *Attorney, Agent, or Firm*—Morrison & Foerster LLP

(57) ABSTRACT

The invention relates to techniques for measuring and comparing relative molecular flux rates of different biological molecules by administering isotope-labeled water to one or more tissues or individuals and comparing the molecular flux rates of two or more biological molecules, including biological molecules in different chemical classes. The methods find use in several applications including diagnosing, prognosing, or monitoring a disease, disorder, or condition, the in vivo high-throughput screening of chemical entities and biological factors for therapeutic effects in various disease models, and the in vivo high-throughput screening of chemical entities and biological factors for toxic effects.

41 Claims, 19 Drawing Sheets

FOREIGN PATENT DOCUMENTS

| | | |
|---|---|---|
| WO | WO98/51820 | 11/1998 |
| WO | 00/13025 | 3/2000 |
| WO | 00/63683 | 10/2000 |
| WO | 01/84143 | 11/2001 |
| WO | WO-03/061479 A1 | 7/2003 |
| WO | WO-03/068919 A2 | 8/2003 |
| WO | WO-03/087314 A2 | 10/2003 |
| WO | WO-04/003493 A2 | 1/2004 |
| WO | WO-04/011426 A2 | 2/2004 |
| WO | WO-04/021863 A2 | 3/2004 |
| WO | WO-04/024941 A2 | 3/2004 |
| WO | WO-04/025270 A2 | 3/2004 |
| WO | WO-04/042360 A2 | 5/2004 |
| WO | WO-05/009597 A2 | 2/2005 |
| WO | WO-05/015155 A2 | 2/2005 |
| WO | WO-05/033652 A2 | 4/2005 |

OTHER PUBLICATIONS

Collins M. Measurement of Mitochondrial DNA Synthesis in vivo Using a Stable Isotope Mass Spectrometric Technique. J Applied Physiology 94(6)2203-2211 Jun. 2003.*
Neese R. Measurement in vivo of Proliferation Rates of Slow turnover Cells by 2H2O Labeling of the Deoxyribose Moiety of DNA. PNAS 99(24)15345-15350, Nov. 2002.*
Hellerstein M. Mass Isoptomer Distribution Analytsis at Eight Years. American J Physiology vol. 276, E1146-1170, 1999.*
Hsieh E. Dynamics of Keratinocytes in vivo Using 2H2O Labeling. J Investigative Dermatology 123(3)530-536, 2004.*
Neese R. Advances in the Stable Isotope Mass Spectrometric Measurement of DNA Synthesis and Cell Proliferation Analytical Biochemistry 298(2)189-195, 2001.*
U.S. Appl. No. 10/519,121, filed Sep. 15, 2003, Hellerstein.
U.S. Appl. No. 10/523,250, filed Jan, 26, 2005, Hellerstein.
U.S. Appl. No. 10/526,860, filed Sep. 4, 2003, Hellerstein.
U.S. Appl. No. 10/963,967, filed Oct. 12, 2004, Hellerstein.
U.S. Appl. No. 10/997,323, filed Nov. 23, 2004, Hellerstein.
U.S. Appl. No. 11/064,197, filed Feb. 22, 2005, Hellerstein.
U.S. Appl. No. 11/078,083, filed Mar. 11, 2005, Hellerstein.
U.S. Appl. No. 11/094,387, filed Mar. 29, 2005, Hellerstein.
International Search Report mailed on Aug. 20, 2004, for PCT application No. PCT/US03/10554 filed on Apr. 4, 2003, 4 pages.
International Search Report mailed Jul. 8, 2004, for PCT patent application No. PCT/US03/27623 filed on Sep. 4, 2003, 4 pages.
International Search Report mailed on Jan. 19, 2005, for PCT application No. PCT/US03/29361 filed on Sep. 15, 2003, 4 pages.
International Search Report mailed on Mar. 25, 2005, for PCT application No. PCT/US04/39722 filed on Nov. 24, 2004, 3 pages.
International Search Report mailed on Apr. 4, 2005, for PCT application No. PCT//US04/21063 filed on Jun. 29, 2004, 2 pages.
"New Diagnostic Technique Could Help Treat AIDS," Agence France-Presse, Dow Jones News/Retrieval, Feb. 17, 1998, pp. 1-2.
Adami, H.O. et al. (1995) "The Aetiology and Pathogenesis of Human Breast Cancer" *Mutation Research* 333: 29-35.
Anderson, R.W. et al. (1998) "Direct HIV Cytopathicity Cannot Account for CD4 Decline in AIDS in the Presence of Homeostasis: A Worst-Case Dynamic Analysis" *J. AIDS and Human Retrovirology* 17:245-252.
Asher, E. et al. (1995) "Evaluation of Cell Death in EBV-Transformed Lymphocytes Using Agarose Gel Electrophoresis, Light Microscopy and Electron Microscopy" *Leukemia and Lymphoma* 19:107-119.
Bach, Simon P. et al. (2000) "Stem Cells: The Intestinal Stem as a Paradigm" Carcinogenesis 21(3): 469-476.
Black, G.E. et al. (Jan. 2001) "Labeling DNA with Stable Isotopes: Economical and Practical Considerations," *BioTechniques* 30:134-140.
Blau, K. and Halket, J. eds. (1993) *Handbook of Derivatives for Chromatography*, 2nd Edition, John Wiley & Sons Ltd., England.

Bravo, Elena et al. (1994) "Decreased Hepatic Uptake and Processing of High Density Lipoprotein Unesterified Cholesterol and Cholesteryl Ester with Age in the Rat" J. Biochem. 116: 1088-1095.
Brown, Alan S. et al (1998) "Treating Patients with Documented Atherosclerosis to National Cholesterol Education Program-Recommended Low-Density-Lipoprotein Cholesterol Goals with Atorvastatin, Fluvastatin, Lovastatin and Simvastatin" J. Am. Coll. Cardiol. 32: 665-672.
Bucy, R.P. et al. (1998) "Analysis of Lymph Node Biopsies in HIV Infected Patients Before and After HAART" *Abstract, 5th Conference on Retroviruses and Opportunistic Infections, Session 66* 519:177.
Caldwell, K.A. et al. (1993) "Quantification of Peptide Isotopomer Abundances and Determination of Protein (sic) Turnover Rates by Using Mass Isotopomer Distribution Analysis" *Abstract, 41st Annual Amer. Society Mass Spectrometry on Mass Spectrometry*, p. 331a.
Cassella, C.R. et al. (1997) "Mechanisms of Lymphocyte Killing by HIV" *Current Opinion in Hematology* 4:24-31.
Cesar, D. et al. (1998) "Direct Measurement of CD4+ and CD8+ T Cell Proliferation Rates in Vivo in AIDS Patients Using a Stable Isotope-Mass Spectrometric Technique" *Abstract, 5th Conference on Retroviruses and Opportunistic Infections*, Chicago Illinois.
Cohen, A. et al. (1983) "Purine and Pyrimidine Metabolism in Human T Lymhocytes," *J. Biol. Chem.* 258(20):12334-12340.
Cohen, J. (1998) "Failure Isn't What It Used to Be . . . But Neither is Success" *Science* 279:1133-1134.
Conners, M. et al. (1997) "HIV Infection Induces Changes in CD4+T-Cell Phenotype and Depletions Within the CD4+T-Cell Repertoire that are not Immediately Restored by Antiviral of Immune-Based Therapies" *Nature Medicine* 3(5):533-540.
Crain, P.F.(1990) "Preparation and Enzymatic Hydrolysis of DNA and RNA for Mass Spectrometry," *Meth. Enz.* 193:782-790.
Deeks, S. et al. (1998) "Viral Load and CD4+ T Cell Changes in Patients Failing Potent Protease Inhibitor Therapy" *Abstract, 5th Conference on Retroviruses and Opportunistic Infections, Session 53*, 419:158.
Dimitrov, D.S. et al. (1995) Scientific Correspondence, *Nature* 375:194-195.
Gorochov, G. et al. (1998) "Perturbation of CD4+ and CD8+ T-Cell Repertoires During Progression to AIDS and Regulation of the CD4+Repertoire During Antiviral Therapy," *Nature Medicine* 4(2):215-221.
Gratzner, H.G. (1982) "Monoclonal Antibody to 5-Broma-and 5-Iododeoxyuridine: A New Reagent for Detection of DNA Replication" *Science* 218:474-475.
Hellerstein, M.K. et al. (1997) "T Cell Turnover in HIV-1 Disease," *Immunity* 7:583-589 (Nov. 1997).
Ho, D.D. et al. (1995) "Rapid Turnover of Plasma Virions and CD4 Lymphocytes in HIV-1 Infection," *Nature* 373:123-126.
Hsieh, Elaine A. et al. (2004) "Dynamics of Keratinocytes in Vivo Using 2H2O Labeling: A Sensitive Marker of Epidermal Proliferation State," J Invest Dermatol, 123: 530-536.
James, J.S. (1998) "Clinical Implications of Virological Failure: Interview with Steven Deeks, M.D., San Francisco General Hospital," *AIDS Treatment News*, 289:6-7.
Lipkin, M. (1987) "Proliferation and Differentiation of Normal and Diseased Gastrointestinal Cells" In *Physiology of the Gastrointestinal Tract*, L.R. Johnson ed., Raven Press, New York, pp. 255-284.
Maentausta, O. et al. (1979) "Radioimmunoassay of Conjugated Cholic Acid, Chenodeoxycholic Acid, and Deoxycholic Acid from Human Serum, with Use of 125l-Labeled Ligands" Clin. Chem. 25(2): 264-268.
Marcolick, J.B. et al. (1995) "Failure of T-cell Homeostasis Preceding AIDS in HIV-1 Infection," *Nature Medicine*, 1(7):674-680.
McCloskey, J.A. (1990) "Electronlonization Mass Spectra of Trimethylsilyl Derivatives of Nucleosides," *Meth. Enz.* 193:825-841.
McCune, J.M. (1997) "Thymic Function in HIV- 1 Disease," *Seminars in Immunology* 9:397-404.

McLean, A.R. et al. (1995) "In Vivo Estimates of Division and Death Rates of Human T Lymphocytes," *Proc. Natl. Acad. Sci USA* 92:3707-3711.

Meier, P.R. et al. (Mar. 1981) "Rates of Protein Synthesis and Turnover in Fetal Life," *Am J Physiol.*, 240(3):E320-E324.

Mellors, J.W. et al., (1995) "Quantitation of HIV-1 RNA in Plasma Predicts Outcome after Seroconversion," *Ann. Intern. Med.* 122:573-579.

Mellors, J.W. et al. (1996) "Prognosis in HIV-1 Infection Predicted by the Quantity of Virus in Plasma," *Science*, 272:1167-70.

Messmer, Bradley T. et al. (Feb. 10, 2005) "In Vivo Measurements Document the Dynamic Cellular Kinetics of Chronic Lymphocytic Leukemia B Cells," *J. Clin. Invest.* doi:10.1172/JCI200523409.

Michie, C.A. et al. (1992) "Lifespan of Human Lymphocyte Subsets Defined by CD45 Isoforms," *Nature* 360:264-265.

Morris, Rebecca J. et al. (1997) "Evidence that Cutaneous Carcinogen-initiated Epithelial Cells from Mice are Quiescent Rather than Actively Cyling" *Cancer Research* 57:3436-3443.

Mosier, D.E. (1995) "CD4.sup.+ Cell Turnover," *Nature* 375:193-194.

Murali-Krishna, K. et al. (1998) "Counting Antigen-Specific CD8 T Cells: A Reevaluation of Bystander Activation during Viral Infection," *Immunity* 8:177-187.

Neese, R. A. et al. (Nov. 2002) "Measurement in Vivo of Proliferation Rates of Slow Turnover Cells by 2H2O Labeling of the Deoxyribose Moiety of DNA," *PNAS*, 99(24): 15345-15350.

Oyaizu, N. et al. (1995) "Role of Apoptosis in HIV Disease Pathogenesis," *J. of Clinical Immunology* 15(5):217-231.

Palmer, L.D. et al. (1997) "Telomere Length, Telomerase Activity and Replicative Potential in HIV Infection: Analysis of CD4+ and CD8+ T Cells from HIV-discordant Monozygotic Twins," *J. Experimental Medicine* 185(7):1381-1386.

Papageorgopoulos, C. et al.(1993) "Toward the Measurement of Protein Synthesis by Mass Isotopomer Distribution Analysis (MIDA):Resolution of Isotopomers in a [d.sub.3]-Leucine Enriched Synthetic Oligopeptide Using Electrospray/Quadrupole Mass Spectrometry (ESI/MS)," *Abstract, Federation of American Societies for Experimental Biology* 1022:A177.

Park, S. S., et al. (1997) "Measurement of Small Intestinal Cell Turnover with [6,6, 2H2] Glucose," *Berkeley Scientific, Abstract* 1(2):41-43.

Patton, G.M. et al. (Jul. 1979) "Measurements of Fatty Acid Synthesis by Incorporation of Deuterium from Deuterated Water," *Biochemistry*, 18(14):3186-3188.

Perelson, A.S. et al.(1996) "HIV-1 Dynamics in Vivo: Virion Clearance Rate, Infected Cell Life-Span, and Viral Generation Time," *Science* 271:1582-1586.

Perelson, A.S. et al. (1997) "Decay Characteristics of HIV-1-Infected Compartments During Combination Therapy," *Nature* 387:188-191.

Reichard, P. (1978) "From Deoxynucleotides to DNA Synthesis," *Federation Proceedings* 37(1):9-14.

Reichard, P. (1988) "Interactions Between Deoxyribonucleotide and DNA Synthesis," *Ann. Rev. Biochem.* 57:349-374.

Roda, Aldo et al. (1980) "Results with Six 'Kit' Radioimmunoassays for Primary Bile Acids in Human Serum Intercomared" *Clin. Chem.* 26(12): 1677-1682.

Roederer, M. (Jul. 1995) "T-Dell Dynamics of Immunodeficiency," *Nature Medicine* 1(7):621-622.

Sawada, S. et al. (1995) "Comparison of Autoradiography, Liquid Scintillation Counting and Immunoenzymatic Staining of 5-bromo-2'-deoxyuridine for Measurement of Unscheduled DNA Synthesis and Replicative DNA Synthesis in Rat Liver," *Mutation Research* 344:109-116.

Scalise, K. (Feb. 11-17, 1998) "Tracking T-Cells in AIDS Patients: A Safe Reliable Method of Measuring Human Cell Generation Rates," *Berkeleyan*, p. 3.

Shigenaga, M.K. et al. (1994) "Assays of Oxidative DNA Damage Biomarkers 8-Oxo-2'-deoxyguanosine and 8-Oxoguanine in Nuclear DNA and Biological Fluids by High-Performance Liquid Chromatography with Electrochemical Detection, " *Methods in Enzymology* 234:16-33.

Smith, et al. (1983) "The Phosphogluconate Odixative Pathway," in *Principles of Biochemistry, 7th edition*, McGraw-Hill Book Company, pp. 417-423.

Sprent, J. et al. (1995) "CD4+ Cell Turnover," *Nature* 375:194.

Tint, G.S. et al. (1974) "Transformation of 5α-cholest-7-en-3β-ol to Cholesterol and Cholestanol in Cerebrotendinous Xanthomatosis" *Journal of Lipid Research* 15: 256-262.

Traber, P.G. et al. (1991) "Isolation of Intestinal Epithelial Cells for the Study of Differential Gene Expression Along the Crypt-Villus Axis," *Am. J. Physiol.* 260:G895-G903.

Wadke, M. et al. (Jul. 1973) "Fatty Acid Synthesis by Liver Perfused with Deuterated and Tritiated Water," *Biochemistry*., 12(14):2619-2624.

Wain-Hobson, S. (1995) "Virological Mayhem," *Nature* 373:102.

Waldeman, F.M. et al. (1991) "A Comparison Between Bromodeoxyuridine and 3 H Thymidine Labeling in Human Breast Tumors," *Modern Path.* 4(6):718-722.

Wei, X et al. (1995) "Viral Dynamics in Human Immunodeficiency Virus Type 1 Infection," *Nature* 373:117-122.

Wolfe, R. (1990) "Isotopic Measurement of Glucose and Lactate Kinetics," *Ann. Med.* 22:163-170.

Wolthers et al. (1998) "Rapid CD4+ T-Cell Turnover in HIV-1 Infection: a Paradigm Revisited," *Immunol.* Today 19(1):44-48.

Wolthers, K.C. et al. (1996) "T Cell Telomere Length in HIV-1 Infection: No Evidence for Increased CD+ T Cell Turnover," *Science* 274:1543-1547.

Wood, H.G. et al. (1963) "Estimation of Pathways of Carbohydrate Metabolism," *Biochemische Zeitschrift* 338:809-847.

Zhang, Z-Q. et al. (Feb. 1998) "Kinetics of CD4+ T Cell Repopulation of Lymphoid Tissues after Treatment of HIV-1 Infection," *Proc. Natl. Acad. Sci. USA* 95:1154-1159.

Zilversmit, D.B. et al. (1943) "On the Calculation of 'Turnover Time' and 'Turnover Rate' from Experiments Involving the Use of Labeling Agents," *J. of General Physiology* 26(3):325-331.

Ajie, H. O. et al. (1995). "In Vivo Study of the Biosynthesis of Long-Chain Fatty Acids Using Deuterated Water" *American Physiological Society*: E247-E252.

Jones, Peter J. H. et al. (1994). "Interaction of Dietary Fat Saturation and Cholesterol Level on Cholesterol Synthesis Measure Using Deuterium Incorporation" *Journal of Lipid Research*, vol. 35: 1093-1101.

Airhart, J., A. Vidrich, and E. A. Khairallah. Compartmentation of free amino acids for protein synthesis in rat liver. *Biochem J* 140: 539-45, 1974.

Bonotto, S., I. Ndoite, G. Nuyts, E. Fagniart, and R. Kirchmon. Study of the distribution and biological effects of $^3H$ in the Algae Acetabularia, Chlamydomonas and Porphyra. *Curr Top Rad Quart* 12: 115-132, 1977.

Chinkes, D. L., A. Aarsland, J. Rosenblatt, and R. R. Wolfe. Comparison of mass isotopomer dilution methods used to calculate VLDL production in vivo. *Am. J. Physiol.* 271 (*Endocrinol. Metab.* 34): E373-E383, 1996.

Conrads, Thomas P. and Timothy D. Veenstra. Stable Isotope Labeling in Proteomics *The Synthesis Cambridge Isotope Laboratories* 3 (2): 1-3, Jan. 2002.

Etnier, E., C. Travis, and D. Hetrick. Metabolism of organically bound tritium in man. *Rad Res* 100: 487-502, 1984.

Hellerstein, Mark K. et al. Measurement of synthesis rates of slow-turnover proteins from $^2H_2O$ incorporation into non-essential amino acids (NEAA) and application of mass isotopomer distribution analysis (MIDA). *Faseb Journal Experimental Biology 2002: Meeting Abstracts* 16: pp. A256, 2002.

Hellerstein, M. K., and R. A. Neese. Mass isotopomer distribution analysis at eight years: theoretical, analytic, and experimentatl considerations. *Am. J. Physiol* 276: E1146-70, 1999.

Hellerstein, M. K., and R. A. Neese. Mass isotopomer distribution analysis: a technique for measuring biosynthesis and turnover of polymers. *Am J Physiol* 263: E988-1001, 1992.

Hellerstein, M. K. Methods for measurement of fatty acid and cholesterol metabolism. *Current Opinion in Lipidology* 6: 172-181, 1995.

Humphrey, T., and D. Davies. A new method for the measurement of protein turnover. *Biochem J.* 148: 119-127, 1975.

Humphrey, T., and D. Davies. A sensitive method for measuring protein turnover based on the measurement of 2-$^3$H-labeled amino acids in proteins. *Biochem J.* 156: 561-568, 1976.

Jungas, R. L. Fatty acid synthesis in adipose tissue incubated in tritiated water. *Biochemistry* 7: 3708-17, 1968.

Katz, J., and R. Rognstad. Futile cycles in the metabolism of glucose. *Curr Top Cell Regul* 10: 237-89, 1976.

Kelleher, J. K., and T. M. Masterson. Model equations for condensation biosynthesis using stable isotopes and radioisotopes. *Am. J. Physiol.* 262 (*Endocrinol. Metab.* 25): E118-E125, 1992.

Khairallah, E. A., and G. E. Mortimore. Assessment of protein turnover in perfused rat liver. Evidence for amino acid compartmentation from differential labeling of free and tRNA-gound valine. *J Biol Chem* 251: 1375-84, 1976.

Kim, J. et al. "A New Stable Isotope-Mass Spectrometric (MS) Method to Measure Proliferation Rates of Colon Epithelial Cells" *Faseb Journal* 14 (4): pp. A718, 2000.

Mathur-De vré, R., and J. Binet. Molecular aspects of tritiated water and natural water in radiation biology. *Prog Biophys Molec Biol* 43: 161-193, 1984.

Mewissen, D., M. Furedi, A. Ugarte, and J. Rust. Comparative incorporation of tritium from tritiated water versus tritiated thymidine, uridine or leucine. *Curr Top Rad Res Quart* 12: 225-254, 1977.

Papageorgopoulos, Christina et al. Measuring Protein Synthesis by Mass Isotopomer Distribution Analysis (MIDA) *Analytical Biochemistry* 267: 1-16, 1999.

Patterson, B. W., and R. R. Wolfe. Concentration dependence of methyl-palmitate isotope ratios by electron impact ionization gas chromatography/mass spectrometry. *Biol. Mass Spectrom.* 22: 481-486, 1993.

Previs, Stephen F. et al. Estimation of Protein Turnover In Vivo Using $D_2O$. *Diabetes Abstract Book, 61st Scientific Sessions*, vol. 50 Supplement 2: A301, Jun. 2001.

Van Hinsbergh, V.W.M., et al. Palmitate Oxidation by Rat Skeletal Muscle Mitochondria, *Archives of Biochemistry and Biophysics* 190 (2): 762-771, 1978.

Veerkamp, Jacques H. et al. $_{14}CO_2$ Prodution Is No Adequate Measure of [$^{14}$C]Fatty Acid Oxidation. *Biochem Medicine and Metabolic Biology*. 35: 248-259 (1986).

McCune, Joseph M. et al. "Factors Influencing T-Cell Turnover in HIV-1-Seropositive Patients." *The Journal of Clinical Investigation* 105:R1-R8, Oct. 1999.

Christianen Mark P. et al. "Effect of Dietary Energy Restriction on Glucose Production and Substrate Utilization in Type 2 Diabetes." *Diabetes* 49: 1691-1699, Oct. 2000.

Wang, Wei et al. "Effect of Nicotinic Acid on Fatty Acid Kinetics, Fuel Selection, and Pathways of Glucose Production in Women." *Am. J. Physiol. Endocrinol. Metab.* 279: E50-E59, 2000.

Parks, Elizabeth J. et al. "Carbohydrate-induced Hypertriacylglycerolemia: Historical Perspective and Review of Biological Mechanisms." *Am. J. Nutr.* 2000; 71:412-433.

Leung, Gordon K. et al. "A Deficiency on Microsomal Triglyceride Transfer Protein Reduces Apolipoprotein B Secretion." *The Journal of Biological Chemistry* 275, No. 11:7515-7520, 2000.

Hudgins, Lisa C. et al. "Relationship Between Carbohydrate-Induced Hypertriglyceridemia and Fatty Synthesis in Lean and Obese Subjects." *Journal of Lipid Research* 41:595-604, 2000.

Davis, Ajuah et al. "Effect of Pinitol Treatment on Insulin Action in Subjects With Insulin Resistance." *Diabetes Care* 23, No. 23:1000-1005, 2000.

Lammert, Ole et al. "Effects of Isoenergetic Overfeeding of Either Carbohydrate or Fat in Young Men." *British Journal O Nutrition* 84:233-245, 2000.

Parks, Elizabeth J. et al. "Dependence of Plasma α-Tocopherol Flux on Very Low-Density Triglyceride Clearance in Humans." *Free Radical Biology & Medicine* 29, No. 11: 1151-1159, 2000.

Véniant, Murielle M. et al. "Defining the Atherogenicity of Large and Small Lipoproteins Containing Apolipoproteins B100." *The Journal of Clinical Investigation* 106, No. 12: 1501-1510, 2000.

Fagerquist, Clifton K. et al. "Elimination of the Concentration Dependence in Mass Isotopomer Abundance Mass Spectrometry of Methyl Palmitate Using Metastable Atom Bombardment." *J. Am. Soc. Mass Spectrometry* 12:754-761, 2001.

Hellerstein, M. et al. "Directly Measured Kinetics of Circulating T Lymphocytes in Normal and HIV-1-Infected Humans." *Nature Medicine* 5, No. 1:83-89. 1999.

Teixeira, Luciléia et al. "Poor CD4 T Cell Restoration After Supression of HIV-1 Replication May Reflect Lower Thymic Function." *AIDS* 15, No 14:1749-1756, 2001.

Hellerstein, Marc K. "No Common Energy: de Novo Lipogenesis as the Road Less Traveled." *Am. J. Clin. Nutr.* 74:707-708,2001.

Neese, Richard A. et al. "Advances in the Stable Isotope-Mass Spectrometric Measurement of DNA Synthesis and Cell Proliferation." *Analytical Biochemistry* Feb. 14, 2001.

Mohri, Hiroshi et al. "Increased Turnover of T Lymphocytes in HIV-1 Infection and its Reduction by Antiretroviral Therapy." *J. Exp. Med.* 194, No. 9: 1277-1287, no date given.

Pantaleo, Giuseppe "Unraveling the Strands of HIV's Web." *Nature Medicine* 5, No. 1: 27-28, 1999.

Hellerstein, Marc K. "Carbohydrate-Induced Hypertriglyceridemia: Modifying Factors and Implications for Cardiovascular Risk." *Nutrition and Metabolism*. pp. 33-40, 2002.

Trappe, T. A. et al. "Effect of Ibuprofen and Acetaminophen on Postexercise Muscle Protein Synthesis." *Am. J. Physiol. Endocronol Metab* 282:E551-E556, 2002.

Deeks, Steven G. et al. "CD4+ T Cell Kinetics and Activation in Human Immunodeficiency Virus-Infected Patients Who Remain Viremic Despite Long-Term Treatment with Protease Inhibitor-Based Therapy." *The Journal of Infections Diseases* 185:315-323, 2002.

Neese, R. A. et al. "Measurement of Endogenous Synthesis of Plasma Cholesterol in Rats and Humans Using MIDA." *The American Physiological Society*. pp. E139-E147, 1993.

Hellerstein, Marc K. et al. "Model for Measuring Absolute Rates of Hepatic De Novo Lipogenesis and Reesterification of Free Fatty Acids." *The American Physiological Society*. pp. E814-E820, 1993.

Hellerstein, Marc K. et al. "Mass Isotopomer Distribution Analysis for Measuring Fluxes Through Intracellular Metabolic Pathways and Biosynthetic Rates of Polymers."*IFAC Modeling and Control in Biomedical Systems*. pp. 353-359, 1994.

Hellerstein, Marc K. et al. "Glycoconjugates as Noninvasive Probes of Intrahepatic Metabolism: Pathways of Glucose Entry into Compartmentalized Hepatic UDP-glucose Pools during Glycogen Accumulatio." *Proceedings of the National Academy of Sciences of the United States of America.* 83, Issue 18: 7044-7048, 1986.

Neese, Richard A. et al. "Gluconeogenesis and Intrahepatic Triose Phosphate Flux in Response to Fastinf or Substrate Loads." *The Journal of Biological Chemistry*. 270, No. 24, pp. 14452-14463, 1995.

Schwarz, Jean-Marc et al. "Short-Term Alterations in Carbohydrate Energy Intake In Humans." *The American Society for Clinical Investigation*. 96: 2735-2743, 1995.

Hudgins, Lisa C. et al. "Human Fatty Acid Synthesis is Stimulated by a Eucaloric Low Fat, High Carbohydrate Diet." *The American Society for Clinical Investigation*. 97, No. 9: 2081-2091, 1996.

Hellerstein, Marc K. et al. "Measurement of Hepatic $R_a$ UDP-glucose in Vivo in Rats: Relation to Glycogen Deposition and Labeling Patterns." *The American Physiological Society*. pp. E155-E162, 1997.

Hellerstein, Marc K. et. al. et al. "Altered Fluxes Responsible For Reduced Hepatic Glucose Production and Glusoneogenesis by Exogenous Glucose in Rats." *The American Physiological Society*. pp. E163-E172, 1997.

Hellerstein, Marc K. et. al. et al. "Hepatic Gluconeogenic Fluxes and Glycogen Turnover During Fasting in Humans."*J. Clin. Invest.* 100, No. 5:1305-1319, 1997.

Dekker, Evelien et al. "Glucose Homeostasis in Children with Falciparum Malaria: Precursor Supply Limits Gluconeogenesis and Glucose Production." *Journal of Clinical Endocrinology and Metabolism*. 82, No. 8: 2514-2519, 1997.

Macallan, Derek C. et al. "Measurement of Cell Proliferation by Labeling of DNA with Stable Isotope-Labeled Glucose: Studies in Vitro, in Animals, and in Humans." *Proc. Natl. Acad. Sci.* 95: 708-713, 1998.

Bandsma, Robert H. J. et al. "Contribution of Newly Synthesized Cholesterol to Rat Plasma and Bile Determined by Mass Isotopomer distribution Analysis: Bile-Salt Flux Promotes Secretion of Newly Synthesized Cholesterol into Bile." *Biochem. J.* 329: 699-703, 1998.

Hoh, Rebecca et al. "De Novo Lipogenesis Predicts Short-Term Body-Composition Response by Bioelectrical Impedance Analysis to Oral Nutritional Supplements in HIV- Associated Wasting." *Am. J. Clin. Nutr.* 68:154-163, 1998.

Siler, Scott Q. et al. "The Inhibition of Gluconeogenesis Following Alcohol in Humans." *The American Physiological Society.* pp. E897-E907, 1998.

Siler, Scott Q. et al. "VLDL-Triglyceride Production After Alcohol Ingestion, Studied Using [2-$^{13}$C] Glycerol." *Journal of Lipid Research* 39: 2319-2328, 1998.

Van Loan, Marta D. et al. "Monitoring Changes in Fat-Free Mass in HIV-Positive Men With Hypotestosteronemia and AIDS Wasting Syndrome Treated With Gonadal Hormone Replacement Therapy." *AIDS* 13:241-248, 1999.

Fagerquist, Clifton K. et al. "Molecular Ion Fragmentation and Its Effects on Mass Isotopomer Abundance of Fatty Acid Methyl Estes Ionized By Electron Impact." *J. Am. Soc. Mass. Spectrom* 10: 430-439, 1999.

Jung, Hye Rim. et al. "Metabolic Adaptations to Dietary Fat Malabsorption in Chylomicron-Deficient Mice." *Biochem. J.* 343: 473-478, 1999.

Hellerstein, Marc K. et al "The Changing Face of AIDS: Translators Needed." *Am. J. Clin. Nutr.* 70: 787-788, 1999.

Parks, Elizabeth J. et al. "Effects of a Low-Fat, High-Carbohydrate Diet on VLDL-Triglyceride Assembly, Production, and Clearence." *J. Clin. Invest.* 104, No. 8:1087-1096, 1999.

Wolf, George. "The Effect of Fasting and Fructose and Glucose Infusion on Gluconeogenesis and Triose Phosphate Flux in Rats in Vivo." *Nutrition Reviews* . 53, No. 10:299-302, 1995.

Hellerstein, Marc K. et al. "Effects of Cigarette Smoking and its Cessation on Lipid Metabolism and Energy Expenditure in Heavy Smokers." *J. Clin. Invest.* 93: 265-272, 1994.

Winett, Richard et al. "Exercise Regimens for Men With HIV." *JAMA.* Jul. 12, 2000; 284(2): 175-6.

Bandsma. Robert H. J. et al. The Contribution of Newly Synthesized Cholesterol to Bile Salt Synthesis in Rats Quantified By Mass Isotopomer Distribution Analysis. *Biochimica et Biophysica Acta* 1483: 343-351, 2000.

Hellerstein, Marc K. et al. "Measurement of T-Cell Kinetics: Recent Methodologic Advances." *Trends Immunology Today.* 20, No. 10: 438-441, 1999.

Hellerstein, Marc K. et al. "Directly Measured Kinetics of Circulating T Lymphocytes in Normal and HIV-1-Infected Humans." *Nature Medicine* , 5, No. 1: 83-89, 1999.

Bingham, SA (Jan. 1994) "The use of 24-h urine samples and energy expenditure to validate dietary assessements" *American Journal of Clinical Nutrition* 59 (1 suppl): pp. 227S-231S.

Craig, SB et al. (Sep. 1996) "The Impact of Physical Activity on Lipids, Lipoproteins, and Blood Pressure in Preadolescent Girls" *Pediatrics* (3 Pt 1): pp. 389-395.

Misell, L. et al. "A new *in vivo* Stable Isotope Method for Measuring Mammary Epithelial Cell Proliferation." *Faseb Journal Experimental Biology* 2000 14(4): *Meeting.Abstract* 550.5: pp. A786.

Scott M. Turner et al. "Measurement of Triglyceride (TG) Synthesis in vivo $^2$H$_2$O Incorporation into TG-Glycerol and Application of Mass Isotopomer Distribution Analysis (MIDA)." *Experimental Biology* 2002, 16: *Meeting.Abstract* 361.9: pp. A400.

Fernando Antelo et al. "Adipose Triglyceride (TG) Turnover and de novo Lipogenesis (DNL) in Humans: Measurement by Long-Term $^2$H$_2$O Labeling and Mass Isotopomer Distribution Analysis (MIDA)." *Experimental Biology.* 2002, 16: *Meeting Abstract.* 361. 10: pp. A400.

J.C. Waterlow "Protein Turnover in the Whole Animal." *Invest. Cell Pathol.*, 3: 107-119 (1980).

Eugene D. Robin and Ronald Wong. "Mitochondria DNA Molecules and Virtual Number of Mitochondria per Cell in Mammalian Cells." *Journal of Cellular Physiology* 136:507-513 (1988).

Steven N. Blair, et al. "Changes in Physical Fitness and All-Cause Mortality: A Prospective Study of Healthy and Unhealthy Men." *JAMA*, 273, No. 14: 1093-1098, (1995).

Chong Do Lee, et al. "Cardiorespiratory Fitness, Body. Composition, and All-Cause and Cardiovascular Disease Mortality in Men[1-3]." *Am.J. Clin Nutr*, 69:373-380, (1999).

Giuseppe Attardi and Gottfried Schatz, "Biogenesis of Mitochondria." *Ann. Rev. Cell Biol.* 4:289-333, (1998).

David A. Clayton. "Replication and Transcription of Vertebrate Mitochondrial DNA." *Annu. Rev. Cell Biol.* 7:453-478, (1991).

J.R. Bickenbach. "Identification and Behavior of Label-Retaining Cells in Oral Mucosa and Skin." *J Dent Res*, 1611-1620, (1981).

Rebecca J. Morris, et al. "Evidence that a Slowly Cyling Subpopulation of Adult Murine Epidermal Cells Retains Carcinogen." *Cancer Research* 46, 3061-3066, (1986).

Simon P. Bach et al. "Stem Cells: The Intestinal stem as a Paradigm." *Carcinogenesis* 21, No. 3:469-476, (2000).

Rebecca J. Morris, et al. "Evidence that Cutaneous Carcinogen-initiated Epithelial Cells from Mice are Quiescent Rather than Actively Cyling." *Cancer. Research.* 57:3436-3443, (1997).

J.P. Sunter, et al. "Cell Population Kinetics in the Epithelium of the Colon of the Male Rat." *Virchows Archiv. B Cell Path.* 26: 275-287 (1978).

Barry Goz "The Effects of Incorporation of 5-Halogenated Deoxyuridines into DNA of Eukaryotic Cells." *Macological Reviews* 29, No. 4:249-272. (1978).

B. Rocha et al., "Accumulation of Bromodeoxyuridine-Labelled Cells in Central and Peripheral Lymphoid Organs: Minimal Estimates of Production and Turnover Rates of Mature Lymphocytes." *Eur. J. Immunol.* 20: 1697-1708 (1990).

Martin Lipkin et al. "Cell Proliferation Kinetics in the Gastrointestinal Tract of Man. I. Cell Renewal in Colon and Rectum." *Journal of Clinical Investigations* 42, No. 6:767-776, (1963).

K.M. Pozharisski et al., "Study of Kinetics of Epithelial Cell Populations in Normal Tissues of the Rat's Intestines and in Carcinogenesis." Exp. Path., Bd. 18:387-406, (1980).

Bertani, Roberta et al. "Measurement of Total Body Water (TBW) Through In Vivo Dilution of Tracer Compounds: Use of D$_2$O and its Determination by FT Infrared Spectroscopy." *Annali diChimica* 92:135-138, Jan. 2002.

Jennings, Graham et al. "The Use of Infrared Spectrophotometry for Measuring Body Water Spaces." *Clinical Chemistry* 45, No. 7: 1077-1081, Jul. 1999.

Roberts, S. B. "The Use of the doubly labeled water method for Measurement of Energy Expenditure, Total Body Water, Water Intake, and Metabolizable energyIntake in Humans and Small Animals." *Canadian J of Physiology and Pharmacology*, vol. 67, No. 10: 1190-1198, Oct. 1989.

Lewanczuk, Richard Z et al. "Comparison of the [$^{13}$ C] Glucose Breath Test to the Hyperinsulinemic-Euglycemic Clamp When Determining Insulin Resistance" *Diabetes Care*, vol. 27, No. 2:441-447, Feb. 2004.

Hellerstein, Marc K. "In Vivo Measurement of Fluxes Through Metabolic Pathways: The Missing Link in Functional Genomics and Pharmaceutical Research" *Annu. Rev. Nutr.* 23: 379-402, Mar. 2003.

International Search Report mailed on Jun. 29, 2004, for PCT patent application No. PCT/US03/04183 filed on Feb. 12, 2003, 4 pages.

International Search Report mailed on Apr. 13, 2004, for PCT application No. PCT/US03/20052 filed on Jun. 25, 2003, 3 pages.

International Search Report mailed on Jul. 9, 2004, for PCT patent application No. PCT/US03/35107 filed on Nov. 4, 2003, 2 pages.

Guo, Z.K. et al., (2000) "De novo lipogenesis in adipose tissue of lean and obese woman: application of deuterated water and isotope ratio mass spectrometry," International Journal of Obesity, 24: 932-937.

Hellerstein, Marc K. et al. (1986) "Glycoconjugates as Noninvasive Probes of Intrahepatic Hepatic UDP-glucose Pools during Glycogen Accumulation." Proceedings of the National Academy of Sciences of the United States of America 83, Issue 18: 7044-7048.

Hellerstein, Marc K. et al. (1997) "Measurement of Hepatic Ra UDP-glucose in Vivo in Rats: Relation to Glycogen Deposition and Labeling Patterns" Am. J. Physiol. 272: E155-E162.

Hellerstein, Marc K. et al. (1999) Mass Isotopomer Distribution Analysis at Eight Years: Theoretical, Analytic, and Experimental Considerations. Am. J. Physiol. 276: E1146-E1170.

Hellerstein, Marc K. (2004) "New stable isotope-mass spectrometric techniques for measuring fluxes through intact metabolic pathways in mammalian systems : introduction of moving pictures into functional genomics and biochemical phenotyping," Metabolic Engineering, 6: 85-100.

Morsches, Bernhard (1976) "Tierexperimentelle Untersuchugen uber die Beziehungen zwischen der Hydroxyprolinausscheidung im Urin und den Hydroxyprolinfraktionen im Serum," Der Hautarzt, 27:.

Ravichandran, L.V. et al., (Jun. 1991) "In vivo labeling studies on the biosynthesis and degradation of collagen in experimental myocardial infarction," Biochemistry Journal, 24(3): 405-414.

Scheibner, Jurgen et al. (1999) "Complex Feedback Regulation of Bile Acid Synthesis in the Hamster: The Role of Newly Synthsized Cholesterol," Hepatology, 30: 230-237.

Supplementary Partial European Search Report mailed mar. 9, 2006, for European patent application No. EP 03713429.3 , filed Feb. 12, 2003, 6 pages.

Australian Patent Office Search Report mailed Aug. 26, 2005, for Singapore patent application No. SG 200500571-5, filed Jul. 25, 2003, 5 pages.

Heck, Steven D. et al., (Apr. 1996) "Posttranslational amino acid epimerization: Enzyme-catalyzed isomerization of amino acid residues in peptide chains," Proc. Natl. Acad. Sci USA, 93(9): 4036-4039.

International Search Report mailed Aug. 1, 2005, for PCT application No. PCT/US2005/08265, filed Mar. 11, 2005, 4 pages.

Lutton, C. et al. (1990) "Critical analysis of the Use of 14C-acetate for Measuring In Vivo Rat Cholesterol Synthesis," Reprod Nutr Dev, 30: 71-84.

Ouguerram, K. et al. (Jan. 2002) "A New Labeling Approach Using Stable Isotopes to Study In Vivo Plasma Cholesterol Metabolism in Humans," Metabolism, 51(1): 5-11.

Patterson, Bruce W. et al. (Aug. 1997) "Measurement of Very Low Stable Isotope Enrichments by Gas Chromatography/Mass Spectrometry: Application to Measurement of Muscle Protein Synthesis," Metabolism, 46(8): 943-948.

Rooyackers, Olav E. et al. (Oct. 1996) "Tracer Kinetics Are of Limited Value to Measure In Vivo Protein Synthesis and Degradation Rates in Muscle of Anesthetized Rats," Metabolism, 45(10): 1279-1283.

Scheibner, Jurgen et al. (1993) "Bile Acid Synthesis from Newly Synthesized Vs. Preformed Cholesterol Precursor Pools in the Rat," Hepatology, 17: 1095-1102.

Supplementary partial European Search Report mailed Aug. 17, 2005, for European patent application No. EP 03749756.7, filed Sep. 15, 2003, 6 pages.

International Search Report for PCT application PCT/US03/23340, filed Jul. 25, 2003, mailed Aug. 18, 2004: 4 pages.

International Search Report for PCT application PCT/US03/29526, filed Sep. 16, 2003, mailed Aug. 18, 2004: 3 pages.

Bier, D. M. (1997) "Stable isotopes in biosciences, their measurement and models for amino acid metabolism" Eur J Pediatr 146 [Supp. 1]: S2-S8.

GYGI, Steven and Ruedi Aebersold (2000) "Using mass Spectrometry for quantitive proteomics" *Proteomics: A Trends Guide*: 31-36.

Hansen, Andrew P. et al. (1992) "A Practical Method for Uniform Isotopic Labeling of Recombinanat Proteins in Mammalian Cells" 31 (51): 12713-12718.

Ong, Shao-En et al. (2002) "Stable Isotope Labeling by Amino Acids in Cell Culture, SILAC, as a Simple and Accurate Approach to Expression Proteomics" *Molecular and Cellular Proteomics* 1: 376-386.

Paša-Tolic, Ljiljana et al. (1999) "High Throughput Proteome-Wide Precision Measurements of Protein Expression Using Mass Spectrometry" *J. Am. Chem. Soc.* 121: 7949-7950.

Shevchenko, Andrej et al. (1997) "Rapid 'de Novo' Peptide Sequencing by a Combination of Nanoelectrospray, Isotopic labeling and a Quadrupole/Time-of-flight Mass Spectrometer" Rapid Communications in Mass Spectrometry 11: 1015-1024.

Veenstra, Timothy D. et al. (2000) "Proteome Analysis Using Selective Incorporation of Isotopically Labeled Amino Acids" *J. Am. Soc. Mass. Spectrom.* 11: 78-82.

* cited by examiner

METHODS FOR COMPARING RELATIVE FLUX RATES OF TWO OR MORE BIOLOGICAL MOLECULES IN VIVO THROUGH A SINGLE PROTOCOL

RELATED APPLICATION

This application claims priority to U.S. Provisional Patent Application Ser. No. 60/484,626 filed Jul. 3, 2003.

This invention was made with Government support under Grant (Contract) Nos. R01-AI43866-01AI and R01-AI43866-01AI awarded by the National Institutes of Health. The Government has certain rights to this invention.

FIELD OF INVENTION

This invention relates to techniques for measuring and comparing relative molecular flux rates of the same or different classes of biological molecules in living systems. More particularly, it relates to techniques of administering isotope-labeled water to one or more tissues or individuals, and comparing the relative molecular flux rates of two or more biological molecules relevant to disease or to the effects of drug therapies on disease, even if the biological molecules are of different chemical classes.

BACKGROUND

In the field of drug development and discovery, there has been a long-recognized need for functional biochemical markers to validate the hypothesized phenotypic consequences of hypothesized gene or protein targets and of candidate drugs. Because of rapid technologic advances in the tools for identifying candidate targets and drugs in recent years, in particular the development of highly efficient genomic and proteomic tools for identifying potential targets of therapy (i.e., "therapeutic targets") and highly efficient combinatorial chemistry and high-throughput screening assays for generating candidate chemical or biological therapeutic leads, the need for phenotypic screening tools to eliminate ineffective or toxic candidates has become the single greatest challenge in drug development and discovery. There are too many targets and too many lead compounds for pharmaceutical companies to pursue all of them fully. Accordingly, this overwhelming number of candidate therapeutic targets and lead compounds must be filtered, to eliminate ineffective or toxic candidates early in the drug development process. At present, however, there are no commercially available, high-throughput screening tools available for phenotypic characterization or toxicity assessment. This deficiency represents a serious gap in the pharmaceutical industry's repertoire of tools.

The capacity for vertical integration of tests used at different steps in the drug development and discovery process, ranging from pre-clinical studies in animals to human approval trials, such as FDA phase III trials, would also be extremely useful for pharmaceutical companies. Tests that could be used in the same manner and form at all levels of a drug's development process would allow comparisons across each level and internal validation of a drug's action as it advances through the development process.

Technical limitations have held back the development of high-throughput universal screening procedures for measuring biochemical phenotypes, in contrast to genotypes. The reason for this gap is that the true unit of operational function (i.e., the phenotype) in biology is not the gene or the protein in isolation, but is the dynamic flow of molecules through metabolic pathways in fully assembled systems (i.e., fluxes or kinetics of molecules). Although research techniques for measuring the concentrations of molecules (such as immunoassay, standard clinical chemistry, genomics/proteomics and other conventional high-throughput methods) are highly advanced, research techniques for measuring molecular fluxes are not as advanced. The absence of techniques for measuring molecular kinetics applies particularly for high-throughput, multiple concurrent molecular flux measurements. This deficiency represents a fundamental problem because the altered flow of molecules through complex metabolic pathways underlies essentially all diseases. (See, for example, Stephanopoulos et al.; Hellerstein, *Annu Rev Nutr.* 2003 cited in full, infra; Kaczer and Burns).

Conventional concentration-based assays such as clinical chemistry, immunoassays, and genomics/proteomics, are all static measurements. Molecular kinetics differs from static tests in the same way that motion pictures differ from snapshots, by including the dimension of time. A completely different set of tools is required for measuring the dynamic flow of molecules than for static measurements of molecules. Measurement techniques for molecular kinetics must involve the use of isotopic tracers, to introduce the dimension of time (see, e.g., Hellerstein and Neese, *Am J Physiol* 1999, cited in full, infra; Hellerstein, *Annu Rev Nutr.* 2003). Isotope labeling creates an asymmetry in time (the label at first is not present, then it is present) and thereby allows molecular kinetics to be determined.

Isotopic labeling techniques have typically been restricted to molecular flux rates (kinetics) of a single molecule or a single biochemical class of molecule at a time. Each labeled substrate administered is generally restricted to a single chemical class of organic molecule. By way of example, a labeled amino acid, such as $^3$H-leucine or $^{13}$C-lysine, can be given to label a protein or all proteins biosynthetically in the cell or organism of interest, but other classes of molecules (e.g., lipids, DNA, carbohydrates), are not usefully or reliably labeled from amino acids. Similarly, labels for measuring DNA and RNA kinetics do not allow kinetic measurements of lipids, proteins, and other classes of molecules. For this reason, previous kinetic labeling measurements have not provided information about relative molecular flux rates of multiple biological molecules of different classes, through a single protocol.

Often, it is the combinations or comparisons of different molecular flux rates that is most informative regarding biochemical consequences (phenotypes) of a drug or genetic target. (See, e.g., Hellerstein, *Annu Rev Nutr.* 2003; Stephanopoulos et al.). There is, however, a need to also analyze biomolecules from the same class but from different cell types or tissues because a comparison between the rate of proliferation of one type of cell versus the rate of another type of cell (e.g., tumor cells versus endothelial cells in various cancers) is frequently useful in evaluating therapeutic efficacy of a drug or disease diagnosis or prognosis. Accordingly, there exists a need to analyze and compare molecular flux rates of multiple classes of biological molecules concurrently in a simple, high-throughput manner. Furthermore, there exists a need to analyze biomolecules from the same class but existing in different cell types or tissues in a high-throughput manner.

SUMMARY OF THE INVENTION

In order to meet these needs, the present application is directed to a method of measuring and comparing the relative molecular flux rates of two or more biological molecules by administering isotope-labeled water. In one embodiment, the two or more biological molecules are from the same biochemical class yet are derived from different cell types or tissues. In another embodiment, the two or more biological molecules are from different biochemical classes.

The inventor has discovered that isotope-labeled water is a universal label for measuring the biosynthetic rates of essentially every major class of biological molecule, including polynucleotides, proteins, lipids, carbohydrates, glycosaminoglycans, ceramides, glycolipids, proteoglycans, and others. Moreover, isotope-labeled water has several previously unrecognized advantages as a label delivery vehicle, including extreme ease of administration, constancy of levels and long half-life in the body, absence of tissue compartments or pools, ease of long-term administration even for weeks or months, and applicability in all living systems from cells to animals (e.g., rodents) to humans. Further, technical advances in mass spectrometry and biochemical isolation protocols now allow the high throughput required for use as an effective screening technology for drug development and discovery.

In addition, measuring and comparing the relative molecular flux rates of two or more biological molecules provides substantial information about a tissue or individual in comparison to measuring a single molecular flux rate of one biological molecule. Measuring and comparing the relative molecular flux rates of two or more biological molecules allows dynamic relationships between different biological molecules to be determined (e.g., "flux distributions" or "control architecture," as discussed by researchers in control theory of complex metabolic networks—(see, e.g., Stephanopoulos)). It is these relationships, rather than any single rate in isolation, that is often the most informative or even provides pathognomonic information regarding the state of a complex biochemical network, like the living cell or organism. The capacity to determine the dynamic relationships between or among fluxes of different biological molecules allows measurement of molecular kinetics associated with diseases and conditions, therapeutic compound treatment, and toxicity of compounds, among others. In addition, administering isotope-labeled water combined with measuring and comparing relative molecular flux rates of two or more biological molecules, even when the molecules are of different chemical classes, is readily adaptable to high-throughput screening methods for comparing relative molecular flux rates of multiple classes of molecules measured through a single protocol.

In particular, the present application is directed to a method of measuring and comparing the relative molecular flux rates of two or more biological molecules, including when the molecules are of different chemical classes in an individual, by a) administering isotope-labeled water to an individual for a period of time sufficient for the label to be incorporated into two or more biological molecules to form two or more isotope-labeled biological molecules; b) obtaining one or more biological samples from a tissue or individual, wherein the one or more biological samples contain two or more of the isotope-labeled biological molecules; c) measuring the incorporation of the label in the two or more biological molecules to determine the molecular flux rates of the biological molecules; and d) comparing the molecular flux rates of the biological molecules to analyze their relative molecular flux rates.

Isotope-labeled water may be $^2H_2O$, and may be administered by any acceptable method of administration including orally, parenterally, subcutaneously, intravascularly (e.g., intravenously or intraarterially), or intraperitoneally. The individual may be a human.

Administration of isotope-labeled water may be continuous, in a single dose, or in multiple doses. The method may include the additional step of discontinuing administration of isotope-labeled water and waiting a period of time for delabeling to occur, prior to obtaining a biological sample.

In one embodiment, the biological molecules may be of different biochemical classes. In another embodiment, the biological molecules may be of the same biochemical class but derived from different cell types or tissues. In yet another embodiment, a biological molecule may be a single molecule with a defined structure.

The biological sample may be obtained pre-mortem or post-mortem. Methods of obtaining a biological sample may occur by any method, including any method of obtaining a tissue sample and any method of obtaining a biological fluid sample, including blood draw, urine collection, tissue biopsy, or other methods known in the art.

Incorporation of a label into two or more biological molecules may be detected by methods such as liquid scintillation counting, NMR, and mass spectrometry. Incorporation of isotope labels may also be detected after chemically converting biological molecules into more easily detectable molecules. For example, the biological molecule may be degraded, chemically modified, or chemically derivatized prior to analysis.

The isotope enrichment of a biological molecule may be determined by calculating the isotope enrichment or labeling pattern by mass isotopomer distribution analysis (MIDA), and applying precursor-product or exponential decay equations to determine the molecular flux rates of the two or more biological molecules.

The relative molecular flux rates of the biological molecules are compared. The comparison may be by a ratio, graphical relationship, or other comparison methods known in the art.

Biological molecules may be an entire class of molecules, a specific molecule within a class, and/or from a specific location such as an organ or subcellular organelle. In one embodiment, a first biological molecule is cellular DNA and a second biological molecule is cellular protein. In another embodiment, a first biological molecule is protein, a second biological molecule is cellular DNA, and a third biological molecule is a lipid. In yet another embodiment, a first biological molecule is cellular protein and a second biological molecule is mitochondrial DNA. In yet another embodiment, a first biological molecule is adipose tissue acyl-glyceride and a second biological molecule may be either cellular protein or cellular DNA. In a further embodiment, the first biological molecule is adipose tissue acyl-glyceride, the second biological molecule is cellular protein, and a third biological molecule is cellular DNA.

The biological sample may be tissue, such as muscle, liver, pancreas, brain, adipose tissue, spleen, intestines, heart, lung, skin, prostate, gonads, breast, synovium, blood cells, or other tissues of the body. In another aspect, a first biological molecule is protein and a second biological molecule is mRNA. In a further variation, a first biological molecule is mitochondrial cardiolipin and the second molecule is mitochondrial DNA. In yet another variation, a first biological molecule is skin keratin and a second biological molecule is skin keratinocyte DNA. In yet another embodiment, a first biological molecule is amyloid-beta protein, a second biological molecule is neuron DNA, a third biological molecule is microglia DNA, and a fourth biological molecule is galactocerebroside. In a further embodiment, a first biological molecule is amyloid-beta protein, a second biological molecule is neuron DNA, and a third biological molecule is microglia DNA. In yet a further embodiment, a first biological molecule is amyloid precursor protein, a second biological molecule is neuron DNA, a third biological molecule is microglia DNA, and a fourth biological molecule is galactocerebroside. In another embodiment, a first biological molecule is amyloid precursor protein, a second biological molecule is neuron DNA, and a third biological molecule is microglia DNA.

Biological molecules may also be specific molecules within a class of molecules. In one embodiment, a first biological molecule is triglyceride and a second biological molecule is fatty acid, and optionally, the tissue may be liver.

The biological sample may be obtained from growing tissues such as muscle, liver, adrenal tissue, prostate tissue, colon tissue, endometrial tissue, skin, breast tissue, adipose tissue, or other tissue capable of somatic growth. The biological sample may be or include tumor cells or bacteria. The two or more biological molecules may be isolated and/or detected simultaneously.

In another aspect, the invention includes methods of detecting, prognosing, or monitoring the progression of a disease or condition in one or more tissues of individuals or in individuals. The relative molecular flux rates of two or more biological molecules in a first population of tissues or individuals that lack the disease or condition are measured and compared. The relative molecular flux rates of the two or more biological molecules in a second population of one or more tissues or individuals are measured and compared. A difference between the relative molecular flux rates between the first and the second populations is then identified and used to detect, prognose, or monitor the progression of the disease or condition. Alternatively, the relative molecular flux rates of a population of one or more tissues or individuals may be measured and compared at two or more different times.

In another aspect, the invention includes methods of detecting, prognosing, or monitoring the progression of a disease or condition in one or more tissues of individuals or in individuals. The relative molecular flux rates of two or more biological molecules in a population of tissue or individuals are measured and compared before and after administering a compound. A difference between the relative molecular flux rates before and after administration is then identified and used to detect, prognose, or monitor the progression of the disease or condition. Alternatively, the relative molecular flux rates of a population of one or more tissues or individuals may be measured and compared at two or more different times.

As an example, interstitial pulmonary fibrosis (IPF) may be diagnosed, prognosed, or monitored by comparing the relative molecular flux rates of lung collagen and lung fibroblast DNA in a population of one or more individuals diagnosed with IPF to a test population of non-diseased humans. Alternatively, the relative molecular flux rates of a population of one or more tissues or individuals diagnosed with, or suspected of having, IPF may be measured and compared at two or more different times.

As another example, hyperlipidemia may be diagnosed, prognosed, or monitored by comparing the relative molecular flux rates of two or more of plasma apolipoprotein B, triglycerides, phospholipids, and cholesterol in a population of one or more individuals diagnosed with hyperlipidemia to a test population. In a further variation, familial combined hyperlipidemia may be diagnosed, prognosed, or monitored by comparing the relative molecular flux rates of apolipoprotein B and one or more of triglycerides, phospholipids, cholesterol, and/or cholesterol ester in a population of one or more individuals diagnosed with familial combined hyperlipidemia to a test population. Alternatively, the relative molecular flux rates of a population of one or more tissues or individuals may be measured and compared at two or more different times.

In a still further variation, a first biological molecule is T or B cell DNA and the second biological molecule is plasma immunoglobulin. Reduced cellular immune activation may be diagnosed, prognosed, or monitored by comparing the relative molecular flux rates of T or B cell DNA to plasma immunoglobulins in a population of one or more individuals diagnosed with reduced cellular immune activation to a test population. A reduction in the relative molecular flux rate of T or B cell DNA identifies the progression of reduced cellular immune activation in the second population. In a further variation, the first molecule may be a protein, other than plasma immunoglobulin, derived from T or B cells. Alternatively, the relative molecular flux rates of a population of one or more tissues or individuals may be measured and compared at two or more different times.

In a further variation, a first biological molecule is dermal collagen and the second biological molecule is dermal elastin. Photoaging may be diagnosed, prognosed, or monitored by comparing the relative molecular flux rates of dermal collagen to dermal elastin in a population of one or more individuals with a photoaging phenotype (skin wrinkles) to a test population. Alteration in the dermal collagen molecular flux rate relative to the dermal elastin molecular flux rate in the test population identifies altered photoaging in the population under evaluation. Alternatively, the relative molecular flux rates of a population of one or more tissues or individuals may be measured and compared at two or more different times.

The invention also includes methods of determining the efficacy of a therapeutic compound by measuring and comparing the molecular flux rates of the two or more biological molecules in a first population in need of the compound, administering the compound to the same population or to a second population of one or more tissues or individuals, and measuring and comparing the molecular flux rates of the two or more biological molecules in the same population after administration of the compound or in the second population of one or more tissues or individuals. A difference in the relative molecular flux rates of the first population before and after administration of the compound or between the first population and the second population measures the effectiveness of the therapeutic agent in tissues or individuals in need of the compound.

The invention also includes methods of determining the efficacy of a therapeutic compound by measuring and comparing the molecular flux rates of the two or more biological molecules in a population of one or more tissues or individuals in need of the compound, administering the compound to the same population of one or more tissues or individuals, and measuring and comparing the molecular flux rates of the two or more biological molecules in the population after administration of the compound. A difference in the relative molecular flux rates of the population before and after administration of the compound measures the effectiveness of the compound in tissues or individuals in need of the compound.

A tumoricidal or tumor static effect of a chemotherapeutic agent may be determined by measuring and comparing the relative molecular flux rates of cellular protein and cellular DNA. If the relative molecular flux rates of the protein and DNA do not change in individuals treated with the chemotherapeutic agent, the agent has a tumoricidal effect. However, if the molecular flux rate of the DNA is altered more than the molecular flux rate of the protein, the chemotherapeutic agent has a tumor static effect (i.e., the cells are not dead, but are continuing to synthesize protein, although they are not dividing). The tumoricidal or tumor static effect of a chemotherapeutic agent may be determined by measuring and comparing the relative molecular flux rates of cellular protein and cellular DNA in treated and untreated populations, or in a single population before and after treatment with the chemotherapeutic agent.

A therapeutic effect of an androgen or other anabolic therapy may be determined in one or more tissues or individuals with a wasting or frailty disease or disorder by comparing the relative molecular flux rates of either muscle protein or muscle DNA to that of adipose tissue triglyceride. If the molecular synthesis rate of the muscle protein or muscle DNA increases relative to adipose tissue triglyceride, the androgen has a therapeutic effect in the wasting or frailty disease or disorder. A therapeutic effect of a growth hormone in a wasting or frailty disease or disorder may also be determined in a like manner.

In another aspect, a therapeutic effect of a selective estrogen receptor modulator (SERM) in breast cancer therapy may be determined in one or more tissues or individuals by measuring and comparing the relative molecular flux rates of mammary epithelial cell DNA or endometrial cell DNA and breast stromal tissue protein or lipid synthesis. If the molecular synthesis rate of the mammary epithelial cell DNA or endometrial cell DNA decreases relative to the molecular synthesis rate of the breast stromal tissue protein or lipid molecules, the SERM has a therapeutic effect against breast cell proliferation.

A therapeutic effect of a SERM in osteoporosis may be determined in one or more tissues or individuals by measuring and comparing the relative molecular flux rates of bone collagen and breast or endometrial cell DNA synthesis. An increase in the molecular flux rate of bone collagen relative to the molecular flux rate of breast or endothelial DNA synthesis indicates a therapeutic effect of the SERM against osteoporosis relative to its potential adverse effects on breast or endometrial cancer risk.

A therapeutic effect of a compound in Alzheimer's disease may be determined in one or more tissues or individuals by measuring and comparing the relative molecular flux rates of brain amyloid-beta (Aβ) protein or amyloid precursor protein and a reference molecule in the cerebrospinal fluid (CSF). A decrease in the molecular flux rate of brain Aβ protein relative to the molecular flux rate of the CSF reference molecule (e.g., a constitutive lipid in the CSF) indicates a therapeutic effect of the compound against Alzheimer's disease. Alternatively, a therapeutic effect of a compound in Alzheimer's disease may be determined in one or more tissues or individuals by measuring and comparing the relative molecular flux rates of Aβ protein and/or amyloid precursor protein (APP), neuron DNA, and/or microglia DNA to untreated tissues or individuals or to tissues or individuals without disease (i.e., "controls"). Optionally, the molecular flux rate of galactocerebroside (either brain or plasma) may also be measured. A difference in the flux (or fluxes) of one or more of Aβ, APP, neuron DNA, microglia DNA, and galactocerebroside (or any combinations thereof) in a diseased tissue or individual (e.g., an appropriate animal model of disease) when compared to controls indicates a therapeutic effect of the compound against Alzheimer's disease.

A therapeutic effect of a compound in neuroinflammation may be determined in one or more tissues or individuals by measuring and comparing the relative molecular flux rates of neuron DNA, microglia DNA, and/or galactocerebroside (either brain or plasma) to untreated tissues or individuals or to tissues or individuals without disease (i.e., "controls"). Optionally, the molecular flux rates of one or more inflammatory proteins such as interleukin-6 and/or interleukin-12 and/or glial fibrillary acidic protein (GFAP) and/or S100B (glial calcium signaling protein) may also be measured. A difference in the flux (or fluxes) of one or more of neuron DNA, microglia DNA, galactocerebroside, interleukin-6, interleukin-12, GFAP, and S100B (or any combinations thereof) in a diseased tissue or individual (e.g., an appropriate animal model of disease) when compared to controls indicates a therapeutic effect of the compound against neuroinflammation.

A therapeutic effect of a compound in psoriasis may be determined in one or more tissues or individuals by measuring and comparing the relative molecular flux rates of keratinocyte DNA and skin keratin to untreated tissues or individuals or to tissues or individuals without disease (i.e., "controls"). A difference in the flux (or fluxes) of keratinocyte DNA and/or skin keratin in a diseased tissue or individual (e.g., an appropriate animal model of disease) when compared to controls indicates a therapeutic effect of the compound against psoriasis.

A therapeutic effect of a compound in liver disease (e.g., liver fibrosis, cirrhosis, acute toxicity due to exposure to a chemical or microorganism, or other disease) may be determined in one or more tissues or individuals by measuring and comparing the relative molecular flux rates of total liver cell DNA or hepatocyte DNA and liver collagen to untreated tissues or individuals or to tissues or individuals without disease (i.e., "controls"). A difference in the flux (or fluxes) of total liver cell DNA or hepatocyte DNA and liver collagen in a diseased tissue or individual (e.g., an appropriate animal model of disease) when compared to controls indicates a therapeutic effect of the compound against liver disease.

An anti-angiogenic effect of a compound may be determined in one or more tissues or individuals by measuring and comparing the relative molecular flux rates of endothelial cell DNA and tumor cell DNA. Optionally, the relative molecular flux rates of other tissue endothelial cell DNA and tissue DNA may be measured, such as liver endothelial cell DNA and total liver cell DNA. A decrease in the fluxes of tumor endothelial cell DNA and tumor cell DNA when compared to untreated tissues or individuals indicates an anti-angiogenic effect of the compound that possesses a tumoricidal effect. A decrease in the flux of tumor endothelial cell DNA and an inhibition of an increase in flux of tumor cell DNA when compared to untreated tissues or individuals indicates an anti-angiogenic effect of the compound and a tumoristatic effect of the compound. A decrease in the flux of tumor endothelial cell DNA and a lack of effect on flux of tumor cell DNA when compared to untreated tissues or individuals indicates anti-angiogenic activity but a lack of effect on tumor cells. A difference in the flux (or fluxes) of tumor endothelial cell DNA and tumor cell DNA when compared to other tissue endothelial cell DNA and other tissue DNA is an alternative way of determining an anti-angiogenic effect of the compound.

The response of muscle tissue to aerobic exercise in an individual may be measured by measuring and comparing the relative molecular flux rates of cellular proteins and mitochondrial DNA in muscle tissue. An increase in the molecular flux rate of mitochondrial DNA relative to cellular proteins in individuals subjected to aerobic exercise identifies increased aerobic fitness.

The cause of a change in protein expression based on either transcriptional control or translational control may be identified by measuring and comparing the relative molecular flux rates of a protein and an mRNA encoding the protein at two or more timepoints. An increase in the molecular flux rate of the protein relative to the mRNA identifies a change in translational control, whereas a stable or decreased molecular flux rate of the protein relative to the mRNA identifies a change in transcriptional control.

The cause of a change in total mass or protein expression in an individual may be identified by measuring and comparing the relative molecular flux rate of total cellular RNA and total cellular DNA at two or more timepoints. An increase in the molecular flux rate of mRNA relative to the molecular flux rate of DNA identifies transcription as the cause of a change in total mass or protein expression, while no change or a decrease in the molecular flux rate of total cellular mRNA relative to the molecular flux rate of total cellular DNA identifies a change in cell division as the cause of a change in total mass or protein expression.

A therapeutic property of a biological agent may be identified by measuring and comparing the molecular flux rates of two or more biological molecules in a first population of one or more tissues or individuals, administering the biological agent to a second population of one or more tissues or individuals, and comparing the relative molecular flux rates of the two or more biological molecules in the two populations. A difference in the compared molecular flux rates between the two populations identifies a therapeutic property of the biological agent.

Alternatively, a therapeutic property of a biological agent may be identified by measuring and comparing the molecular flux rates of two or more biological molecules in a population of one or more tissues or individuals, administering the biological agent to the population, and comparing the relative molecular flux rates of the two or more biological molecules before and after the biological agent is administered. A difference in the compared molecular flux rates before and after the biological agent is administered identifies a therapeutic property of the biological agent.

The biological agent may be any biological agent. The one or more biological samples containing the biological molecules may be tissue cultures, or may be obtained from experimental animals or humans. In one variation, at least one of the biological molecules is DNA. In another variation, at least one of the biological molecules is a protein.

Toxic effects of a biological agent may be determined by measuring and comparing the molecular flux rates of two or more biological molecules in a first population of one or more tissues or individuals, administering the biological agent to a second population of one or more tissues or individuals, and measuring and comparing the relative molecular flux rates of the two or more biological molecules in the second population compared to the first population. A difference in the compared molecular flux rates between the first population and the second population identifies a toxic effect of the biological agent.

Alternatively, toxic effects of a biological agent may be determined by measuring and comparing the molecular flux rates of two or more biological molecules in a population of one or more tissues or individuals, administering the biological agent to the population, and measuring and comparing the relative molecular flux rates of the two or more biological molecules before and after administration. A difference in the compared molecular flux rates before and after administration of the biological agent identifies a toxic effect of the biological agent.

Toxic effects of a xenobiotic (such as a new chemical entity, drug, drug candidate, drug lead, a biological agent, an environmental chemical, food additive, industrial chemical, or cosmetic, or combinations or mixtures thereof) may be determined by measuring and comparing the molecular flux rates of two or more biological molecules in a first population of one or more tissues or individuals (such as experimental animals or humans), administering the xenobiotic (or combination of xenobiotics or mixtures of xenobiotics) to a second population of one or more tissues or individuals, and measuring and comparing the relative molecular flux rates of the two or more biological molecules in the second population compared to the first population. A difference in the compared molecular flux rates between the first population and the second population identifies a toxic effect of the xenobiotic (or combination of xenobiotics or mixtures of xenobiotics).

Alternatively, toxic effects of a xenobiotic may be determined by measuring and comparing the molecular flux rates of two or more biological molecules in a population of one or more tissues or individuals, administering the xenobiotic (or combination of xenobiotics or mixtures of xenobiotics) to the population, and measuring and comparing the relative molecular flux rates of the two or more biological molecules before and after administration. A difference in the compared molecular flux rates before and after administration of the xenobiotic (or combination of xenobiotics or mixtures of xeniobiotics) identifies a toxic effect of the xenobiotic (or combinations of xenobiotics or mixtures of xenobiotics).

In addition, the methods disclosed herein may be used to identify one or more therapeutic targets. The molecular flux rates of two or more biological molecules are measured and compared in a first population of one or more tissues or individuals. A drug or drug candidate or drug lead or new chemical entity or biological agent or already-approved drug (or any combinations or mixtures thereof) is given to a second population of one or more tissues or individuals, and the relative molecular flux rates of the two or more biological molecules in the second population are compared to the first population. A difference in the compared molecular flux rates between the first population and the second population identifies a therapeutic target.

Alternatively, the methods disclosed herein may be used to identify one or more therapeutic targets by measuring and comparing two or more biological molecules in a first population of one or more tissues or individuals, administering a drug or drug candidate or drug lead or new chemical entity or already-approved drug or biological agent (or combinations or mixtures thereof) to the population, and measuring and comparing the relative molecular flux rates of the two or more biological molecules before and after administration of the drug or drug candidate or drug lead. A difference in the compared molecular flux rates before and after administration identifies a drug target.

All methods disclosed herein are easily adaptable to high-throughput methods. A plurality of diseases and disorders, therapeutic compounds (including drugs, drug candidates, drug leads, new chemical entities, already-approved drugs or biological agents including any combinations or mixtures thereof), xenobiotics, and therapeutic targets may be screened.

The invention also includes kits for analyzing, measuring, and/or comparing the relative molecular flux rates of two or more biological molecules. In one aspect, the kits include isotope-labeled water, and one or more tools for administering isotope-labeled water to a tissue or individual. In another aspect, the kits include chemical compounds or reagents for separating, partially purifying, or isolating biological molecules from biological samples. The kit may also include an instrument for collecting a sample from an individual.

The invention also includes isotopically perturbed molecules, said isotopically perturbed molecules comprising one or more stable isotopes. The isotopically perturbed molecules are products of the labeling methods described herein. The isotopically perturbed molecules are collected by sampling techniques known in the art and are analyzed using appropriate analytical tools.

The invention also provides isotopically perturbed molecules labeled with one or more radioactive isotopes.

The invention also provides one or more therapeutic agents identified and at least partially characterized by the methods of the present invention.

BRIEF DESCRIPTION OF THE FIGURES

FIG. 16 shows that only the high dose of $CCl_4$ increased liver collagen synthesis whereas the low dose of $CCl_4$, which increased total liver cell proliferation, had no effect on liver collagen synthesis relative to vehicle control.

FIG. 17 shows increased liver cell proliferation, in a dose-dependent manner, relative to controls. The lowest dose of griseofulvin had an observable effect on liver cell proliferation. Liver collagen synthesis was measured concurrently with liver cell proliferation. Unlike $CCl_4$ (FIG. 16, supra), griseofulvin had no effect on liver collagen synthesis at the doses tested (data not shown).

DETAILED DESCRIPTION OF THE INVENTION

Figure 1A:
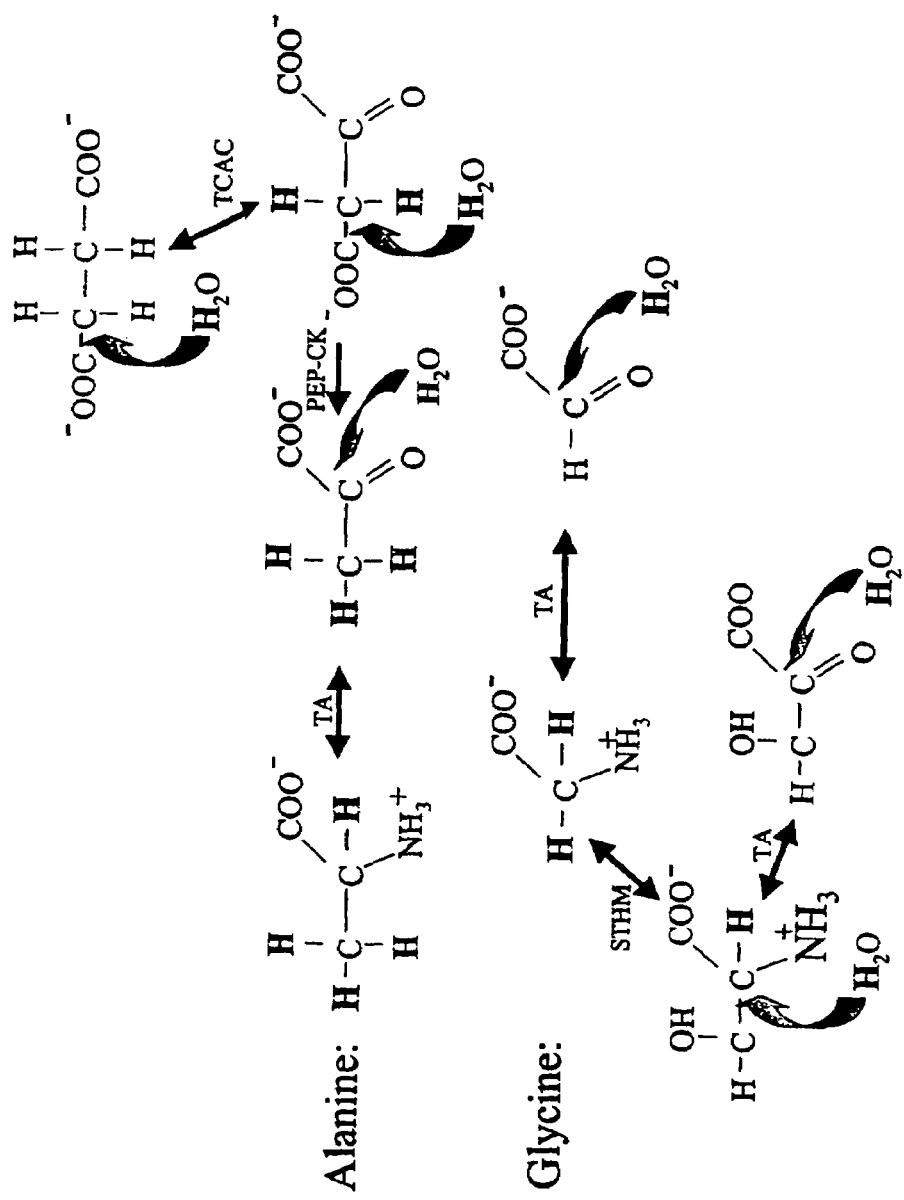
FIGS. 1A–B depicts pathways of labeled hydrogen exchange from isotope-labeled water into selected free amino acids. Two NEAA's (alanine, glycine) and an EAA (leucine) are shown, by way of example. Alanine and glycine are presented in FIG. 2A. Leucine is presented in FIG. 2B. Abbreviations: TA, transaminase; PEP-CK, phosphoenol-pyruvate carboxykinase; TCAC, tricarboxylic acid cycle; STHM, serine tetrahydrofolate methyl transferase.

Applicants have discovered a method of measuring the relative molecular flux rates of different biological molecules, frequently in a variety of biochemical classes, through a single protocol. First, isotope-labeled water, a universal precursor, is administered to a tissue or individual. The molecular flux rates of two or more biological molecules even if the molecules are of different chemical classes may be determined simultaneously and from a single protocol.

I. General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, *Molecular Cloning: A Laboratory Manual*, second edition (Sambrook et al., 1989) Cold Spring Harbor Press; *Oligonucleotide Synthesis* (M. J. Gait, ed., 1984); *Methods in Molecular Biology, Humana Press; Cell Biology: A Laboratory Notebook* (J. E. Cellis, ed., 1998) Academic Press; *Animal Cell Culture* (R. I. Freshney, ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993–8) J. Wiley and Sons; *Methods in Enzymology* (Academic Press, Inc.); *Handbook of Experimental Immunology* (D. M. Weir and C. C. Blackwell, eds.); *Gene Transfer Vectors for Mammalian Cells* (J. M. Miller and M. P. Calos, eds., 1987); *Current Protocols in Molecular Biology* (F. M. Ausubel et al., eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Wiley and Sons, 1999); and *Mass isotopomer distribution analysis at eight years: theoretical, analytic and experimental considerations* by Hellerstein and Neese (*Am J Physiol* 276 (*Endocrinol Metab*. 39) E1146–E1162, 1999). Furthermore, procedures employing commercially available assay kits and reagents will typically be used according to manufacturer-defined protocols unless otherwise noted.

II. Definitions

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, *Mass isotopomer distribution analysis at eight years: theoretical, analytic and experimental considerations* by Hellerstein and Neese (*Am J Physiol* 276 (*Endocrinol Metab*. 39) E1146–E1162, 1999). As appropriate, procedures involving the use of commercially available kits and reagents are generally carried out in accordance with manufacturer defined protocols and/or parameters unless otherwise noted.

"Molecular flux rate" refers to the rate of synthesis or production and breakdown or removal of a biological molecule. "Molecular flux" therefore is synonymous with the flow into and out of a pool of molecules.

"Isotopomers" refer to isotopic isomers or species that have identical elemental compositions but are constitutionally and/or stereochemically isomeric because of isotopic substitution, for example $CH_3NH_2$, $CH_3NHD$ and $CH_2DNH_2$.

"Isotopologues" refer to isotopic homologues or molecular species that have identical elemental and chemical compositions but differ in isotopic content (e.g., $CH_3NH_2$ vs. $CH_3NHD$ in the example above). Isotopologues are defined by their isotopic composition, therefore each isotopologue has a unique exact mass but may not have a unique structure. An isotopologue is usually comprised of a family of isotopic isomers (isotopomers) which differ by the location of the isotopes on the molecule (e.g., $CH_3NHD$ and $CH_2DNH_2$ are the same isotopologue but are different isotopomers).

"Mass isotopomer" refers to a family of isotopic isomers that are grouped on the basis of nominal mass rather than isotopic composition. A mass isotopomer may include molecules of different isotopic compositions, unlike, an isotopologue (e.g., $CH_3NHD$, $^{13}CH_3NH_2$, $CH_3{}^{15}NH_2$ are part of the same mass isotopomer but are different isotopologues). In operational terms, a mass isotopomer is a family of isotopologues that are not resolved by a mass spectrometer. For quadrupole mass spectrometers, this typically means that mass isotopomers are families of isotopologues that share a nominal mass. Thus, the isotopologues $CH_3NH_2$ and $CH_3NHD$ differ in nominal mass and are distinguished as being different mass isotopomers, but the isotopologues $CH_3NHD$, $CH_2DNH_2$, $^{13}CH_3NH_2$, and $CH_3{}^{15}NH_2$ are all of the same nominal mass and hence are the same mass isotopomers. Each mass isotopomer is therefore typically composed of more than one isotopologue and has more than one exact mass. The distinction between isotopologues and mass isotopomers is useful in practice because all individual isotopologues are not resolved using quadrupole mass spectrometers and may not be resolved even using mass spectrometers that produce higher mass resolution, so that calculations from mass spectrometric data must be performed on the abundances of mass isotopomers rather than isotopologues. The mass isotopomer lowest in mass is represented as $M_0$; for most organic molecules, this is the species containing all $^{12}C$, $^1H$, $^{16}O$, $^{14}N$, etc. Other mass isotopomers are distinguished by their mass differences from $M_0$ ($M_1$, $M_2$, etc.). For a given mass isotopomer, the location or position of isotopes within the molecule is not specified and may vary (i.e., "positional isotopomers" are not distinguished).

"Mass isotopomer pattern" refers to a histogram of the abundances of the mass isotopomers of a molecule. Traditionally, the pattern is presented as percent relative abundances where all of the abundances are normalized to that of the most abundant mass isotopomer; the most abundant isotopomer is 100%. The preferred form for applications involving probability analysis, however, is proportion or fractional abundance, where the fraction that each species contributes to the total abundance is used (see below). The term isotope pattern is sometimes used in place of mass isotopomer pattern, although technically the former term applies only to the abundance pattern of isotopes in an element.

An "individual" is a vertebrate, preferably a mammal, more preferably a human.

A "biological molecule" refers to any molecule or molecules synthesized in a tissue or individual. A biological molecule may refer to a class of molecules, such as, but not limited to, the set of total cellular proteins, genomic DNA, mitochondrial DNA, messenger RNA, or ribosomal RNA. Alternatively, biological molecules may be specific molecules with specific structural features or sequences, such as specific proteins (for example, apolipoprotein) or specific polynucleotide sequences (for example, a polynucleotide encoding apolipoprotein).

As used herein, an individual "at risk" is an individual who is considered more likely to develop a disease state or a physiological state than an individual who is not at risk. An individual "at risk" may or may not have detectable symptoms indicative of the disease or physiological condition, and may or may not have displayed detectable disease prior to the treatment methods (e.g., therapeutic intervention) described herein. "At risk" denotes that an individual has one or more so-called risk factors. An individual having one or more of these risk factors has a higher probability of developing one or more disease(s) or physiological condition(s) than an individual without these risk factor(s). These risk factors can include, but are not limited to, history of family members developing one or more diseases, related conditions, or pathologies, history of previous disease, age, sex, race, diet, presence of precursor disease, genetic (i.e., hereditary) considerations, and environmental exposure.

"Isotope-labeled water" includes water labeled with one or more specific heavy isotopes of either hydrogen or oxygen. Specific examples of isotope-labeled water include $^2H_2O$, $^3H_2O$, and $H_2^{18}O$.

"Partially purifying" refers to methods of removing one or more components of a mixture of other similar compounds. For example, "partially purifying a protein or peptide" refers to removing one or more biological molecules from a mixture of one or more biological molecules.

"Isolating" refers to separating one compound from a mixture of compounds. For example, "isolating a protein or peptide" refers to separating one specific protein or peptide from all other biological molecules in a mixture of one or more biological molecules.

A "biological sample" encompasses any sample obtained from a tissue or individual. The definition encompasses blood and other liquid samples of biological origin, that are accessible from an individual through sampling by minimally invasive or non-invasive approaches (e.g., urine collection, blood drawing, needle aspiration, and other procedures involving minimal risk, discomfort or effort). The definition also includes samples that have been manipulated in any way after their procurement, such as by treatment with reagents, solubilization, or enrichment for certain components, such as proteins or polynucleotides. The term "biological sample" also encompasses a clinical sample such as serum, plasma, other biological fluid, or tissue samples, and also includes cells in culture, cell supernatants and cell lysates.

"Biological fluid" includes but is not limited to urine, blood, interstitial fluid, edema fluid, saliva, lacrimal fluid, inflammatory exudates, synovial fluid, abscess, empyema or other infected fluid, cerebrospinal fluid, sweat, pulmonary secretions (sputum), seminal fluid, feces, bile, intestinal secretions, or other biological fluid.

"Chemical entity" includes any molecule, chemical, or compound, whether new or known, that is administered to a living system for the purpose of screening it for biological or biochemical activity toward the goal of discovering potential therapeutic agents (drugs or drug candidates or drug leads) or uncovering toxic effects (industrial chemicals, pesticides, herbicides, food additives, cosmetics, and the like).

"Drug leads" or "drug candidates" are herein defined as chemical entities or biological molecules that are being evaluated as potential therapeutic agents (drugs). "Drug agents" or "agents or "compounds" are used interchangeably herein and describe any composition of matter (e.g., chemical entity or biological factor) that is administered, approved or under testing as potential therapeutic agent or is a known therapeutic agent.

"Known drugs" or "known drug agents" or "already-approved drugs" refers to agents (i.e., chemical entities or biological factors) that have been approved for therapeutic use as drugs in human beings or animals in the United States or other jurisdictions. In the context of the present invention, the term "already-approved drug" means a drug having approval for an indication distinct from an indication being tested for by use of the methods disclosed herein. Using psoriasis and fluoxetine as an example, the methods of the present invention allow one to test fluoxetine, a drug approved by the FDA (and other jurisdictions) for the treatment of depression, for effects on biomarkers of psoriasis (e.g., keratinocyte proliferation or keratin synthesis); treating psoriasis with fluoxetine is an indication not approved by FDA or other jurisdictions. In this manner, one can find new uses (in this example, anti-psoriatic effects) for an already-approved drug (in this example, fluoxetine).

"Biological factor" refers to a compound or compounds made by living organisms having biological or physiological activities (e.g., preventive, therapeutic and/or toxic effects). Examples of biological factors include, but are not limited to, vaccines, polyclonal or monoclonal antibodies, recombinant proteins, isolated proteins, soluble receptors, gene therapy products, and the like. As used herein, the term "biologics" is synonymous with "biological factor."

"Compound" means, in the context of the present invention, any new chemical entity, chemical entity, drug lead, drug candidate, drug, drug agent, therapeutic agent, agent, known drug, known drug agent, already-approved drug, biologic, or biological factor.

By "therapeutic target" is meant a site (e.g., a molecule within one or more metabolic pathways) within or on the body that mediates, or is thought to mediate, changes in physiology that are associated with a medical disease or condition. In many cases, a therapeutic target is unknown and the methods of the present invention allow for the discovery of one or more therapeutic targets, for example by administering one or more compounds to a tissue or individual or a population of tissues or individuals and determining changes in molecular flux rates as is more fully described, infra.

III. Methods of the Invention

The inventor has discovered that isotope-labeled water is a universal precursor for essentially all biological molecules, especially in different chemical classes, synthesized in tissues and individuals. Introducing isotope-labeled water to a tissue or individual therefore results in the incorporation of isotope labels into biological molecules of the tissue or individual. The relative molecular flux rates of multiple biological molecules may be measured and compared. An exemplary, but not limiting list of biological molecules is provided in Table 1. Examples of biochemical processes that can be measured are provided in Table 2.

The present application is thus directed to a method of measuring and comparing the relative molecular flux rates of two or more biological molecules in an individual by a) administering isotope-labeled water to an individual for a period of time sufficient for the label to be incorporated into two or more biological molecules to form two or more isotope-labeled biological molecules, even if the two or more biological molecules are of different chemical classes; b) obtaining one or more biological samples from a tissue or individual, wherein the one or more biological samples contain two or more of the isotope-labeled biological molecules; c) measuring the incorporation of the label in the two or more biological molecules to determine the molecular flux rates of the biological molecules; and d) comparing the molecular flux rates of the biological molecules to analyze the relative molecular flux rates.

A. Administering Isotope-labeled Water to One or More Tissues or Individuals (1) Theory of $^2$H, $^3$H, or $^{18}$O-isotope-labeled Water Incorporation $H_2O$ availability is probably never limiting for biosynthetic reactions in a cell (because $H_2O$ represents close to 70% of the content of cells, or >35 Molar concentration), but hydrogen and oxygen atoms from $H_2O$ contribute stoichiometrically to many reactions involved in biosynthetic pathways:

e.g.,: R—CO—CH$_2$—COOH+NADPH+H$_2$O→R—CH$_2$CH$_2$COOH (fatty acid synthesis).

As a consequence, isotope labels provided in the form of H— or O-isotope-labeled water is incorporated into biological molecules as part of synthetic pathways. Hydrogen incorporation can occur in two ways: into labile positions in a molecule (i.e., rapidly exchangeable, not requiring enzyme catalyzed reactions) or into stable positions (i.e., not rapidly exchangeable, requiring enzyme catalysis). Oxygen incorporation occurs in stable positions.

Some of the hydrogen-incorporating steps from cellular water into C—H bonds in biological molecules only occur during well-defined enzyme-catalyzed steps in the biosynthetic reaction sequence, and are not labile (exchangeable with solvent water in the tissue) once present in the mature end-product molecules. For example, the C—H bonds on glucose are not exchangeable in solution. In contrast, each of the following C—H positions exchanges with body water during reversal of specific enzymatic reactions: C-1 and C-6, in the oxaloacetate/succinate sequence in the Krebs' cycle and in the lactate/pyruvate reaction; C-2, in the glucose-6-phosphate/fructose-6-phosphate reaction; C-3 and C-4, in the glyceraldehyde-3-phosphate/dihydroxyacetone-phosphate reaction; C-5, in the 3-phosphoglycerate/glyceraldehyde-3-phosphate and glucose-6-phosphate/fructose-6-phosphate reactions (Katz 1976).

Labeled hydrogen or oxygen atoms from water that are covalently incorporated into specific non-labile positions of a molecule thereby reveals the molecule's "biosynthetic history"—i.e., label incorporation signifies that the molecule was synthesized during the period that isotope-labeled water was present in cellular water.

The labile hydrogens (non-covalently associated or present in exchangeable covalent bonds) in these biological molecules do not reveal the molecule's biosynthetic history. Labile hydrogen atoms can be easily removed by incubation with unlabelled water ($H_2O$) (i.e., by reversal of the same non-enzymatic exchange reactions through which $^2$H or $^3$H was incorporated in the first place), however:

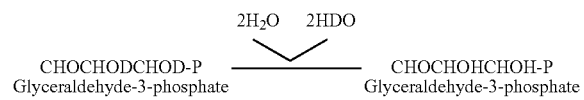

CHOCHODCHOD-P ⇌ CHOCHOHCHOH-P
Glyceraldehyde-3-phosphate    Glyceraldehyde-3-phosphate As a consequence, potentially contaminating hydrogen label that does not reflect biosynthetic history, but is incorporated via non-synthetic exchange reactions, can easily be removed in practice by incubation with natural abundance $H_2O$.

Analytic methods are available for measuring quantitatively the incorporation of labeled hydrogen atoms into biological molecules (e.g., liquid scintillation counting for $^3$H; mass spectrometry or NMR spectroscopy for $^2$H and $^{18}$O). For further discussions on the theory of isotope-labeled water incorporation, see, for example, Jungas 1968, incorporated herein by reference.

(2) Incorporation of Isotopes from Isotope-labeled Water into Biological Molecules Isotope-labeled water may be administered via continuous isotope-labeled water administration, discontinuous isotope-labeled water administration, or after single or multiple administration of isotope-labeled water administration. In continuous isotope-labeled water administration, isotope-labeled water is administered to an individual for a period of time sufficient to maintain relatively constant water enrichments over time in the individual. For continuous methods, labeled water is optimally administered for a period of sufficient duration to achieve a steady state concentration (e.g., 3–8 weeks in humans, 1–2 weeks in rodents).

In discontinuous isotope-labeled water administration, an amount of isotope-labeled water is measured and then administered, one or more times, and then the exposure to isotope-labeled water is discontinued and wash-out of isotope-labeled water from the body water pool is allowed to occur. The time course of delabeling may then be monitored. Water is optimally administered for a period of sufficient duration to achieve detectable levels in biological molecules.

Isotope-labeled water may be administered to an individual or tissue in various ways known in the art. For example, isotope-labeled water is administered orally, parenterally, subcutaneously, intravascularly (e.g., intraarterially or intravenously), or intraperitoneally. Several commercial sources of $^2H_2O$ and $H_2{}^{18}O$ are available, including Isotec, Inc. (Miamisburg Ohio, and Cambridge Isotopes, Inc. (Andover, Mass.). The isotopic content of isotope labeled water that is administered can range from about 0.001% to about 20% and depends upon the analytic sensitivity of the instrument used to measure the isotopic content of the biological molecules. For oral administration, 4% $^2H_2O$ in drinking water is administered. For human administration, 50 mL $^2H_2O$ is administered.

Biological Molecules

Isotope labels from isotope labeled water are incorporated into virtually all biological molecules synthesized in a tissue or individual. Examples of biological molecules include, but are not limited to, proteins (such as specific proteins, total cellular proteins, apolipoprotein, immunoglobulins, collagen, elastin, and keratin), polynucleotides (such as specific DNA or RNA sequences, total cellular DNA, genomic DNA, mitochondrial DNA, total cellular RNA, messenger RNA, ribosomal RNA, transfer RNA), lipids and lipid synthesis components (such as cholesterol, cholesterol ester, triglycerides, fatty acids, and acyl-glycerides), carbohydrates, glycosaminoglycans, proteoglycans, and combinations or polymers thereof. The biological molecules may be those of the tissue or individual, or of an organism contained within the tissue or individual, such as bacteria. Some exemplary, non-limiting examples of biological molecules are depicted in Table 1.

TABLE 1

Exemplary Biomolecules for Which Molecular Flux Rates Can Be Measured by the Methods of the Invention

| Class | Examples |
|---|---|
| I) Lipids and derivatives | |
| Acylglycerides | Triglycerides |
| | Phospholipids |
| | Cardiolipin |
| Fatty acids | Palmitate |
| | Arachidonic acid |
| Sterols | Cholesterol |
| | Bile acids |
| | Estrogen, testosterone |
| | Glucocorticoids |
| Ceramides | Sphingomyelin |
| | Galactocerebroside |
| II) Carbohydrates and derivatives | |
| Monosaccharides | Glucose |
| | Galactose |
| Amino sugars | N-Acetyl-Galactosamine |
| Polysaccharides | Glycogen |
| Glycoproteins | Sialic acid |
| Glycolipids | Galactocerebrosides |
| Glycosaminoglycans | Hyaluronic acid |
| | Chondroitin-sulfate |
| | Heparan-sulfate |
| III) Proteins, peptides and amino acids | |
| Structural proteins | Collagen |
| | Myosin |

TABLE 1-continued

Exemplary Biomolecules for Which Molecular Flux Rates Can Be Measured by the Methods of the Invention

| Class | Examples |
|---|---|
| Secreted proteins | Albumin |
| | Apolipoprotein B |
| | Insulin |
| | Immunoglobulins |
| | Prostate-specific antigen |
| | Fibrinogen |
| | Interleukin-2 |
| Secreted or excreted peptides | N-terminal collagen telopeptides |
| | Glutathione |
| | Pyridinolines |
| Membrane proteins | Preadipocyte factor-1 |
| | Histocompatibility antigens |
| | T-cell receptors |
| Modified amino acids | Hydroxyproline |
| | 3-Methyl-histidine |
| Intracellular proteins | Creatine |
| Enzymes | Cytochrome C oxidase |
| Transporters | Glut-4 |
| Transcription factors | PPAR-γ |
| IV) Nucleic acids | |
| Deoxyribonucleotides | Genomic DNA |
| | Mitochondrial DNA |
| | Viral or bacterial DNA |
| Ribonucleotides | Messenger RNA |
| | Ribosomal RNA |
| Free nucleosides/nucleotides | Deoxyadenosine |
| | Deoxythymidine |
| | Adenosine-triphosphate |
| Purine and pyrimidine bases | Cytidine |
| | Adenine |
| Metabolic products of bases | Uric acid |
| Oligonucleotides | ALU sequences |
| | 8-oxo-guanidine |
| | Methyl-deoxycytosine |

TABLE 2

Examples of Biochemical Processes that Can Be Measured (and Relevant Diseases) to Screen for Actions in Biological Systems

| Process | Disease |
|---|---|
| I) DNA replication (cell division) | |
| Hepatocytes | Hepatitis; hepatic necrosis |
| Lymphocytes (including antigen-specific T-cells) | AIDS; vaccination |
| Spermatocytes | Male infertility |
| Colonocytes | Colon cancer and colitis |
| Mammary epithelial cells | Breast cancer |
| Renal tubular cells | Nephrotoxins |
| Prostate epithelial cells | Prostate cancer; BPH |
| Tumor cells | Cancer, leukemia |
| Vascular smooth muscle cells | Atherosclerosis |

TABLE 2-continued

Examples of Biochemical Processes that Can Be Measured
(and Relevant Diseases) to Screen for Actions in Biological Systems

| Process | Disease |
| --- | --- |
| Mitochondria | Metabolic fitness; mitochondrial diseases |
| Pancreatic β-cells | Type 2 diabetes |
| Bone marrow progenitor cells | Bone marrow failure |
| Keratinocytes | Psoriasis |
| Endometrial cells | Endometrial cancer |
| Endothelial cells | Angiogenesis |
| II) Fibrogenesis and bone deposition | |
| Liver collagen synthesis | Liver fibrosis; cirrhosis |
| Lung collagen synthesis | Pulmonary fibrosis |
| Cardiac collagen synthesis | Heart failure |
| Renal collagen synthesis | Renal fibrosis |
| Dermal collagen synthesis | Scleroderma |
| Bone collagen synthesis | Osteoporosis; Paget's Disease |
| Cartilage collagen synthesis | Osteoarthritis |
| III) Lipid synthesis and breakdown | |
| Adipose tissue triglycerides | Obesity; Lipodystrophy |
| Serum cholesterol | Hyperlipidemia |
| Brain myelination and demyelination | Multiple Sclerosis |
| Mitochondrial phospholipids | Metabolic fitness |
| Sterols | Gall bladder disease; dyslipidemia; hormonal disorders |
| IV) Tissue glycosaminoglycans | |
| Synovial fluid hyaluronic acid | Osteoarthritis; rheumatoid arthritis |
| Synovial fluid chondroitin-sulfate | Osteoarthritis; rheumatoid arthritis |
| Cartilage hyaluronic acid and chondroitin-sulfate | Osteoarthritis; rheumatoid arthritis |
| Tumor hyaluronic acid | Metastatic potential |
| V) Protein synthesis (general) | |
| Immunoglobulins | Multiple myeloma; vaccination |
| Albumin | Malnutrition |
| Apolipoprotein B or E | Hyperlipidemia |
| Muscle myosin | Frailty |
| Skin keratin | Psoriasis |
| Amyloid-β | Alzheimer's disease |
| Viral or bacterial proteins | Infectious diseases |
| Insulin | Diabetes mellitus |
| Interleukins and cytokines | Inflammation |
| Hair proteins | Hirsutism; baldness |
| Histocompatibility proteins | Transplantation |
| Hemoglobin | Anemias |
| Histones | Gene regulation |
| Fibrinogen | Clotting disorders |
| VI) Carbohydrate synthesis | |
| Blood glucose | Diabetes mellitus |
| Galacto-cerebrosides | Multiple Sclerosis |
| Advanced glycosylation products | Diabetic complications |
| Tissue glycogen | Insulin resistance |

Proteins as Biological Molecules

In one embodiment, isotope labels from isotope-labeled water may be incorporated into proteins. The hydrogen atoms on C—H bonds are the hydrogen atoms on amino acids that are useful for measuring protein synthesis from $^2H_2O$ since the O—H and N—H bonds of peptides and proteins are labile in aqueous solution. As such, the exchange of $^2H$-label from $^2H_2O$ into O—H or N—H bonds occurs without the synthesis of proteins from free amino acids as described above. C—H bonds undergo incorporation from $H_2O$ into free amino acids during specific enzyme-catalyzed intermediary metabolic reactions (FIG. 1). The presence of $^2H$-label in C—H bonds of protein-bound amino acids after $^2H_2O$ administration therefore means that the protein was assembled from amino acids that were in the free form during the period of $^2H_2O$ exposure—i.e., that the protein is newly synthesized. Analytically, the amino acid derivative used must contain all the C—H bonds but must remove all potentially contaminating N—H and O—H bonds.

Figure 1B:
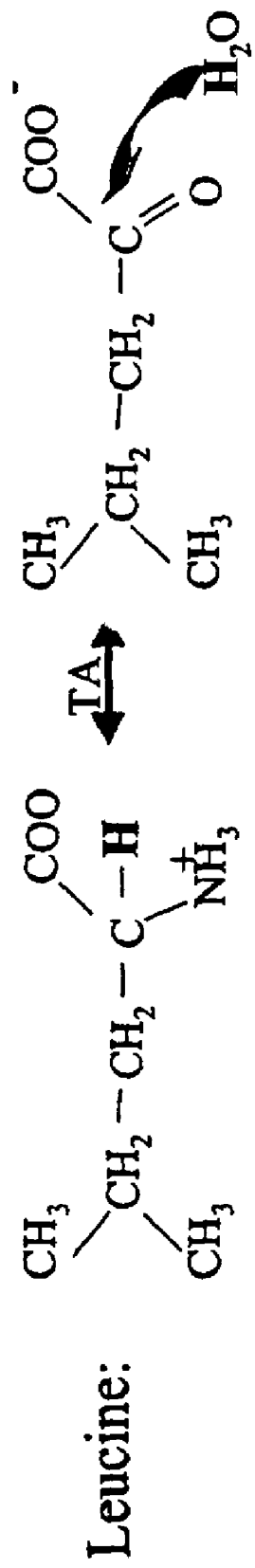

Hydrogen atoms from body water may be incorporated into free amino acids. $^2H$ or $^3H$ from isotope-labeled water can enter into free amino acids in the cell through the reactions of intermediary metabolism, but $^2H$ or $^3H$ cannot enter into amino acids that are present in peptide bonds or that are bound to transfer RNA. Free essential amino acids may incorporate a single hydrogen atom from body water into the α-carbon C—H bond, through rapidly reversible transamination reactions (FIG. 1). Free non-essential amino acids contain a larger number of metabolically exchangeable C—H bonds, of course, and are therefore expected to exhibit higher isotopic enrichment values per molecule from $^2H_2O$ in newly synthesized proteins (FIG. 1A–B).

One of skill in the art will recognize that labeled hydrogen atoms from body water may be incorporated into other amino acids via other biochemical pathways. For example, it is known in the art that hydrogen atoms from water may be incorporated into glutamate via synthesis of the precursor α-ketoglutarate in the citric acid cycle. Glutamate, in turn, is known to be the biochemical precursor for glutamine, proline, and arginine. By way of another example, hydrogen atoms from body water may be incorporated into post-translationally modified amino acids, such as the methyl group in 3-methyl-histidine, the hydroxyl group in hydroxyproline or hydroxylysine, and others. Other amino acid synthesis pathways are known to those of skill in the art.

Figure 1C:
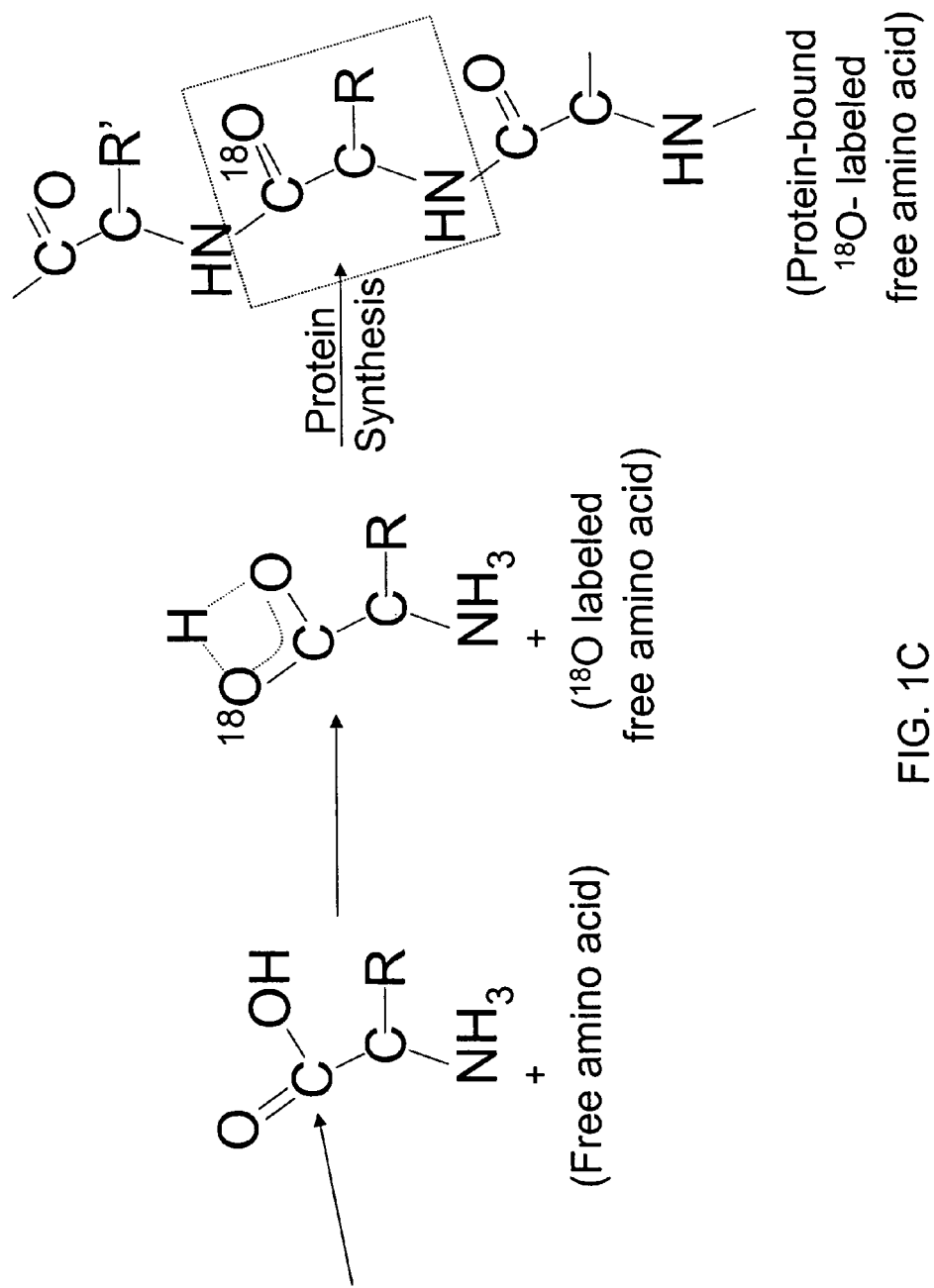
FIG. 1C depicts $^{18}O$-labeling of free amino acids by $H_2^{18}O$ for protein synthesis.

Oxygen atoms ($H_2^{18}O$) may also be incorporated into amino acids through enzyme-catalyzed reactions. For example, oxygen exchange into the carboxylic acid moiety of amino acids may occur during enzyme catalyzed reactions. Incorporation of labeled oxygen into amino acids is known to one of skill in the art as illustrated in FIG. 1C. Oxygen atoms may also be incorporated into amino acids from $^{18}O_2$ through enzyme catalyzed reactions (including hydroxyproline, hydroxylysine or other post-translationally modified amino acids).

Hydrogen and oxygen labels from isotope-labeled water may also be incorporated into amino acids through post-translational modifications. In one embodiment, the post-translational modification may already include labeled hydrogen or oxygen through biosynthetic pathways prior to post-translational modification. In another embodiment, the post-translational modification may incorporate labeled hydrogen, oxygen, carbon, or nitrogen from metabolic derivatives involved in the free exchange labeled hydrogens from body water, either before or after post-translational modification step (e.g., methylation, hydroxylation, phosphorylation, prenylation, sulfation, carboxylation, acetylation or other known post-translational modifications).

Hydrogen and oxygen labels from isotope-labeled water may be incorporated into amino acids, peptides, and proteins, such as those depicted in Table 1. The amino acids, peptides, and proteins listed in Table 1 are merely exemplary; the isotope labels may be incorporated into any amino acid, peptide, or protein.

Polynucleotides as Biological Molecules

Figure 2:
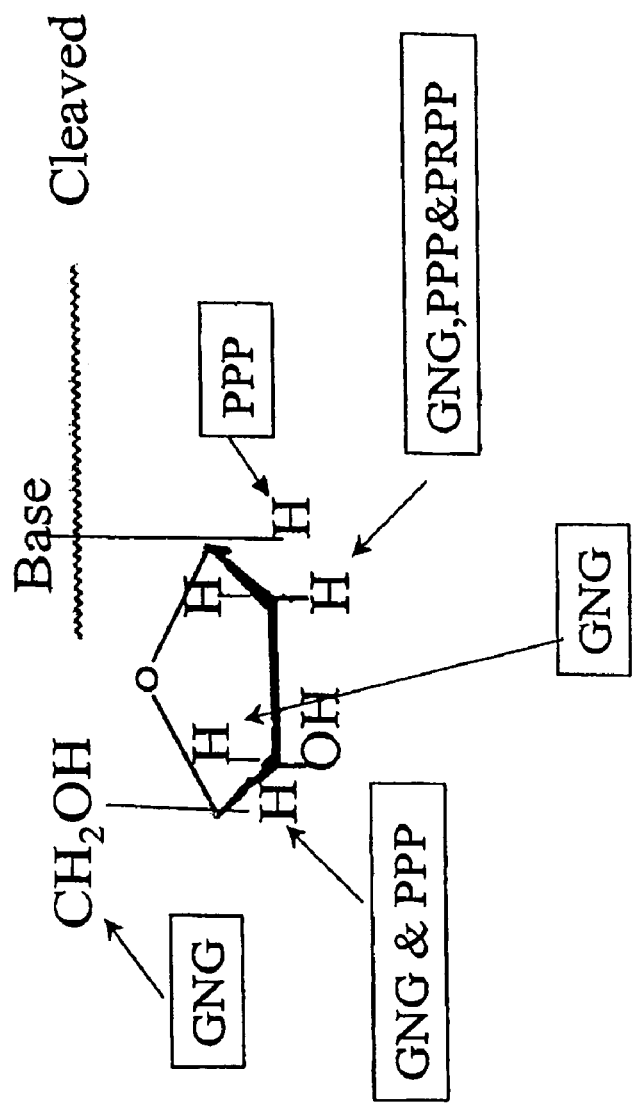
FIG. 2 depicts the incorporation of hydrogen isotopes, in this case deuterium from water into the deoxyribose (dR) of DNA.

Isotope labels from isotope-labeled water may also be incorporated into polynucleotides. (See, e.g., FIG. 2). Polynucleotides may be, but are not limited to, deoxyribonucleic acids (DNA), and ribonucleic acids (RNA), including messenger RNA (mRNA), ribosomal RNA (rRNA), transfer RNA (tRNA), and viral RNA. The polynucleotides may be from any source, including genomic DNA, mitochondrial DNA, and tissue RNA. Genomic DNA and nuclear DNA are used interchangeably herein.

The hydrogen atoms on C—H bonds of polynucleotides, polynucleosides, and nucleotide or nucleoside precursors may be used to measure polynucleotide synthesis from isotope-labeled water. C—H bonds undergo exchange from $H_2O$ into polynucleotide precursors. The presence of $^2H$-label in C—H bonds of polynucleotides, nucleosides, and nucleotide or nucleoside precursors after isotope-labeled water administration therefore means that the polynucleotide was synthesized during this period. The degree of labeling present may be determined experimentally, or assumed based on the number of labeling sites in a polynucleotide or nucleoside.

Hydrogen atoms from body water may be incorporated into free nucleosides or polynucleotides. $^2H$ or $^3H$ from isotope-labeled water can enter these molecules through the reactions of intermediary metabolism.

One of skill in the art will recognize that labeled hydrogen atoms from body water may be incorporated into other polynucleotides, nucleotides, or nucleosides via various biochemical pathways. For example, glycine, aspartate, glutamine, and tetrahydrofolate are known precursors of purine rings. Carbamyl phosphate and aspartate, for example, are known precursor molecules of pyrimidine rings. Ribose and ribose phosphate, and their synthesis pathways, are known precursors of polynucleotide synthesis.

Oxygen atoms ($H_2^{18}O$) may also be incorporated into polynucleotides, nucleotides, or nucleosides through enzyme-catalyzed biochemical reactions, including those listed above. Oxygen atoms from $^{18}H_2$ may also be incorporated into nucleotides by oxidative reactions, including non-enzymatic oxidation reactions (including oxidative damage, such as formation of 8-oxo-guanine and other oxidized bases or nucleotides).

Hydrogen and oxygen labels from isotope-labeled water may be incorporated into a nucleic acid or a component thereof, such as those depicted in Table 1. The nucleic acids and nucleic acid components listed in Table 1 are merely exemplary; the isotope labels may be incorporated into any nucleic acid or nucleic acid component.

Lipids and Lipid Constituents as Biological Molecules

Isotope labels from isotope-labeled water may also be incorporated into fatty acids, the glycerol moiety of acylglycerols (including but not limited to, triacylglycerides, phospholipids, and cardiolipin), cholesterol and its derivatives (including but not limited to cholesterol-esters, bile acids, steroid hormones) by biochemical pathways known in the art.

Complex lipids, such as glycolipids and cerebrosides, can also be labeled from isotope-labeled water, which is a precursor for the sugar-moiety of cerebrosides (including, but not limited to, N-acetylgalactosamine, N-acetylglucosamine-sulfate, glucuronic acid, and glucuronic acid-sulfate).

Isotopes from isotope-labeled water may also be incorporated into glycosaminoglycans and proteoglycans. For example, isotopes from isotope-labeled water may also be incorporated into the sugar moieties, including N-acetylglucosamine, N-acetylgalactosamine, glucuronic acid, the various sulfates of N-acetylglucosamine and N-acetylgalactosamine, galactose, iduronic acid, among others.

Hydrogen and oxygen labels from isotope-labeled water may be incorporated into lipid or lipid derivative, such as those depicted in Table 1. The lipids and lipid derivatives listed in Table 1 are merely exemplary; the isotope labels may be incorporated into any lipid or lipid derivative.

Carbohydrates and Carbohydrate Derivatives as Biological Molecules

The lipids and lipid derivatives listed in Table 1 are merely exemplary; the isotope labels may be incorporated into any lipid or lipid derivative.

Isotope labels from isotope-labeled water may also be incorporated into carbohydrates or carbohydrate derivatives. These include monosaccharides (including, but not limited to, glucose and galactose), amino sugars (such as N-AcetylGalactosamine), polysaccharides (such as glycogen), glycoproteins (such as sialic acid) glycolipids (such as galactocerebrosides), glycosaminoglycans (such as hyaluronic acid, chondroitin-sulfate, and heparan-sulfate) by biochemical pathways known in the art.

Hydrogen and oxygen labels from isotope-labeled water may be incorporated into any carbohydrate or carbohydrate derivative, such as those depicted in Table 1. The carbohydrate or carbohydrate derivatives listed in Table 1 are merely exemplary; the isotope labels may be incorporated into any carbohydrate or carbohydrate derivative.

The foregoing is merely exemplary. Isotope labels may be incorporated into any other known biological molecule.

B. Obtaining One or More Biological Samples from One or More Tissues or Individuals One or more biological samples are obtained from the tissue or individual. The one or more biological samples may be obtained, for example, by blood draw, urine collection, biopsy, or other methods known in the art. The one or more biological samples may be one or more biological fluids. Biological samples may also be obtained from specific organs or tissues, such as muscle, liver, adrenal tissue, prostate tissue, endometrial tissue, blood, skin, and breast tissue. The biological sample may be from a specific group of cells, such as tumor cells or fibroblast cells. The one or more biological samples may be obtained pre-mortem or post-mortem. Biological molecules may be obtained, and optionally partially purified or isolated, from the biological sample using standard biochemical methods known in the art.

The one or more biological samples together include two or more biological molecules. For example, all biological molecules may be obtained from a single biological sample. Alternatively, one biological molecule may be obtained from a first biological sample, and another biological molecule may be obtained from a second biological sample. Two or more biological molecules may be obtained from each biological sample.

In a preferred embodiment, the biological molecules may also be of different chemical classes. For example, a first biological molecule may be mixed cellular proteins of a tissue or individual, while the second biological molecule may be genomic DNA of a tissue or individual. The two or more biological molecules may also be specific molecules within different chemical classes. As another example, a first biological molecule may be a specific protein with a specific amino acid sequence, and a second biological molecule may be a polynucleotide with a specific nucleic acid sequence.

The frequency of biological sampling can vary depending on different factors. Such factors include, but are not limited to, the nature of the biological molecules, ease and safety of sampling, molecular flux rates of the biological molecules or the biological molecule from which it was derived, and the half-life of a therapeutic agent or biological agent.

The biological molecules may also be purified partially, or optionally, isolated, by conventional purification methods including high pressure liquid chromatography (HPLC), fast performance liquid chromatography (FPLC), chemical extraction, thin layer chromatography, gas chromatography, gel electrophoresis, and/or other separation methods known to those skilled in the art.

In another embodiment, the biological molecules may be hydrolyzed or otherwise degraded to form smaller molecules. Hydrolysis methods include any method known in the art, including, but not limited to, chemical hydrolysis (such as acid hydrolysis) and biochemical hydrolysis (such as peptidase, lipase or nuclease degradation). Hydrolysis or degradation may be conducted either before or after purification and/or isolation of the biological molecules. The biological molecules also may be partially purified, or optionally, isolated, by conventional purification methods including high performance liquid chromatography (HPLC), fast performance liquid chromatography (FPLC), gas chromatography, gel electrophoresis, and/or any other methods of separating chemical and/or biochemical compounds known to those skilled in the art.

C. Detecting the Incorporation of the Isotope Label in the Two or More Biological Molecules Isotopic enrichment in biological molecules can be determined by various methods such as mass spectrometry, including but not limited to gas chromatography-mass spectrometry (GC-MS), isotope-ratio mass spectrometry, GC-isotope ratio-combustion-MS, GC-isotope ratio-pyrrolysis-MS, liquid chromatography-MS, electrospray ionization-MS, matrix assisted laser desorption-time of flight-MS, Fourier-transform-ion-cyclotron-resonance-MS, cycloidal-MS, nuclear magnetic resonance (NMR), or liquid scintillation counting.

Incorporation of isotope labels into biological molecules may be measured directly. Alternatively, incorporation of isotope labels may be determined by measuring the incorporation of isotope labels into one or metabolic derivatives, hydrolysis products, or degradation products of biological molecules. The hydrolysis or degradation products may optionally be measured following either partial purification or isolation by any known separation method. Stable isotope-labeled substrates are incorporated into biological molecules comprising one or more metabolic pathways of interest. In this manner, the molecular flux rates can be determined by measuring, over specific time intervals, isotopic content and/or pattern or rate of change of isotopic content and/or pattern in the targeted molecules, for example by using mass spectrometry (discussed supra), allowing for the determination of the molecular flux rates within the one or more metabolic pathways of interest, by use of analytic and calculation methods known in the art.

Isotope labels in biological molecules may be detected simultaneously. For example, a mass spectrometer may be used to detect the ions of biological molecules and/or components thereof simultaneously, without requiring the physical separation, purification, or isolation of the different biological molecules.

Mass Spectrometry

Mass spectrometers convert biological molecules, and/or components thereof, into rapidly moving gaseous ions and separate them on the basis of their mass-to-charge ratios. The distributions of isotopes or isotopologues of ions, or ion fragments, may thus be used to measure the isotopic enrichment in two or more biological molecules.

Generally, mass spectrometers include an ionization means and a mass analyzer. A number of different types of mass analyzers are known in the art. These include, but are not limited to, magnetic sector analyzers, electrostatic analyzers, quadrupoles, ion traps, time of flight mass analyzers, and Fourier transform analyzers. In addition, two or more mass analyzers may be coupled (MS/MS) first to separate precursor ions, then to separate and measure gas phase fragment ions.

Mass spectrometers may also include a number of different ionization methods. These include, but are not limited to, gas phase ionization sources such as electron impact, chemical ionization, and field ionization, as well as desorption sources, such as field desorption, fast atom bombardment, matrix assisted laser desorption/ionization, and surface enhanced laser desorption/ionization.

In addition, mass spectrometers may be coupled to separation means such as gas chromatography (GC) and high performance liquid chromatography (HPLC). In gas-chromatography mass-spectrometry (GC/MS), capillary columns from a gas chromatograph are coupled directly to the mass spectrometer, optionally using a jet separator. In such an application, the gas chromatography (GC) column separates sample components from the sample gas mixture and the separated components are ionized and chemically analyzed in the mass spectrometer.

When GC/MS (or other mass spectrometric modalities that analyze ions of organic molecules, rather than small inorganic gases) is used to measure mass isotopomer abundances of organic molecules, hydrogen-labeled isotope incorporation from isotope-labeled water is amplified 3 to 7-fold, depending on the number of hydrogen atoms incorporated into the organic molecule from isotope-labeled water in vivo.

Liquid Scintillation Counting

Radioactive isotopes may be observed using a liquid scintillation counter. Radioactive isotopes such as $^3H$ emit radiation that is detected by a liquid scintillation detector. The detector converts the radiation into an electrical signal, which is amplified. Accordingly, the number of radioactive isotopes in a biological molecule may be measured.

In one embodiment, the radioisotope-enrichment value in a biological sample may be measured directly by liquid scintillation. In a further embodiment, the radio-isotope is $^3H$.

In another embodiment, the biological molecules or components thereof may be partially purified, or optionally isolated, and subsequently measured by liquid scintillation counting.

Determining Molecular Flux Rates

Molecular flux rates may be calculated by combinatorial analysis, by hand or via an algorithm. Variations of Mass Isotopomer Distribution Analysis (MIDA) combinatorial algorithm are discussed in a number of different sources known to one skilled in the art. Specifically, the MIDA calculation methods are the subject of U.S. Pat. No. 5,336,686, incorporated herein by reference. The method is further discussed by Hellerstein and Neese (1999), as well as Chinkes et al. (1996), and Kelleher and Masterson (1992), all of which are hereby incorporated by reference in their entirety.

In addition to the above-cited references, calculation software implementing the method is publicly available from Professor Marc Hellerstein, University of California, Berkeley.

A precursor-product relationship is then applied. For the continuous labeling method, the isotopic enrichment is compared to asymptotic (i.e., maximal possible) enrichment and kinetic parameters of biological molecules (e.g., biosynthesis rates) are calculated from precursor-product equations. For the discontinuous labeling method, the rate of decline in isotope enrichment is calculated and the kinetic parameters of biological molecules are calculated from exponential decay equations.

The fractional synthesis rate ($k_s$) of biological molecules may be determined by application of the continuous labeling, precursor-product formula:

$$k_s=[-\ln(1-f)]/t,$$

where f=fractional synthesis=product enrichment/asymptotic precursor enrichment and t=time of label administration of contacting in the system studied.

Similarly, breakdown rate constants ($k_d$) may be calculated based on an exponential or other kinetic decay curve:

$$k_d=[-\ln f]/t$$

D. Comparing Two or More Molecular Flux Rates of Two or More Biological Molecules The molecular flux rates of two or more biological molecules are compared. The comparison allows for the analysis of dynamic relationships between different biological molecules to be determined.

The relationship between molecular flux rates of different biological molecules provides significantly more information than is provided by a single molecular flux rate. Determining the molecular flux rate of a single biological molecule in a tissue or individual only provides information about the nominal molecular flux rate of a biological molecule. Comparing the relative molecular flux rates, however, provides context to a molecular flux rate. For example, comparing the relative molecular flux rates of entire classes of biological molecules indicates whether the molecular flux rate of one class of molecules (e.g., proteins) is proportionally higher than the molecular flux rate of another class of molecules (e.g., lipids or DNA). If only a single molecular flux rate is measured, the proportionality of the molecular flux rate in the context of the tissue or individual is lost. Comparing the relative molecular flux rates of specific biological molecules in the same biochemical pathway may be used to analyze whether a change in the molecular flux rate of one biological molecule is related to the change in molecular flux rate of another biological molecule.

Comparison of molecular flux rates also allows measurement of biological molecule kinetics associated with diseases, disorders, conditions, therapeutic compound treatment, and toxicity of biological or chemical agents, among others. Comparing the relative molecular flux rates of two or more biological molecules may be used to identify a disease, disorder, or condition which cannot be identified merely by measuring and comparing the nominal change in molecular flux rate of a single biological molecule. Similarly, changes in the relative molecular flux rates resulting from administration of a therapeutic agent or biological agent may be determined.

The comparison of molecular flux rates may be accomplished by any comparison methods known in the art. For example, the molecular flux rates of the two or more biological molecules may be expressed in a ratio, or in a graphical relationship.

Disease Detection

The compared molecular flux rates may be used to detect, prognose, or monitor the progression of a disease, disorder, or medical condition. Exemplary, but non-limiting examples of biochemical processes that can be measured and relevant diseases are provided in Table 2. A difference in the compared molecular flux rates of two or more biological molecules between a population of tissues or individuals that does not have the disease or disorder and a second population that does have the disease or disorder may be used to detect, prognose, or monitor the progression of the disease. For example, interstitial pulmonary fibrosis may be diagnosed, prognosed, or monitored by comparing the difference between the compared molecular flux rates of lung collagen and fibroblast DNA between one or more tissues or individuals that have interstitial pulmonary fibrosis and one more tissues or individuals that do not. Alternatively, the difference in compared molecular flux rates of two or more biological molecules in a single population of tissues or individuals at two or more times may be used to detect, prognose, or monitor the progression of the disease.

Hyperlipidemia may also be diagnosed, prognosed, or monitored by comparing the relative molecular flux rates of two or more of apolipoprotein B, triglycerides, phospholipids, or cholesterol in one or more tissues or individuals that have hyperlipidemia and one or more tissues or individuals that do not. In one variation, an increase in the molecular flux rate of apolipoprotein B relative to triglycerides, phospholipids, or cholesterol may be used to diagnose, prognose, or monitor familial combined hyperlipidemia. For example, the measurement may compare the ratio of apolipoprotein B synthesis to triglyceride synthesis. Alternatively, the difference in compared molecular flux rates in a single population of tissues or individuals at two or more times may be used to detect, prognose, or monitor the progression of the hyperlipidemia.

Alternatively, a state of reduced or impaired cellular immunity distinct from humoral immunity may be diagnosed, prognosed, or monitored by comparing the relative molecular flux rates of T or B cell DNA or proteins with plasma immunoglobulins (proteins). A decrease in the T or B cell DNA molecular flux rate relative to the plasma immunoglobulin molecular flux rate indicates specifically reduced cellular immune activation or function in the test population. Alternatively, the difference in compared molecular flux rates in a single population of tissues or individuals at two or more times may be used to detect, prognose, or monitor the progression of a state of reduced or impaired cellular immunity.

In addition, photoaging (skin wrinkles) may be diagnosed, prognosed, or monitored by comparing the relative molecular flux rates of dermal collagen and dermal elastin or dermal lipids. An alteration in the dermal collagen molecular flux rate relative to the elastin or lipid molecular flux rate indicates an altered rate of photoaging in the second population, e.g., a reduced ratio of collagen:elastin synthesis being consistent with an ongoing high rate of photoaging in the individual or skin location. Alternatively, the difference in compared molecular flux rates in a single population of tissues or individuals at two or more times may be used to detect, prognose, or monitor the progression of Testing Therapeutic Agents (Compounds)

The effectiveness of therapeutic agents (i.e., compounds) may be tested using the methods described herein. A difference in the relative molecular flux rates of two or more biological molecules between a population to which a therapeutic agent has been administered and a control, untreated population identifies or measures the effectiveness of a therapeutic agent in tissues or individuals of the treated population. Alternatively, a difference in the relative molecular flux rates of two or more biological molecules in a population before and after a therapeutic agent has been administered identifies or measures the effectiveness of the therapeutic agent on tissues or individuals of the treated population.

Therapeutic agents may be any chemical compound or composition, or biological factor, known in the art. Therapeutic agents include, but are not limited to, any chemical compound or composition disclosed in, for example, the 13th Edition of *The Merck Index* (a U.S. publication, Whitehouse Station, N.J., USA), incorporated herein by reference in its entirety. As stated above, therapeutic agents also include biological factors, examples of which include monoclonal antibodies, soluble receptors, or vaccines.

In one example, a method of determining a tumoricidal or tumor static effect of a chemotherapeutic agent during chemotherapy may be determined by comparing the relative molecular flux rates of cellular protein and cellular DNA. The difference in relative molecular flux rates between a test population that has received the chemotherapeutic agent and a control population that has not, measures the effectiveness of the chemotherapeutic agent in tissues or individuals in need of the chemotherapeutic agent. By way of example, if the relative rate of DNA synthesis to protein synthesis was reduced after administration of the chemotherapeutic agent or in populations treated with the chemotherapeutic agent compared to untreated populations, the chemotherapeutic agent could be concluded to have a tumoristatic effect. Alternatively, if the relative rate of DNA synthesis to protein synthesis remained about the same after administration of the chemotherapeutic agent or in populations treated with the chemotherapeutic agent compared to untreated populations, the chemotherapeutic agent could be concluded to have a tumoricidal effect. Alternatively, the difference in relative molecular flux rates in a population of one or more tissues or individuals before and after administration of a chemotherapeutic agent measures the effectiveness of the chemotherapeutic agent.

The cidal or static effects of an antibiotic may analogously be determined by administering an antibiotic instead of a chemotherapeutic agent. By way of example, if the relative rate of DNA synthesis to protein synthesis was reduced after administration of said antibiotic or, in the population treated with said antibiotic compared to untreated populations, said antibiotic could be concluded to have a static effect on said infectious organism in said tissues or individuals. By "cidal" is meant the killing of the targeted infectious organism by the antibiotic. By "static" is meant the inhibition of growth or replication or proliferation or reproduction of the targeted infectious organism by the antiobiotic. If the infectious organism is a bacterium, then the term "bacteriocidal" is applied to the antibiotic. Likewise, the term "bacteriostatic" applies to antibiotics that inhibit bacterial growth or replication or proliferation or reproduction.

In another embodiment, one or more beneficial therapeutic effects of an androgen in one or more tissues or individuals with a wasting disease or disorder of frailty may be determined. A difference in the molecular flux rate of muscle protein or DNA relative to the molecular flux rate of adipose tissue triglyceride between a population to which the androgen has been administered and a population to which the androgen has not been administered identifies or measures the beneficial therapeutic effect. Alternatively, the difference in relative molecular flux rates between a population of one or more tissues or individuals before and after administration of an androgen measures its effectiveness. An increase in the molecular flux rate of the muscle protein or DNA relative to the molecular flux rate of the adipose tissue triglyceride after therapy identifies a beneficial therapeutic effect of the androgen in the wasting disease or disorder of frailty. A beneficial therapeutic effect of other muscle anabolic factors, such as growth hormone, in a wasting disease or disorder of frailty may be identified in the same manner, by administering the growth hormone instead of the androgen.

The methods disclosed herein may also be used to identify one or more beneficial therapeutic effects of a selective estrogen receptor modulator (SERM), such as tamoxifen or raloxifen. For example, beneficial therapeutic effects of a SERM in breast cancer prevention may be identified by measuring the relative molecular flux rates of mammary epithelial cell DNA to breast tissue proteins or lipids in a first population of tissues or individuals to which the SERM has been administered compared to an individual or individuals to which the SERM has not been administered. A first biological molecule may be a mammary epithelial cell DNA and a second biological molecule may be a protein or DNA from one or more estrogen-insensitive cells in the breast. The estrogen-insensitive cells may be from, for example, adipose, fibroblasts, stromal cells, endothelial cells or other non-epithelial cells. Alternatively, the difference in relative molecular flux rates in a population of one or more tissues or individuals before and after administration of the SERM identifies the beneficial therapeutic effect. A decrease in the molecular flux rate of the mammary epithelial DNA relative to the molecular flux rate of the breast tissue proteins or lipids identifies a beneficial preventative effect of the SERM against breast cancer.

A beneficial therapeutic effect of an exercise regimen or a therapeutic agent given to increase aerobic capacity (fitness) of elderly, deconditioned patients may be identified by comparing the relative molecular flux rates of mitochondrial DNA or cardiolipin to genomic DNA or mixed cellular proteins in muscle tissue of a population of one or more individuals to which the agent has been administered to a population or one or more individuals to which the agent has not been administered. Alternatively, the beneficial therapeutic effect may be identified by comparing the molecular flux rates in a population of one or more individuals to the same individual or individuals before and after administering the agent. An increase in the molecular synthesis rates of muscle mitochondrial or cardiolipin to the molecular synthesis rate of the muscle genomic DNA or mixed cellular proteins identifies a beneficial therapeutic effect of the exercise regimen or therapeutic agent on fitness.

In addition, a beneficial therapeutic effect of a hormonal or other therapeutic agent in Alzheimer's disease may be identified by comparing the relative molecular flux rates of cerebrospinal fluid or blood amyloid-beta protein (a marker of fibrillogenesis in the brain) and cerebrospinal fluid or blood 25-hydroxycholesterol (a marker of general brain cell repair and turnover) in a population of one or more individuals before and after administration of a hormonal or other therapeutic agent. Alternatively, the beneficial therapeutic effect may be identified by comparing these relative molecular flux rates in a population of one or more individuals after administration of the hormonal or other therapeutic agent to Alzheimer's disease patients to whom the hormonal or other therapeutic agent has not been administered. A decrease in the molecular flux rate of amyloid beta protein relative to the molecular flux rate of the 25-hydroxy cholesterol identifies a beneficial therapeutic effect of the hormonal or other therapeutic agent against Alzheimer's disease.

The invention also includes methods of identifying a therapeutic property of a biological agent. The relative molecular flux rates of two or more biological molecules are determined in a population of one or more tissues or individuals to which a biological agent has been administered and a population of one or more tissues or individuals to which the biological agent has not been administered. A difference in the relative molecular flux rates identifies a therapeutic property of the biological agent. Alternatively, the therapeutic property may be identified by comparing the molecular flux rates in a population of one or more individuals to the same population before and after administering the agent. The therapeutic property may be an undiscovered property of an already-approved drug (i.e., an "old" drug), for example. The biological sample may be a tissue culture, and the individual may be an experimental animal or a human. Drug agents may be any chemical or biological compound or composition known in the art. Drug agents include, but are not limited to, any chemical compound or composition disclosed in, for example, the 12th Edition of *The Merck Index* (a U.S. publication, Whitehouse Station, N.J., USA), incorporated herein by reference in its entirety. The method may be used to screen a plurality of drug agents in a high-throughput manner.

Toxic effects of drug agents, including biological agents, may also be determined by the methods of the present invention.

Multiple Concurrent Measurements Used for Screening Functions

Because of the great breadth of measurements that are possible using isotope-labeled water, screening for unexpected or unidentified actions of drugs or general protein targets is possible. Examples include the effects of statins (3-hydroxy-3-methylglutaryl coenzyme A reductase inhibitors) on brain myelin or amyloid-β synthesis or bone collagen kinetics relative to cholesterol synthesis; effects of glitazones (e.g., thiazolidinedione) on colon, pancreatic or other cell proliferation rates relative to adipose triglyceride synthesis or hepatic glucose synthesis rates; effects of antiretroviral agents (reverse transcriptase inhibitors) on muscle mitochondrial DNA or cardiolipin synthesis relative to adipose tissue triglyceride or genomic DNA synthesis. As a general screening approach, concurrent measurement of the effects of an agent or target on numerous pathways concurrently, including brain myelination, bone collagen turnover, chondrocyte proliferation, vascular smooth muscle cell proliferation, tissue fibrogenesis, joint space hyaluronic acid and chondroitin sulfate synthesis and breakdown, brain amyloid-beta production, spermatogenesis, proliferation of prostate, breast or colon cells, dermal collagen synthesis, epidermal keratin synthesis or keratinocyte proliferation, T-cell proliferation and death, immunoglobulin synthesis, adipose tissue triglyceride synthesis and breakdown, muscle myelin synthesis and breakdown, mitochondrial biogenesis, and many other molecular flux rates (see Table 1), and thereby allows broad screening to be a feasible approach.

High-throughput of Multiple Simultaneous (Concurrent) Measurements

The methods disclosed herein allow the study of relative molecular flux rates in hundreds or thousands of animals for periods of weeks or months, because of the simplicity of the protocol. Each animal (or human subject) is simply allowed to drink water containing labeled water, such as $^2H_2O$. This continues for as long as is required by the labeling protocol. If the molecular flux rates of two or more biological molecules are determined by mass spectrometry, the method may be completely automated (autosampled, computerized data analysis and calculation of flux rates).

The high volume that is made easy with the isotope-labeled water administration differs from previous labeling techniques, which have required labor-intensive or invasive or continuous administration protocols (e.g., intravenous or repeated oral or intraperitoneal dosing) to maintain stability in the precursor-pool isotope enrichment and which also have required administration of multiple different tracers, if multiple fluxes of molecules from different classes are to be measured. This capacity for high throughput is key to drug development and discovery, where extremely large numbers of candidate drugs or genes need to be evaluated by the trial-and-error method and consequences on multiple molecular flux rates as end-points have to be measurable.

Figure 3:
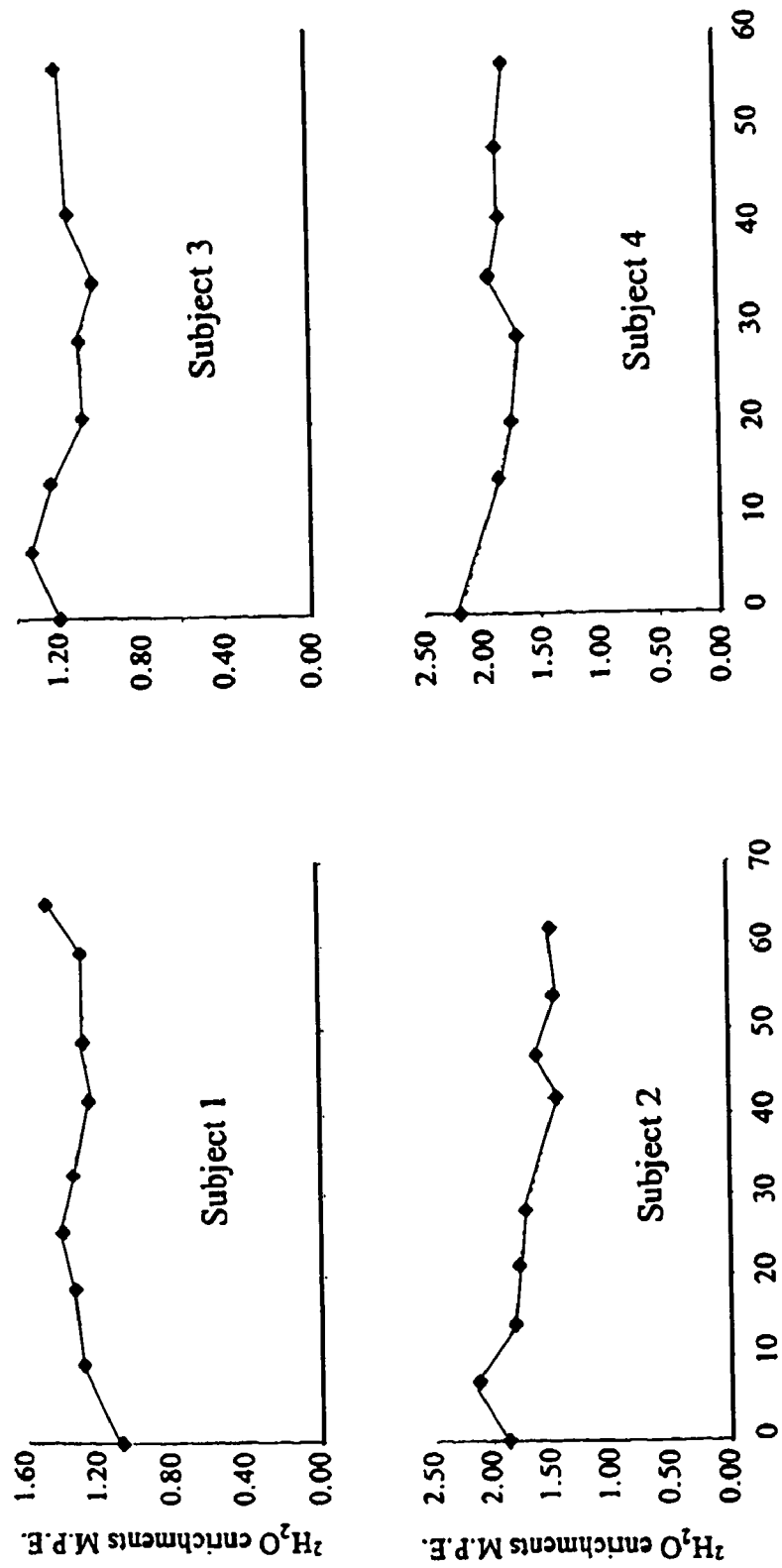
FIG. 3 depicts enrichments of $^2H_2O$ in body water of representative human subjects who drank 50–100 mL of $^2H_2O$ daily for 10–12 weeks. The data show that the precursor pool of body water is stable over a period of weeks for each subject.

Capacity to Evaluate Long-term, Slowly Evolving Toxicities or Therapeutic Actions Many biological processes that are important to potential toxic or therapeutic actions of candidate drugs or genes are very slow to evolve. These slowly evolving processes can be monitored by methods of administering isotope-labeled water, unlike other kinetic techniques. This is because of the extreme ease and simplicity of administering isotope-labeled water, such as $^2H_2O$, in drinking water. $^2H_2O$ labeling studies have been carried out with minimal effort for 3–6 months in experimental animals and human subjects (see, e.g., FIG. 3). Such slowly evolving processes that can be monitored include kinetics of vascular smooth muscle cells, lymphocytes, brain constituents, tissue mitochondria, epithelial stem cells, and bone and tissue collagen, and many others.

Kits

The invention provides kits for measuring and comparing molecular flux rates in vivo. The kits may include isotope-labeled water (particularly $^2H_2O$, $^3H_2O$, and $H_2^{18}O$ isotope-labeled labeled water or a combination thereof), and in preferred embodiments, chemical compounds known in the art for separating, purifying, or isolating biological molecules, and/or chemicals necessary to obtain a tissue sample, automated calculation software for combinatorial analysis, and instructions for use of the kit.

Other kit components, such as tools for administration of water (e.g., measuring cup, needles, syringes, pipettes, IV tubing), may optionally be provided in the kit. Similarly, instruments for obtaining samples from the subject (e.g., specimen cups, needles, syringes, and tissue sampling devices) may also be optionally provided.

EXAMPLES

The following non-limiting examples further illustrate the invention disclosed herein:

Example 1

Ratio of DNA: Protein Synthesis in Growing Tissues.

The ratio of $^2$H-incorporation from $^2H_2O$ into DNA: protein in muscle, liver or other tissues reveals whether tissue growth is due to hyperplasia (addition of new cells) or hypertrophy (growth in size of each cell, without addition of new cells). This distinction is key to evaluating growth factors, genes or other interventions designed to alter the mass of any tissue. DNA: protein synthesis rates are measured concurrently by administering labeled water and detecting the incorporation of the isotope label in the DNA and proteins.

Example 2

Ratio of DNA: Protein Synthesis in Tumor Cells or Microorganisms During Chemotherapy.

The ratio of DNA: protein kinetics in bacteria during antibiotic chemotherapy reveals whether the antibiotic agent is working in a bactericidal manner (killing cells) or in a bacteriostatic manner (preventing cells from growing but not killing them). Similarly, ratios of DNA: protein kinetics in a tumor during chemotherapy reveals if cell death has been induced or growth has been halted (tumoricidal vs. tumoristatic effects). DNA: protein synthesis rates are measured concurrently by administering labeled water and detecting the incorporation of the isotope label in the DNA and proteins.

Example 3

Ratio of Mitochondrial DNA to Cellular Protein or Genomic DNA Synthesis Rates.

The occurrence of mitochondrial biogenesis independent of somatic growth of tissues can be very important, for example, in the training response of muscle to aerobic exercise. The ratio of mtDNA synthesis to cellular protein or genomic DNA synthesis reveals growth-independent mitochondrial biogenesis and turnover, and represents a biomarker of aerobic fitness. Synthesis rates of mtDNA and cellular proteins or genomic DNA are measured concurrently by administering labeled water and detecting the incorporation of the isotope label in the mtDNA and cellular proteins or genomic DNA (for example, see FIGS. 1 and 2).

Sprague-Dawley rats (wt 210–350 g) from Simonsen were housed in wire cages, 3 per cage with a 12 hour light/dark cycle. All procedures were approved by the UC Berkeley Office of Laboratory Animal Care. Purina rat chow was provided ad libitum. There were 2 groups of rats, a young male growing group (2–4 months of age at the beginning of studies) and an older, weight-stable female group (8–10 months of age). Initial average rat weights from the young rat group was approximately 210 g while the initial average body weights from the older, weight-stable group was approximately 225 g.

$^2H_2O$ labeling protocols in rodents consisted of an initial intraperitoneal priming bolus to 2.0–2.5% body water enrichment. The priming dose of $^2H_2O$ (100%) was given to the rats (e.g., for a 225 g rat, 2% of 135 ml, or 2.7 ml, given in divided doses 1 hour apart) based on estimated 60% body weight as water, followed by administration of 4% $^2H_2O$ in the drinking water. The 4% enrichment of $^2$H2O in drinking water was chosen as a convenient dose that produces sufficient enrichments in biosynthetic products of interest and has no known toxicities. $^2H_2O$ (70% and 100%) was purchased commercially from Cambridge Isotopes (Andover, Mass.). Drinking was ad-libitum. Rats were sacrificed by $CO_2$ asphyxiation.

Bone marrow and cardiac (0.5 g) and hindlimb muscle (0.3 g) samples from individual animals were removed immediately after sacrifice. Muscle samples were homogenized and mitochondria from the homogenate were then isolated by density gradient centrifugation. Nuclear DNA (nDNA) contamination was removed enzymatically by treatment with DNAse. Absence of nDNA contamination in muscle samples was confirmed by polymerase chain reaction (PCR) followed by gel electrophoresis. More than sufficient mtDNA was obtained from 0.3–0.5 g of muscle tissue for measurement of mtDNA kinetics in individual animals.

Bone marrow nDNA was isolated by use of a Qiamp column (Qiagen) using techniques well known in the art. MtDNA was also isolated from cardiac muscle, hindlimb muscle and platelets using the Qiagen Kit (Qiagen) after isolation of the mitochondrial fraction from the tissue. MtDNA and nDNA were hydrolyzed enzymatically to free deoxyribonucleosides. A LC18 SPE column (Supelco, Bellefone, Pa.) was used to separate dA from the other deoxyribonucleosides. The column was washed with 100% methanol (2 ml) and water (2 ml). The hydrolyzed DNA sample was then added to the column and nucleosides other than dA were eluted with an $H_2O$ wash (5 ml). The dA was then eluted with 50% methanol (1 ml).

The deoxyribose (dR) moiety of dA was analyzed by GC/MS, after conversion to its pentane-tetraacetate derivative. The isotopic enrichment of dR was determined by GC/MS analysis (m/z 245 and 246, representing M0 and M1 masses, respectively). There is no exchange between solvent water or other sample matrix protons and hydrogen atoms in C—H bonds of deoxyribose in DNA or free deoxyribonucleosides. The derivative that was analyzed contains only the dR moiety, not the base portion, of purine deoxyribonucleosides, so label incorporation into the base moiety via base salvage pathways is not a confounding factor.

Unlabeled (natural abundance) dA standards were analyzed concurrently in each run to establish the dependence of measured isotopic ratio on amount of sample injected (abundance sensitivity). This dependence can be characterized by plotting the abundance of the parent M+0 ion (m/z 245) versus the ratio of $M_{+1}$ to $M_{+0}$ plus $M_{+1}$ ions (246/(245+246)). A linear regression of the ratio versus $M_0$ abundance was calculated, as described supra. The regression line was then used to calculate the natural abundance ratio at any particular $M_0$ abundance, for calculations of excess abundances in samples.

Fractional synthesis rates of cells were calculated by use of the precursor-product relationship as described, supra. The isotopic enrichment of a completely (or nearly-completely) turned-over tissue can be used as a measure of the true precursor enrichment for the cells of interest. Under conditions of steady-state in the pool size the fractional synthesis rate also represents the fractional replacement rate (i.e., assuming that every cell or molecule produced must be balanced by a cell or molecule destroyed). The replacement constant (k) and half-life (t ½) of mtDNA after $^2H_2O$ labeling were calculated as described, supra. The central principle behind the mathematics of the precursor-product relationship is that the isotopic enrichment of a product derived exclusively from a precursor pool will approach the isotopic enrichment of the precursor pool, with the shape of an exponential curve.

Body water $^2H_2O$ enrichments were measured serially. The steady state body $^2H_2O$ enrichments attained in rats maintained on 4% $^2H_2O$ in drinking water were approximately 3.0% and were stable over time in individual animals.

Young male rats were studied first, as a model of mitochondrial biogenesis that included somatic growth. Body weights from young male rats increased by more than 50% over the duration of $^2H_2O$ labeling. Enrichments of bone marrow nDNA remained stable at 9.5–10.0% through 11 weeks of labeling. Enrichments of cardiac and hindlimb mtDNA increased from 0.0%–3.5% over time. Fractional synthesis (f) of mt DNA from hindlimb and cardiac muscle also increased over time. Approximately 40–50% of mtDNA was newly synthesized after 11 weeks of labeling with $^2H_2O$ in both tissues, with the value in hindlimb muscle appearing to plateau at about 45%.

In order to distinguish between mtDNA synthesis related to tissue accrual and mtDNA replacement independent of growth, we also studied older, weight-stable female rats. Body weights over time were relatively stable in these animals, as expected, with only a 10% increase over the 9 week labeling period. Bone marrow dA enrichment values were stable and not different from growing male rats. Tissues were sampled through week 9 of $^2H_2O$ labeling. In cardiac muscle, the mtDNA synthesis (ca. 20% new) after 8 weeks of $^2H_2O$ labeling was greater than somatic growth (ca. 10%). In skeletal muscle, mtDNA synthesis was similar in magnitude to somatic growth, so synthesis independent of growth was not demonstrated by this means. The rate constant of synthesis was about 0.4% per day in cardiac muscle. After correcting for somatic growth (10% over 9 weeks), the calculated fractional replacement rate of cardiac muscle mtDNA was about 0.2%/day, consistent with a half-life of 350 days for mtDNA.

Comparison of mtDNA to nDNA Sythesis in Muscle Tissue by Concurrent Measurement

Figure 5:
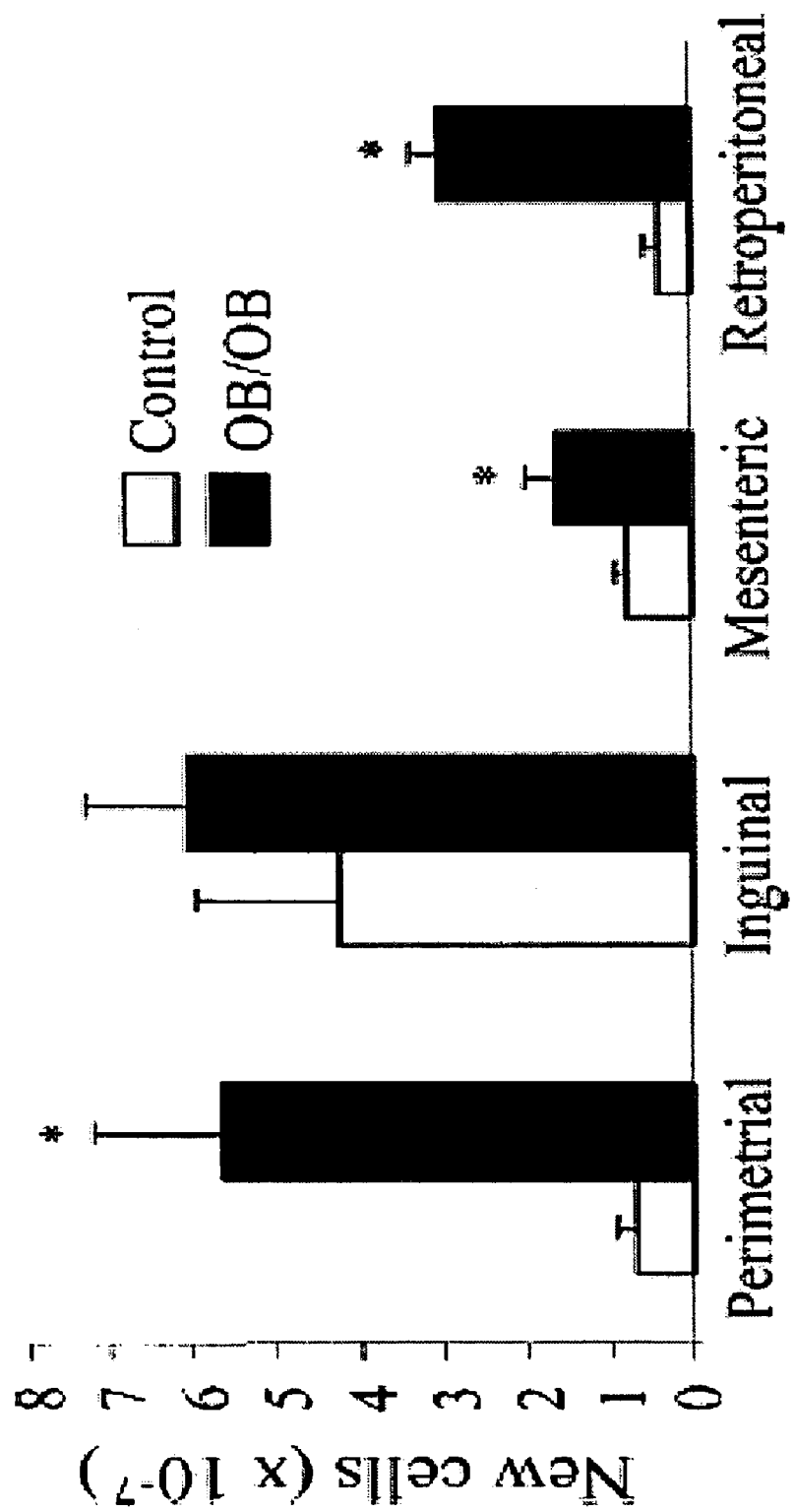
FIG. 5 depicts the simultaneous measurement of cell proliferation rates in the mature adipocyte-enriched fraction isolated from four different adipose depots (perimetrial, inguinal, mesenteric, and retroperitoneal) of control (n=7) and ob/ob (n=4) mice. Animals received 4% $^2H_2O$ in drinking water for 21 days. Controls weighed 18.5±0.2 g (mean±S.E.) at the start of $^2H_2O$ administration and 20.8±0.4 g at the end. Ob/ob weighed 26.3±0.6 g and 35.7±0.9 g, respectively.

The fractional synthesis of nDNA and mtDNA in cardiac and hindlimb muscle were compared in weight stable female rats. Higher synthesis rates of mtDNA compared to genomic DNA, by about 2-fold after 6–9 weeks, were observed in both cardiac and hindlimb muscle tissues (FIG. 5). Of note, skeletal muscle nDNA synthesis was of lower magnitude (ca 5% after 9 weeks) than whole body somatic growth (ca 10%) in these animals, whereas cardiac muscle nDNA synthesis (ca 10%) was of similar magnitude as somatic growth. The observation that mtDNA synthesis is greater than nDNA synthesis in these tissues is important because these results are consistent with mtDNA replication independent of cell division. If mtDNA synthesis is corrected for new myocyte proliferation (nDNA synthesis), the half-life of mtDNA in non-growing tissue can be estimated, as was done based on somatic growth (see above). Calculated half-life in cardiac muscle was ca. 350 days (replacement rate constant 0.2% $d^{-1}$) and in skeletal muscle was about 700 days (replacement rate constant 0.1% $d^{-1}$).

Figure 4:
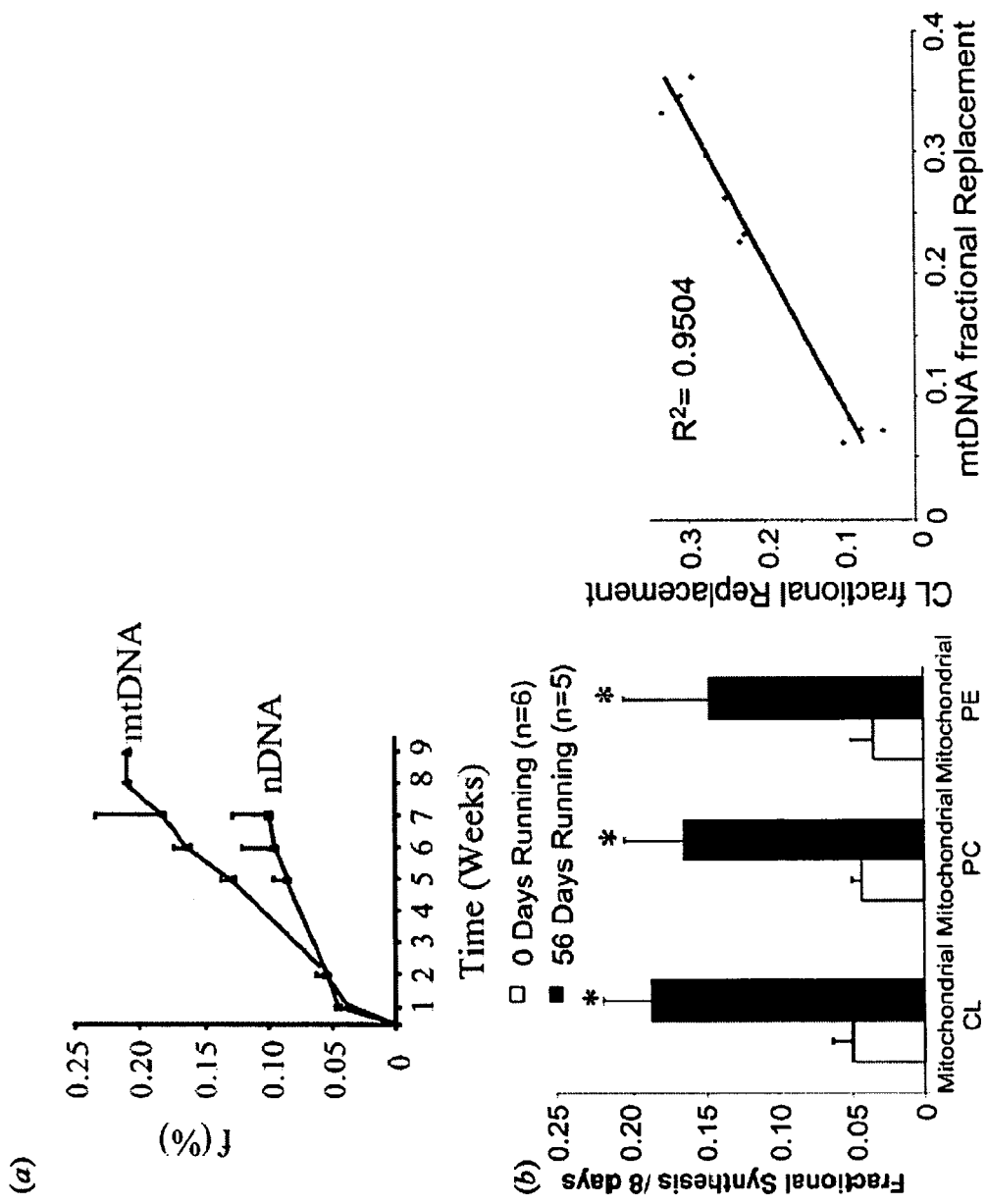
FIG. 4 depicts (a) comparison of mtDNA to nuclear DNA synthesis in cardiac and hind-limb muscle of weight-stable female rats (mean±S.D.); f, fractional replacement and (b) Left, synthesis of mitochondrial (mt) phospholipids in hind-limb muscle of rats, and effect of exercise training (voluntary wheel running). Animals received $^2H_2O$ for eight days. CL, cardiolipin; PC, phosphatidyl-choline; PE, phosphatidyl-ethanolamine; $P<0.05$ versus control rats. Right, correlation between mtDNA and CL synthesis in rats from (a).

The results confirm relatively slow synthesis rates of hindlimb and cardiac muscle mtDNA in normal rats. True turnover (i.e., replacement in the absence of somatic growth) does seem to occur, based on comparison of mtDNA to nDNA synthesis in both cardiac and skeletal muscle (FIG. 4). Somatic growth of tissue accounted for about 50% of mtDNA synthesis. The apparent half-life of mtDNA in weight-stable rats ranged between 12–24 months for cardiac and hinblimb muscle, respectively, after correction for new mitochondria added during growth of tissues.

Example 4

Relation Among Synthesis Rates of Adipose Tissue Acyl-glycerides and Protein or DNA Synthesis in Other Somatic Tissues.

The effects of an intervention on body composition are evaluated by the relative synthesis rate of acyl-glycerides in adipose tissues vs. protein and DNA in muscle and liver or other somatic tissues. Stimulation of muscle protein and DNA synthesis with suppression of adipose tissue triglyceride synthesis, for example, reflects a beneficial therapeutic effect for agents such as androgens or recombinant growth hormone in patients with wasting or frailty. Syntheses of adipose tissue triglycerides and protein and DNA in somatic tissues are measured concurrently by administering labeled water and detecting the incorporation of the isotope label in adipose tissue acyl-glycerides and protein or DNA in somatic tissues.

Four week old, female, C57/bl6j mice (Jackson Labs Bar Harbor, Mich.) were divided into four groups: C57/bl6j$^{+/?}$ controls (con), ad libitum fed C57/bl6j$^{lep-/lep-}$ (ob/ob), leptin treated ob/ob (ob-lep) and food restricted ob/ob (ob-r).

All mice were housed individually in hanging wire cages and given free access to water. The light cycle was on from noon to midnight and mean temperature was 73° F. Diets were from a purified formula with 1 g "dustless" pellets used for the ad lib fed animals and 45 mg for the food restricted ob/ob mice (Bio Serv, Frenchtown, N.J.). Mice were given 3 days to acclimate to the environment, during which time some weight loss was observed. After the acclimation period, food restriction or leptin treatment was begun and food intake and body weights were measured periodically.

The food intake of the ob-r group was restricted to 2.8 grams per day. To avoid the possible confounding effects of meal feeding in ob-r we administered their food in a continuous manner. Hanging wire cages were attached to automatic pellet dispensers (Coulbourn Instruments, Allentown Pa.) which delivered one 45 mg pellet every 23 minutes continuously for the period of study. Food restriction began 5 days prior to the start of labeling with $^2H_2O$.

Ob-lep mice received murine leptin at a dose of 2 µg/day (Amgen, Thousand Oaks Calif.) via a 28 day Alzet mini osmotic pump (Alza Corp. Palo Alto Calif.) implanted subcutaneously. The pump delivered a continuous infusion of leptin (0.35 µg/µl) subcutaneously at a rate of 0.25 µl per hour. Leptin treatment also began 5 days prior to the beginning of labeling with $^2H_2O$.

Mice were injected with $^2H_2O$ (deuterated water) at a dose to achieve approximately 2% enrichment in the body water pool. The normal drinking water was then replaced with water enriched to 4% $^2H_2O$. $^2H_2O$ treatment had no impact on food intake or body weight. Twenty-one days following the start of $^2H_2O$ administration, mice were fasted for four hours, anesthetized with isoflurane and exsanguinated via heart puncture. When possible, urine was collected at the same time.

Blood Measurements

Plasma glucose was measured with a YSI (Yellow Springs, Ohio) auto analyzer. Plasma insulin and leptin assays were performed by assay services at Linco research (St. Charles, Mo.).

Adipose Tissue Preparation and Isolation of Adipocytes

Fat pads were isolated and dissected according to the following procedure. The inguinal fat pad was defined as the discreet subcutaneous fat pad beginning at the base of the hind legs and extending up to the rib and back to the spine. The perimetrial fat pad was identified and dissected from the ovary and uterus. Mesenteric adipose was removed by stretching the intestine out and gently pulling the fat and lymph tissue away. Retroperitoneal fat pads were located behind the kidneys and extended down toward the top of the perimetrial pad, the upper limit of the uterus was used as a boundary. For inguinal and retroperitoneal pads, the left and right sides were pooled for analysis.

Bone marrow cells were isolated from the hind limb femur. The bone was cut and the center extruded with Hanks Balanced Salt Solution (HBSS) using a 26-gauge needle. Bone marrow DNA was then isolated using techniques well known in the art (Neese, R. A., Siler, S. Q., Cesar, D., Antelo, F., Lee, D., Misell, L., Patel, K., Tehrani, S., Shah, P., and Hellerstein, M. K. (2001) *Anal Biochem* 298, 189–195).

Immediately following dissection, the fat pads were placed in HBSS with calcium in pre weighed tubes for isolation of mature adipocytes according to the method of Rodbell (Rodbell, M. (1964) *J. Biol. Chem* 239, 375–380). The pads were weighed then minced finely in a glass dish with a razor blade. The minced tissue was placed in 3 mL of HBSS and 300 µL of 1% Type II collagenase (Worthington) was added. Tissue was incubated at 37° for up to 90 minutes. Samples were mixed by gentle pipetting with a cut pipette every 30 minutes. Samples were then spun at 800 rpm for 10 minutes. Centrifugation results in three layers in the tube, with clear lipid on the top, an opaque adipocyte containing fraction in the middle and a solution below that with a pellet of cellular debris and stromal-vascular cells. The adipose cell fraction was carefully removed from the middle fraction and frozen. Subsequent microscopic analysis revealed that this protocol did not completely remove all stromal-vascular components (see discussion).

DNA Isolation and Derivitization from Adipose Cells

The frozen slurry of adipocytes was thawed and 100–200 µL was pipetted in duplicate into sterile pre weighed Eppendorf tubes and lyophilized. The dry weight of the sample was determined and then the samples were digested and DNA isolated using Quiagen DNeasy tissue kits. The yield of DNA from each sample was determined with a Pharmacia Biotec Genequant II spectrophotometer.

Ten to 25 µg of DNA was hydrolyzed to individual ribonucleic acids and isolated deoxyadenosine reduced and acetylated. The resulting pentose-tetraacetate (PTA) derivative in ethyl acetate was injected into the GC/MS for measurement of isotope enrichments of the deoxyribose moiety of DNA.

Derivitization and Analysis of TG, FA and $H_2O$

Samples of adipose TG were taken following the incubation with collagenase. Between 10–20 µL of lipid was removed and frozen in ca. 500 µL heptane containing 0.01% betahydroxytoluene. This solution was extracted with 2 ml chloroform: water (1:1). The aqueous phase was discarded and the lipid fraction was transesterified by incubation with 3N methanolic HCL (Sigma-Aldrich) at 55° C. for 60 min. Fatty acid methyl esters were separated from glycerol by Folch extraction with the modification that water rather than 5% NaCl was used for the aqueous phase. The aqueous phase containing free glycerol was then lyophilized and the glycerol converted to glycerol tri-acetate by incubation with acetic anhydride-pyridine, 2:1, as described elsewhere (Hellerstein, M. K., Neese, R. A., and Schwarz, J. M. (1993) *Am J Physiol* 265, E814–820). The phase containing fatty acid-methyl esters was concentrated under nitrogen and injected directly into the GC/MS.

$^2H_2O$ enrichments in body water were measured in tetrabromoethylene derivitized from plasma samples as described in detail elsewhere (Neese, R. A., Siler, S. Q., Cesar, D., Antelo, F., Lee, D., Misell, L., Patel, K., Tehrani, S., Shah, P., and Hellerstein, M. K. (2001) *Anal Biochem* 298, 189–195.).

GC/MS Analyses

Model 5970 and 5971 GC/MS or 5973 instruments (Agilent, Palo Alto, Calif.) were used for measuring isotopic enrichments of glycerol-triacetate fattyacid-methylesters and tetrabromoethylene. Glycerol-triacetate was analyzed using a DB-225 fused silica column, monitoring m/z 159 and 160 (parent $M_0$ and $M_1$), or m/z 159, 160 and 161 ($M_0$, $M_1$ and $M_2$). Methane chemical ionization (CI) was used with selected ion monitoring. Fatty acid-methyl esters composition was analyzed by flame ionization detection and for $^2$H-enrichment by GC/MS. Tetrabromoacetylene was analyzed using a DB-225 fused silica column, monitoring m/z 265 and 266 (parent $M_0$ and $M_1$ masses). Standard curves of known $^2H_2O$ enrichment were run before and after each group of samples to calculate isotope enrichment.

PTA samples were analyzed for incorporation of deuterium on a HP model 5973 MS with a 6890 GC and auto-sampler (Agilent, Palo Alto, Calif.). Methane CI was used with a 30 m DB-225 column under selected ion monitoring of m/z 245–246 (representing the $M_0$ and $M_1$ masses). Natural abundance, (unenriched) dA samples were measured concurrently and the excess $M_1$ (EM1) abundance in the adipose PTA samples were calculated by difference (subtraction of the $M_1$ abundance measured in the unenriched standard from the $M_1$ abundance in the sample). Bone marrow DNA samples were run simultaneously and used to represent a completely or near-completely turned over tissue for calculating fractional adipose cell replacement.

Calculations

TG Synthesis

The percent of TG newly synthesized during the labeling period was calculated based on the precursor-product relationship, as described supra, using body water enrichment to estimate the maximal or asymptotic enrichment in TG-glycerol. The relationship between body water and the maximal TG-glycerol enrichment has been determined through combinatorial analysis (mass isotopomer distribution analysis MIDA) and by measurement of 100% replaced TG pools after long-term $^2H_2O$ labeling. The glycerol moiety of acylglycerides incorporates $^2H$ from $H_2O$ into 4 out of the 5 hydrogens in its C—H bonds (i.e., n=4 or 80% exchange). With n=4, the asymptotic glycerol $M_1$ enrichment ($A_1^\infty$) is calculated to be $A_1^\infty = -7.4625x^2 + 3.3519x + 0.0007$, where x equals measured body water enrichment, and $M_1$ is calculated as (m/z 159)/(m/z 159+160). The fraction of TG which is newly synthesized is then calculated as:

Fractional synthesis $(f)=EM1/A_1^\infty$.

Estimate of Net Lipolysis

Under steady-state conditions, where the whole-body pool of TG is relatively constant, TG synthesis must be balanced by TG breakdown, i.e., lipolysis. TG synthesis, measured in this manner, can be used to estimate lipolysis, however, if there is non random breakdown of adipose TG (i.e. last in first out).several cycles of TG synthesis and breakdown could have occurred for any newly synthesized TG molecule present. For this reason we term this measurement net lipolysis. Moreover, the animals studied here were gaining fat mass, so that a correction for the change in pool size is required to estimate lipolysis rates from label incorporation measurements:

Net lipolysis=TGsynthesized−TGaccumulated.

In the case of the leptin treated mice in which TG retained was a negative value (i.e., body fat was lost) TG synthesis rate is added to the quantity of TG lost to yield the net lipolysis rate.

DNL (fraction of total and fraction of newly synthesized TG)

MIDA was used to measure fractional DNL for palmitate from adipose TG, as described supra, and in U.S. Pat. No. 5,338,686, herein incorporated by reference in its entirety. $^2H_2O$ labeling was used.

The calculated fractional DNL measured by MIDA represents the fraction of stored TG that was synthesized via the DNL pathway during the labeling period. This value does not represent the proportion of DNL in newly synthesized fatty acid stored, however, to the extent that pre-existing fat is present. That is, "non-DNL" TG could represent either pre-existing TG or newly synthesized TG from non-DNL pathways. This problem can be solved by correction for the proportion of TG that is newly synthesized. The ratio of DNL-f to TG-f reveals the true fraction from DNL in new fat storage. If the fractional DNL contribution is 35% and the fractional TG synthesis is 70% the true fractional DNL in newly synthesized TG is 0.35/0.7 or 50%, rather than the 35% f measured directly.

Absolute palmitate DNL was calculated by multiplying fractional DNL by 0.8 times the weight of the fat pad (the estimated fraction of TG in adipose tissue) then by the percent palmitate present (measured by flame ionization detection). This value represents the absolute amount (grams) of palmitate synthesized during the labeling period.

Adipose Cell Proliferation (Adipogenesis)

Fractional adipose cell proliferation was calculated as the $EM_1$ in adipose DNA divided by $EM_1$ in bone marrow DNA. The bone marrow DNA is used here to estimate the $A_1^\infty$ value in adipose DNA since bone marrow cells are nearly completely replaced after 7 days in mice. Absolute adipose cell synthesis was calculated by multiplying the fractional synthesis by the total number of cells.

Results

Figure 6:
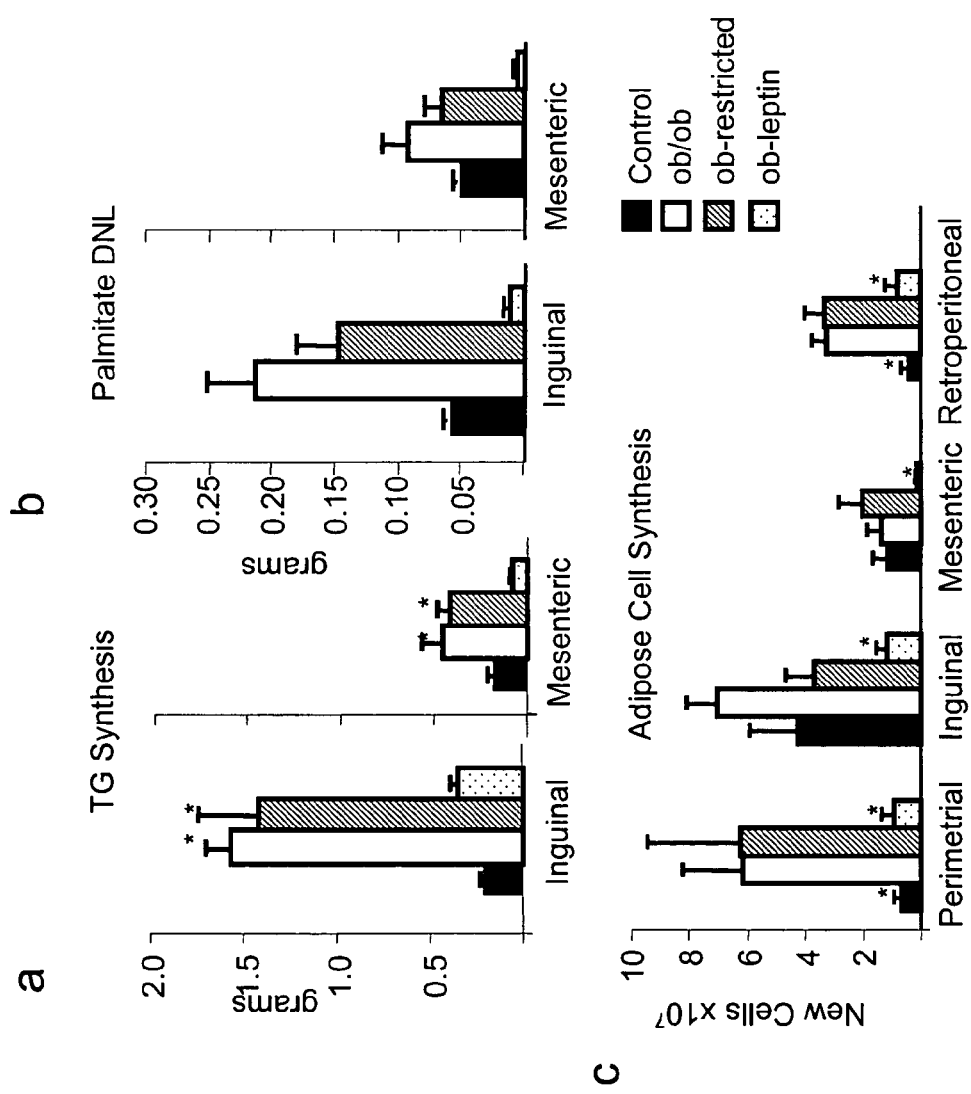
FIG. 6 depicts the dynamics of adipose metabolic components in ob/ob mice and controls measured simultaneously in two different adipose depots (inguinal and mesenteric) for TG and palmitate synthesis (marker of de novo lipogenesis or DNL) and four different compartments (perimetrial, inguinal, mesenteric, and retroperitoneal) for adipocyte cell proliferation. In panel a), the effects of triglyceride synthesis are shown. In panel b), de novo lipogenesis is shown. In panel c) adipocyte proliferation is shown. The effects of food-restriction (pair-feeding) and leptin administration are compared in this manner.

FIGS. 5 and 6 show the results indicating that three separate metabolic pathways (de novo lipogenesis, adipogenesis, and triglyceride synthesis) were measured concurrently in the same experiment. Leptin deficiency and replacement influenced all three pathways similarly, showing for the first time the coordinated effect of leptin on these aspects of adipose tissue metabolism.

Example 5

Lung Collagen Synthesis vs. Fibroblast Proliferation (DNA Synthesis) in Pulmonary Interstitial Fibroblasts (PIF).

PIF is a disease characterized by progressive replacement of lung by scar tissue (collagen). The inflammatory or fibrogenic signals for collagen deposition by pulmonary fibroblasts are unknown. The pathogenesis and therapy of PIF may differ between individuals with a large number of activated fibroblasts vs. a normal number of intrinsically more hypersynthetic fibroblasts. This distinction may be apparent by comparing the rates of lung collagen synthesis from $^2H_2O$ to the rates of lung fibroblast proliferation (DNA synthesis) from $^2H_2O$. A high ratio (collagen:DNA) would indicate hypersynthetic fibroblasts; a low ratio with high absolute values for each parameter would indicate generalized activation of fibroblasts. Both collagen and DNA synthesis are measured concurrently by administering labeled water and detecting the incorporation of the isotope label in collagen and DNA.

Example 6

Ratio of Protein to mRNA and mRNA to DNA Synthesis Rates in a Tissue.

The relative molecular flux rates of protein to mRNA synthesis reflects whether translational vs. transcriptional control is responsible for changes in the expression of a protein by a tissue. Similarly, the relative rates of RNA to DNA synthesis by a tissue distinguishes between transcriptional effects vs. cell division as the mechanism responsible for a change in total mass or expression of a protein in a tissue. These rates (protein, mRNA, DNA) are measured concurrently by administering labeled water and detecting the incorporation of the isotope label in protein, mRNA, and DNA.

Example 7

Rates of, Triglyceride and Fatty Acid Input into Lipoproteins Assembled by the Liver.

The assembly of very-low-density-lipoprotein (VLDL) particles in the liver underlies many forms of hyperlipidemia and is the target for hypolipidemic therapies. Hepatic VLDL assembly involves the synthesis of several classes of molecules (ApoB, cholesterol, cholesterol-esters, triglycerides, phospholipids), some of which themselves involve more than one biosynthetic pathway (e.g., synthesis of fatty acid and acyl-glyceride moieties in the assembly of triglyceride and phospholipids; synthesis of cholesterol and fatty acid moieties in the synthesis of cholesterol-esters). Different varieties of human hyperlipidemias appear to be due to alteration in different pathways on this list. The form called familial dyslipidemic hypertension (or hyperapobeta lipoproteinemia) is due to excessive secretion of ApoB. Other forms, such as carbohydrate-induced hyperlipidemias may reflect changes in rates of triglyceride synthesis, fatty acid synthesis, or removal of triglycerides from VLDL. The production rates of all of these components are measured concurrently by administering labeled water and detecting the incorporation of the isotope label in each of the biological molecules.

Example 8

De Novo Lipogenesis Contribution to Adipose Fat Accrual Corrected for New Adipose Triglyceride Synthesis.

The contribution from de novo lipogenesis (DNL) or endogenous synthesis of new fatty acids (such as palmitate by the body) compared to dietary fat intake (ingestion of fatty acids) represents a key distinction in the physiology of body fat accumulation (e.g., obesity). The enzymes responsible for de novo lipogenesis, and therefore the drug treatment indicated, differ for the endogenous vs. dietary forms of body fat accrual. Direct measurement of the de novo lipogenesis fractional contribution to adipose triglycerides does not reveal the true proportional contribution because the total triglyceride deposition rate must be known. For example, if the measured value reveals that 5% of adipose palmitate derived from the de novo pathway, this might represent 100% of newly synthesized palmitate (if only 5% of the total TG in the tissue was new) or 5% of newly synthesized palmitate (if 100% of the total TG in the tissue were new). Correcting the de novo lipogenic contribution for the replacement fraction of triglyceride in the tissue (i.e., calculating the ratio of new fatty acid synthesis to new triglyceride synthesis) allows calculation of the true contribution from the de novo synthesis to new stored lipids). These measurements are performed concurrently as disclosed herein and indicated in the data, infra.

Healthy subjects were recruited by advertisement. Entrance criteria included weight stability for >3 months, body mass index <28 kg/M$^2$; absence of infectious or inflammatory conditions within the previous 3 months; good general health, normal screening laboratory tests (chemistry profile, complete blood count), HIV-seronegativity; ability to give informed consent. Exclusion criteria consisted of prior history of metabolic disorder (diabetes, obesity, hyperlipidemia) or other organ system disease (liver, kidney, lung, etc.); use of medications with potential metabolic effects (glucocorticoids, β-blockers, thiazide diuretics, phenytoin, adrenergic agents, androgens, anabolic agents, estrogens, or oral contraceptives); inability to give informed consent. A total of 19 subjects entered the study. Two groups of healthy subjects were enrolled: group 1 took the $^2$H$_2$O for 9 weeks (n=9); group 2 (n=10) to the $^2$H$_2$O for 5 weeks. We included subjects with a range of body fat, waist-to-hip ratios, and blood metabolite measurements in this initial survey study, with the intent of introducing variability for adipose tissue kinetic parameters. Five men and four women were studied in group 1, while group 2 consisted of ten men. Body weight was measured at the beginning of the study, then every 2–3 weeks. Body composition was measured by bioelectrical impedance analysis at the beginning and end of the $^2$H$_2$O labeling study. Blood concentrations were measured by the SF General Hospital Clinical laboratories. All studies and procedures received prior approval from the UC Berkeley and UC San Francisco Committees on Human Research, and subjects gave written informed consent before participating.

H$_2$O Labeling Protocol

The $^2$H$_2$O was administered orally. The initial priming dose was carried out in the General Clinical Research Center (GCRC) of SF General Hospital. Subjects received a total of 350–400 mL of $^2$H$_2$O in the GCRC, given as divided doses over the course of 18–21 hours (70 mL of 70% $^2$H$_2$O, given every 3–4 hours), to achieve about 1.0% enrichment in the body water pool. The $^2$H$_2$O was purchased from Isotec, Inc. (Miamisburgh, Ohio) and dispensed in sterile containers. Subjects then took 50 mL of 70% $^2$H$_2$O three times a day for 5 days, then 35–50 mL twice-a-day for the remainder of the 8–10 week labeling protocol. This protocol achieves near-plateau body $^2$H$_2$O enrichments (1.5–2.0%, see below) within 5–7 days in most subjects and was well-tolerated. Subjects received the $^2$H$_2$O as individual aliquots (35–50 mL of 70% $^2$H$_2$O) in plastic vials, which were stored in the refrigerator.

Compliance with outpatient $^2$H$_2$O intake was checked through weekly visits (for urine and saliva collection) and by return of vials for counting.

Collection of Body Water Samples and Blood for Monocytes

Plasma or urine samples were collected weekly in all subjects and frozen in closed containers. Blood was collected in Ficoll-Hypaque solution and the mononuclear fraction removed, after centrifugation. Blood monocytes were isolated as CD14$^+$ cells by immunomagnetic beads.

Adipose Tissue Sampling Protocol and Isolation of Mature Adipocyte-Enriched Fraction Adipose tissue aspiration biopsies were performed at weeks 5 and 9 of $^2$H$_2$O intake, using the procedure described elsewhere (Neese, R., L. Misell, S. Turner, A. Chu, J. Kim, D. Cesar, R. Hoh, F. Antelo, A. Strawford, J. M. McCune, and M. Hellerstein. Measurement in vivo of proliferation rates of slow turnover cells by $^2$H$_2$O labeling of the deoxyribose moiety of DNA. *Proc Natl Acad Sci USA* 99(24): 15345–50, 2002). In brief, three subcutaneous sites were sampled at each visit—the gluteal region (buttocks), femoral region (thigh), and flank region (mid-back). For the fat aspiration procedure, lidocaine topical anesthetic (1%, with epinephrine 1:100,000) was used. Subcutaneous fat was aspirated with a 14-gauge needle into a 3 cc syringe and then placed in sterile tubes over ice for processing (on the same day). Tissue samples were minced with a sharp blade then treated with type 2 collagenase (Worthington, Lakewood N.J.). One mL of a 2 units/μL solution was added to each adipose sample and allowed to incubate for 1 hr at 37° C. The cell suspension was then poured slowly over a 350 μm mesh filter (Spectrum Laboratories, Rancho Dominguez Calif.). Adipose cells in the filtrate were then collected and processed for lipid isolation and microscopic analysis.

Isolation of Metabolites for Mass Spectrometric Analyses
TG-glycerol and Fatty Acids Tissue samples were placed in Kontes dual glass tissue grinders (Kimble Kontes, Vineland, N.J.) with 1 mL methanol:chloroform (2:1) and ground until homogenous, then centrifuged to remove protein. This solution was extracted with 2 mL chloroform:water (1:1). The aqueous phase was discarded and the lipid fraction was transesterified by incubation with 3N methanolic HCL (Sigma-Aldrich) at 55° C. for 60 min. Fatty acid methyl esters were separated from glycerol by Folch extraction with the modification that water rather than 5% NaCl was used for the aqueous phase. The aqueous phase containing free glycerol was then lyophilized and the glycerol converted to glycerol tri-acetate by incubation with acetic anhydride-pyridine, 2:1 (32).

Body $H_2O$ $^2H_2O$ enrichments in body water were measured from plasma or urine. A 15–20 µL sample was reacted in an evacuated GC vial with calcium carbide to produce acetylene. The acetylene gas was then transferred with a syringe and injected into an evacuated GC vial containing 10% bromine in carbon tetrachloride and incubated at room temperature for 2 hours to produce tetrabromoethane. Excess bromine was neutralized with 25 µL 10% cyclohexene in carbon tetrachloride. The tetrabromoethane, containing hydrogen atoms from body $H_2O$, was then analyzed by GC/MS.

GC/MS Analyses

TG-glycerol Fatty Acids and $H_2O$

Model 5970 and 5971 GC/MS or 5973 instruments (Hewlett-Packard Inc., Palo Alto, Calif.) were used for measuring isotopic enrichments of glycerol, fatty acids and $H_2O$.

Glycerol-triacetate was analyzed using a DB-225 fused silica column, monitoring m/z 159 and 160 (parent $M_0$ and $M_1$), or m/z 159, 160 and 161 ($M_0$ to $M_1$ and $M_2$). Methane chemical ionization was used with selected ion monitoring. Fatty acid methyl esters were analyzed for composition by flame ionization detection and for $^2H$ enrichment by GC/MS, as described elsewhere (Hellerstein, M. K., M. Christiansen, S. Kaempfer, C. Kletke, K. Wu, J. S. Reid, K. Mulligan, N. S. Hellerstein, and C. H. Shackleton. Measurement of de novo hepatic lipogenesis in humans using stable isotopes. *J Clin Invest* 87: 1841–52, 1991).

Tetrabromoethane was analyzed using a DB-225 fused silica column, monitoring m/z 265 and 266 ($M_0$ and $M_1$ masses of the 79Br79Br81Br [parent-OAc] isotopomer). Standard curves of known enrichment were run before and after each group of samples to calculate isotope enrichment.

GC/MS Analytic Procedures

For all GC/MS analyses, enriched samples were abundance-matched with baseline (unenriched) samples. The abundance range used was that which gave values within 1–2% of theoretical mass isotopomer ratios, as described elsewhere (Neese, R. A., S. Q. Siler, D. Cesar, F. Antelo, D. Lee, L. Misell, K. Patel, S. Tehrani, P. Shah, and M. K. Hellerstein. Advances in the stable isotope-mass spectrometric measurement of DNA synthesis and cell proliferation. *Anal Biochem* 298: 189–95, 2001.). Only analytic runs for which baseline abundances achieved these accuracy levels and for which samples fell within this abundance range were considered acceptable for use in calculations.

Statistical Analyses

Group comparisons were by ANOVA. Statistically significant differences were taken to be p<0.05. Sources of variability in the measurements were assessed by using random effects models. These included random person effects (that reflect between-person variability), random depot effects within each person (that reflect depot-to-depot variation) and residual week-to-week effects (that reflect week-to-week variability within each depot for each subject). These models also included a fixed week effect to account for systematic change over time. Correlations between adipose TG kinetic parameters and standard (non-kinetic) parameters were also analyzed, using regression models. Pearson correlation and Spearman rank correlation coefficients were calculated for fractional TG synthesis, absolute TG synthesis, DNL and lipolysis vs plasma insulin, glucose, and triglyceride concentrations, percent body fat, total body fat, and waist:hip ratio.

Results

Adipose Tissue TG Turnover

The synthesis and replacement rates of adipose tissue TG were measured from the incorporation of $^2H$ into TG-glycerol. Incorporation into TG-glycerol increased over the course of 9 weeks. Fractional synthesis (f) was ca. 0.12–0.15 (12–15%) after 5 weeks in the 3 depots sampled and 0.16–0.22 (16–22%) after 9 weeks. Fractional replacement rates of adipose TG were in the range of 0.0030–0.0045 $d^{-1}$, indicating relatively consistent values of $t_{1/2}$ for adipose TG of around 200–250 d.

Adipose TG synthesis rate appeared to increase somewhat more slowly between weeks 5 to 9 than during the first 5 weeks of label administration. In the subjects matched for biopsies at both time points, f was 0.130±0.048% (wk 5) and 0.158±0.057 (wk 9) for gluteal depot, 0.151±0.098 and 0.236±0.127, respectively, for flank, and 0.125±0.042 and 0.205±0.099, respectively, for thigh. Week 9 values were significantly higher than week 5 values (p<0.05).

The total amount of adipose TG synthesized and retained over five weeks was calculated to be 1.80±0.98 kg (n=18), with a range between 0.5 to 4.4 kg. The average rate of adipose TG synthesis (assuming the subcutaneous depots sampled here are representative of total body fat stores) is therefore about 0.35 kg per week, or 50 g per day.

Lipolysis rate could also be calculated, based on TG synthesis and body fat balance. Because these subjects were in zero fat balance at the whole-body level (weight stable and no change in body composition over the 9-week labeling period), net lipolysis equals net synthesis, or replacement, of adipose TG. The net lipolysis rate was calculated from the average value of k in the three depots sampled for each subject, multiplied times the whole-body fat pool size (average ca. 15 kg in these subjects). These values were about 50–60 g TG/day, or ca. 0.4–0.6 mg TG/kg body weight/min.

Contribution from DNL to Adipose Tissue TG

Incorporation into TG-FA increased in a roughly linear manner between weeks 0 to 9. Fractional DNL (fDNL) reached an average of 0.020±0.01.2 in gluteal fat (n=17), 0.023±0.016 in flank fat (n=17) and 0.025±0.013 in thigh fat (n=12), after 5 weeks of $^2H_2O$ labeling. After 9 weeks of $^2H_2O$ labeling, fDNL values were 0.040±0.025 in gluteal fat (n=8), 0.041±0.024 in flank fat (n=6) and 0.041±0.024 in thigh fat (n=8). When corrected for the fraction of adipose TG that was newly deposited (i.e., correcting for TG-glycerol synthesis), the fractional contribution from DNL to newly deposited TG-palmitate was relatively constant over time and among depots within most individuals with an average value of about 20%. Individuals appeared to be on their own characteristic curve, however, with consistent results within each individual over time and for all depots tested.

The approach described in this Example allows concurrent (i.e., simultaneous) measurement of adipose tissue TG synthesis, net lipolysis (TG breakdown), and contribution from the DNL pathway integrated over long periods of time (i.e., weeks or months) in human subjects. Moreover, because outpatient intake of heavy water is simple, easy to comply with and relatively inexpensive, this approach has a number of practical advantages over alternative methods for estimating dynamics of adipose tissue components in humans.

Example 9

Effects of Aerobic Exercise on Mitochondrial Cardiolipin: DNA Synthesis Rates.

Mitochondrial biogenesis in muscle occurs in response to aerobic exercise (see above). Mitochondrial biomolecules include not only mtDNA but also membranes rich in phospholipids, in particular a molecule relatively unique to mitochondria—cardiolipin (CL). The integrated biogenesis of cellular organelles such as mitochondria requires coordinated synthesis of mtDNA, mitochondrial cardiolipin and mitochondrial proteins. CL contains 3 glycerol moieties and is therefore ideal for the application of $^2H_2O$ labeling of the glycerol moiety of acylglycerides. The initiation of an exercise regimen in rats results in stimulation of mitochondrial CL as well as mtDNA synthesis and the two parameters correlate well. Accordingly, measurement of mitochondrial CL synthesis may be useful (as a more sensitive approach than mtDNA) in assessment of aerobic training status and regimens. The finding of parallel changes in mitochondrial CL and mtDNA greatly strengthens either finding by itself. The finding of a dissonance between the two measured synthetic rates would suggest the need to re-evaluate the result or to look for a new cause of this finding. The molecular flux rates of mtDNA and mitochondrial CL are measured concurrently (i.e., simultaneously) by administering isotope labeled water and detecting mtDNA and mitochondrial CL by mass spectrometry.

Briefly, 3 month old female Sprague-Dawley rats were randomly assigned into control (no exercise) or experimental (free access to running wheels) groups. Animals were caged individually in wire bottom cages and fed AIN-93M diet. Animals were bolused with 99% $^2H_2O$ to 5% enrichment 8 days prior to sacrifice and maintained on 8% drinking water. After 4 weeks the animals were sacrificed and red gastrocnemius, heart, and blood were collected. Mitochondria were isolated from fresh tissue via differential centrifugation. The mitochondria were equally alloquoted into 2 separate tubes for later mtDNA and phospholipid (cardiolipin and phosphatidylcholine) analysis. Plasma was used to assess body water $^2H_2O$ enrichment. Cardiolipin and phosphatidylcholine were measured concurrently using the methods of the present invention described, supra. Cardiolipin and mtDNA were also measured concurrently (i.e., simultaneously), using the methods of the present invention as described, supra.

Figure 12:
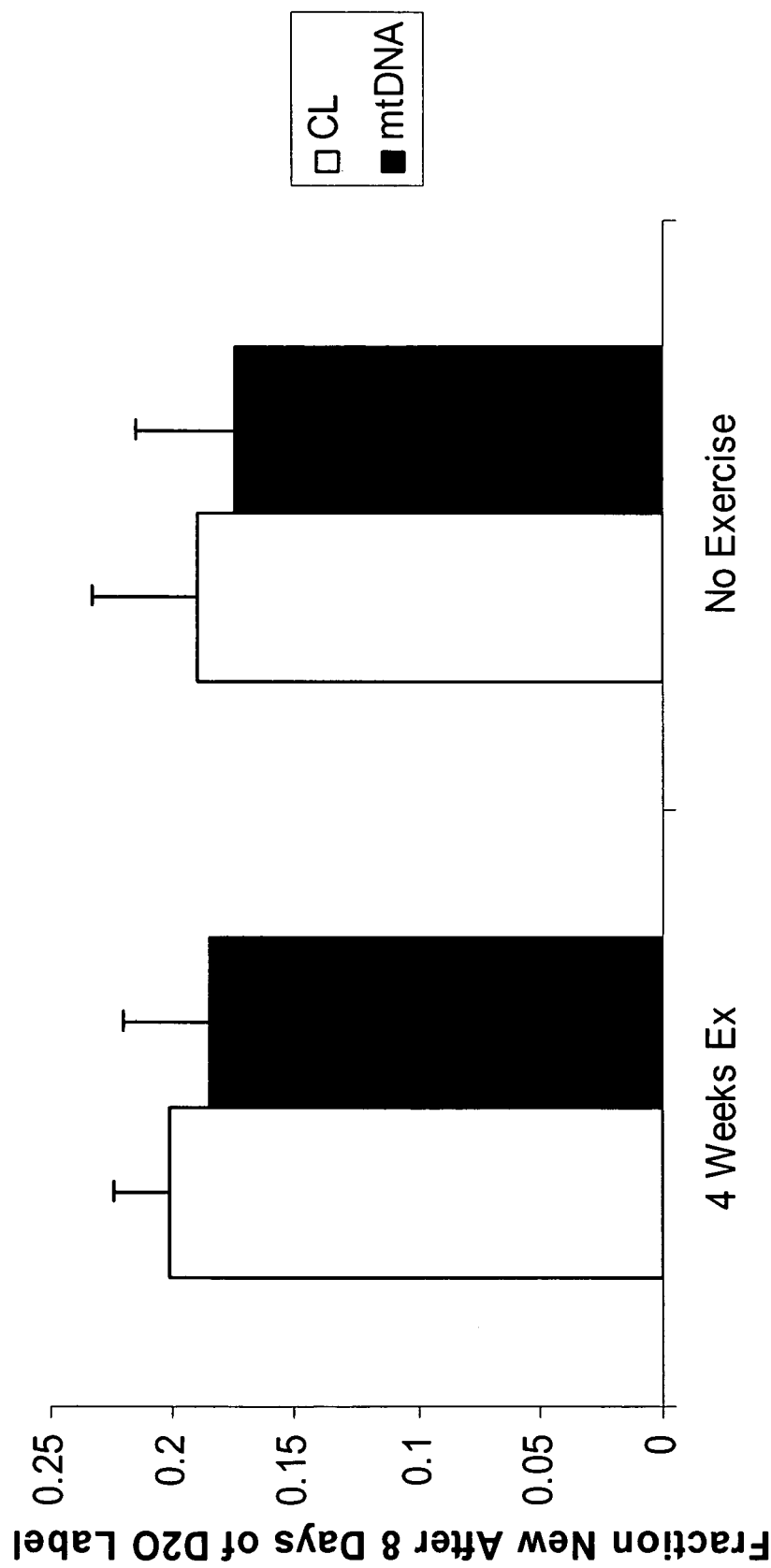
FIG. 12 depicts fractional synthesis of cardiolipin and mtDNA in the mitochondrial red gastrocnemius of female Sprague Dawley rats. Cardiolipin and mtDNA were measured simultaneously. Ex=exercise. Although no changes were observed in mice having exercised for four weeks versus mice that were sedentary during that same time period, cardiolipin was shown to be equivalent to mtDNA as a biomarker of mitochondrial biogenesis.
Figure 13:
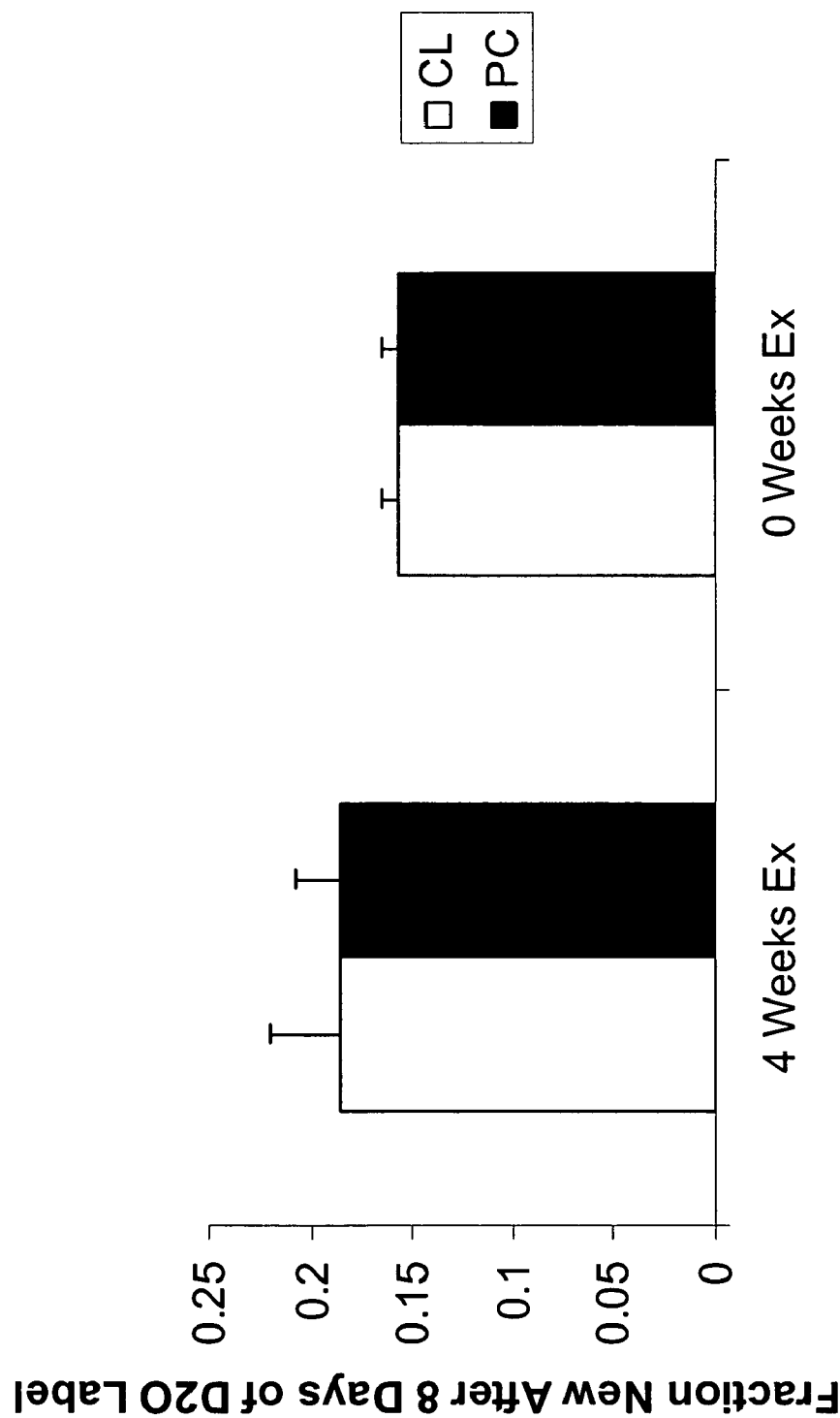
FIG. 13 depicts the fractional synthesis of cardiolipin and phosphatidylcholine in the mitochondrial heart of female Sprague Dawley rats. Cardiolipin and phosphatidylcholine were measured simultaneously. Ex=exercise. Although no changes were observed in mice that exercised for four weeks versus mice that were sedentary during that same time period, phosphatidylcholine was shown to be equivalent to cardiolipin as a biomarker of mitochondrial biogenesis.

FIGS. 12 and 13 show the ratio between three biomarkers of mitochondrial biogenesis including mt DNA, cardiolipin, and phosphatidylcholine. FIG. 12 shows that cardiolipin, when compared to mtDNA synthesis, is equivalent to mtDNA as a biomarker of mitochondrial biogenesis. Similarly, FIG. 13 shows that phosphatidylcholine is equivalent to cardiolipin, demonstrating that all three biomarkers are useful in determining mitochondrial biogenesis. The methods allow for two or more simultaneous measurements of these biomarkers to determine mitochondrial biogenesis. Changes in one biomarker, relative to another or both of the other biomarkers, may provide useful information for diagnosing metabolic diseases or conditions involving changes in mitochondrial biogenesis or for measuring therapeutic activity of compounds tested for stimulating or inhibiting mitochondrial biogenesis.

Example 10

T Cell DNA vs. Plasma Immunoglobulin Synthesis.

The cellular immune system and the humoral immune system represent discrete arms of the body's host defense system. The former is reflected by activation and proliferation of T lymphocytes the latter by synthesis of antibodies (immunoglobulins) by B lymphocytes. It is often important to know which arm of the immune system is activated or suppressed in a disease state or by a drug treatment. Comparison of the proliferation rates of T cells (measured from T-cell DNA synthesis) to the synthesis rates of plasma immunoglobulins represents a measure of cellular:humoral immune activation. The molecular flux rates of T cell DNA and immunoglulins are measured concurrently (i.e., simultaneously) by administering isotope labeled water and detecting T cell DNA and immunoglobulins by mass spectrometry. Antigen-specific T-cells and/or immunoglobulins are also measured as described above.

Example 11

Mammary Epithelial Cell and Endometrial Cell Proliferation vs. Bone Collagen Breakdown and Brain Amyloid-beta Production During Treatment with Selective Estrogen Receptor Modulators (SERMs).

SERMs are receiving a great deal of attention as potential therapies to improve women's health. The effects of estrogen differ greatly for different tissues, however, and the risk:benefit balance in an individual woman depends upon these opposing actions. Estrogen tends to increase proliferation of mammary epithelial cells and endometrial cells (thereby increasing risk for breast cancer and uterine cancer) while reducing breakdown of bone collagen (thereby reducing the risk of osteoporosis) and possibly reducing the proliferation of brain amyloid-beta protein (thereby reducing the risk of Alzheimer's Disease). SERMs might be designed that oppose the cell proliferative action but stimulate or leave unchanged the other actions. Those agents would then have great public health and commercial utility. A means of screening for the optimal combination of actions would clearly be useful. All the processes noted (replication of mammary epithelia and endometrial cell DNA, kinetics of bone collagen and brain amyloid-beta) are measured concurrently (i.e., simultaneously) as described herein.

Example 12

Dermal Collagen vs. Elastin Synthesis and Breakdown in Skin Photo-aging

Skin wrinkles are increased by exposure to sunlight. This area represents a very large commercial field in cosmetic and drug research. The biochemistry of skin wrinkles (photoaging) is well characterized, and consists of reduced dermal-layer collagen (due to reduced synthesis and increased breakdown) and increased elastin or other proteins (due to increased synthesis). The ratio of dermal collagen synthesis or breakdown to dermal elastin synthesis might therefore reflect a direct marker of photoaging, for testing anti-wrinkle treatments in a high-throughput manner in animal models (e.g., hairless mouse) and humans. Syntheses of these molecules are measured concurrently (i.e., simultaneously) by administering labeled water and comparing the relative molecular flux rates of dermal collagen and elastin by mass spectrometry.

Example 13

Keratin Turnover (Protein) vs. Keratinocyte Proliferation (DNA) in Psoriasis

Psoriasis is a common chronic, recurrent disease characterized by dry, well-circumscribed, silvery, scaling papules and plaques of various sizes. It varies in severity from one or two lesions to widespread dermatosis, sometimes associated with disabling arthritis or exfoliation. The cause is unknown, but the thick scaling has traditionally been attributed to increased epidermal cell proliferation and concomitant dermal inflammation. Typical lesions are sharply demarcated, variously pruritic, ovoid or circinate erythematous papules or plaques covered with overlapping thick silvery micaceous or slightly opalescent shiny scales. Erythrodermic psoriasis (exfoliative psoriatic dermatitis) may be refractory to therapy. The entire cutaneous surface is red and covered with fine scales; typical psoriatic lesions may be obscured or absent. It may lead to general debility and a need for hospitalization.

Keratins are a family of more than 50 structural proteins with a common architecture. Several keratins are expressed in skin and form the major protein component of epidermis. Basal cells of the epidermis produce daughter cells which migrate toward the skin surface, maturing until they contain little but keratins K1 and K10 and lipid. These cells ultimately die forming the many layered protective outer skin surface, the stratum corneum. In healthy human skin it takes on average about four weeks from the synthesis of new keratin until it is sloughed off at the skin surface. Psoriasis is characteristically marked by hyperproliferation of the epidermis; transit time of epidermal keratin and keratinocyte may therefore take a few days rather than several weeks.

Keratin provides an accessible marker of skin turnover. Keratin turnover can be monitored by two methods. In one, whole epidermis is isolated from a skin sample using a simple proteolytic treatment; in the second, tape strips with a specially designed adhesive are applied to the skin surface and the outermost non-living tissue is removed a single layer at a time. Labeled keratin begins to appear quickly in whole epidermis upon administration of deuterated water but it takes about two and a half weeks before any label appears at the surface of normal human skin monitored by tape strips. At least 30 sequential tape applications are required to reach the underlying living portion of the epidermis in normal skin.

Keratins are very insoluble which makes it easy to isolate the keratin fraction from other proteins in the skin. The same procedure works well on both whole epidermis and tape strips. First, the samples are extracted in a high salt buffer containing Triton X-100. This dissolves essentially all epidermal proteins except keratins. Keratins are then solubilized by boiling in sodium dodecyl sulfate. Although hair is also composed of keratins (with a slightly different structure), hair keratins are not solubilized by this method and do not contaminate the samples. Virtually pure skin keratins are produced by this simple extraction.

Figure 7:
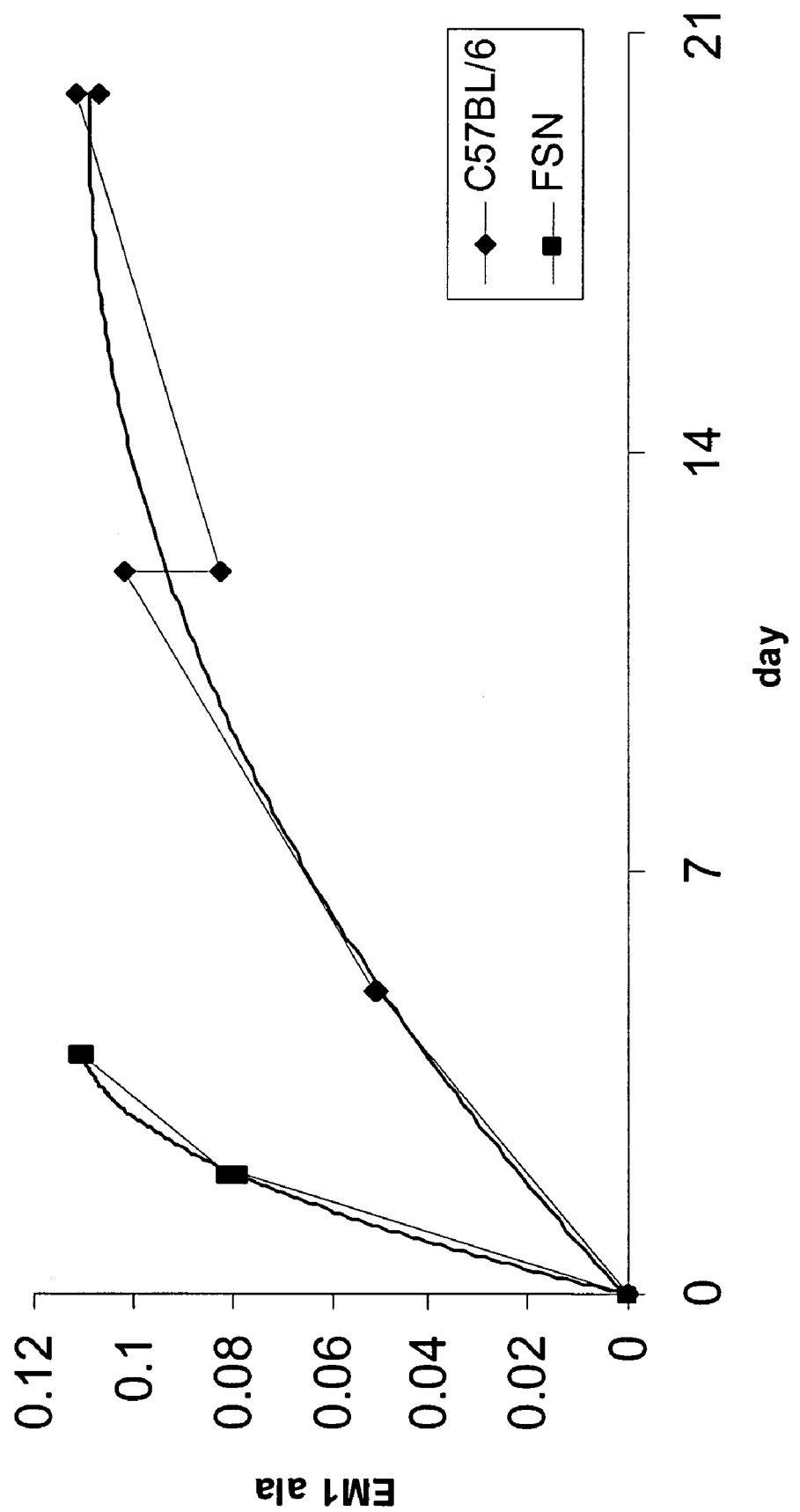
FIG. 7 depicts skin keratin turnover in normal (C57bl/6 mice) and flaky skin mice (FSM or "flaky skin mouse," a mouse model of psoriasis) as indicated by EM1 enrichments of alanine in keratin in the two different mouse species measured simultaneously and measured simultaneously with keratinocyte DNA synthesis in both mouse species as depicted in FIG. 8. As FIG. 7 shows, keratin turnover is much more rapid (steep curve on the left) in the mouse model of psoriasis than keratin turnover (shallower curve on the right) in the normal mouse.
Figure 8:
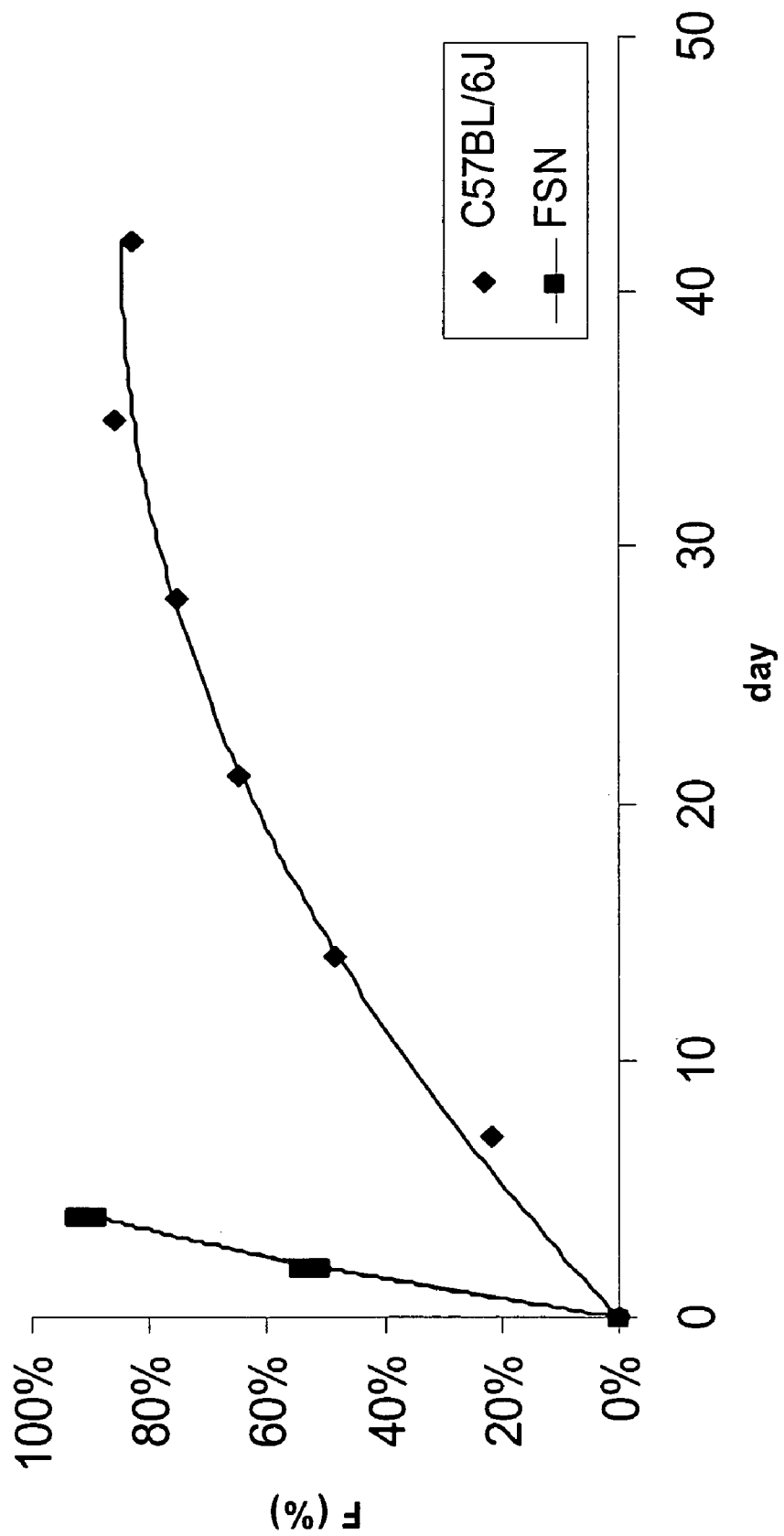
FIG. 8 depicts keratinocyte turnover (de novo DNA synthesis) in normal (C57bl/6 mice) and flaky skin mice (f%=fractional synthesis of DNA). Keratinocyte turnover was measured concurrently in both mouse species and with skin keratin turnover in both mouse species (skin keratin turnover depicted in FIG. 7).

Normal mice given deuterated water do not achieve plateau deuterium enrichments in skin keratin for several weeks (FIG. 7). By contrast, Flaky Skin (FSN) mice, a psoriasis model with hyperproliferative skin, approach full keratin turnover in just four days. A similar contrast of normal vs. FSN mice is seen in epidermal keratinocyte proliferation (FIG. 8). Keratin measurements (FIG. 7) and keratinocyte de novo DNA synthesis (FIG. 8) were measured concurrently (i.e., simultaneously). The parallel changes in keratin and keratinocyte kinetics confirm the hyperproliferative state present within the tissue.

Example 14

Comparing Actions of Chemotherapeutic Agents in Different Tissues

Figure 9:
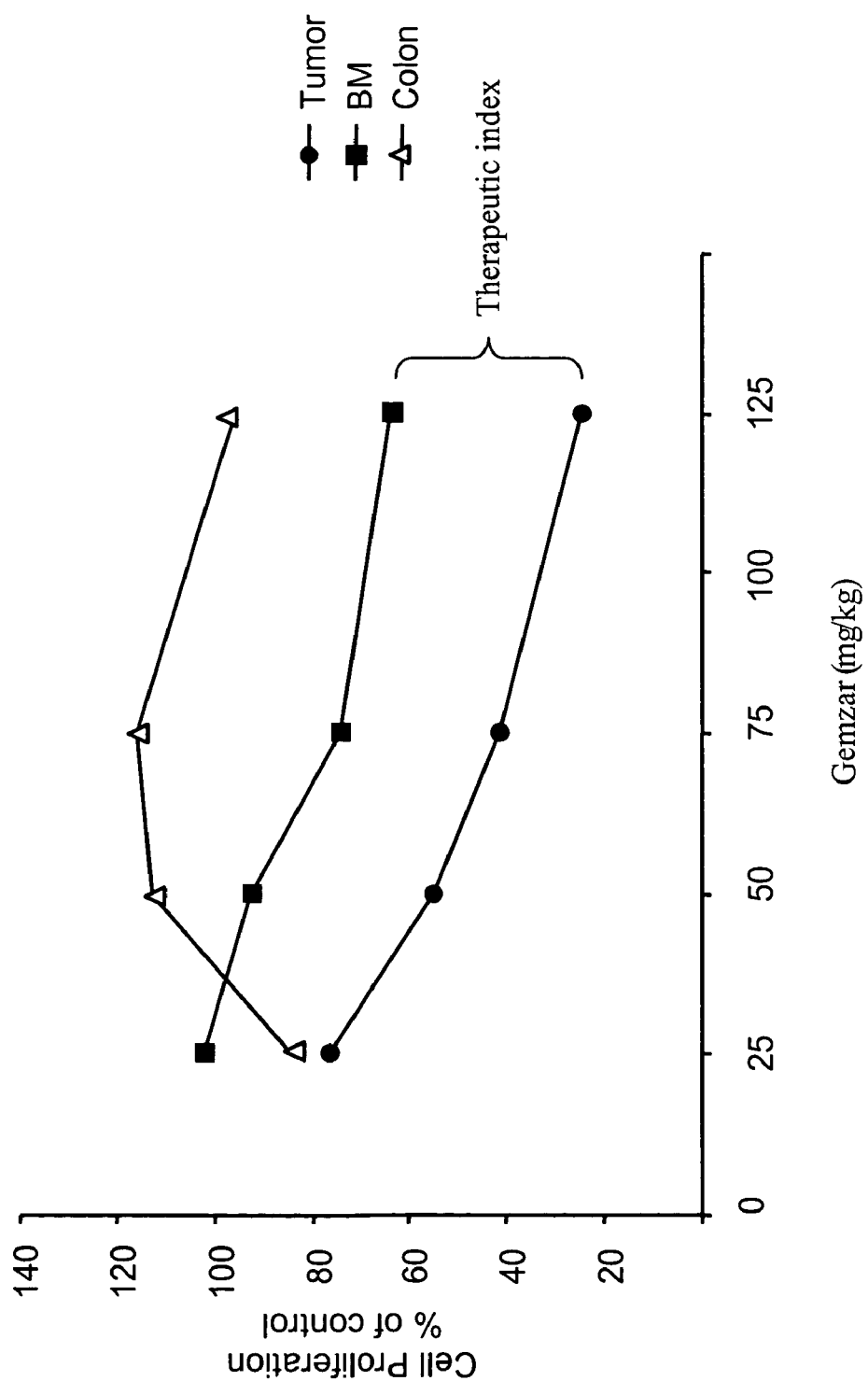
FIG. 9 depicts the simultaneous measurement of cell proliferation in tumor cells, colonocytes, and bone marrow cells after exposure to increasing doses of Gemzar (gemcitabine) in male balb/C nu/nu mice. As FIG. 9 shows, increasing doses of Gem inhibits tumor and bone marrow cell proliferation but exerts relatively little effect on colon cell proliferation (Gem may have a stimulatory effect on colonocyte proliferation at the lower experimental doses).

Male balb/C nu/nu mice were implanted subcutaneously with non-small cell lung carcinoma cells (SW1573) cells in matrigel. Mice were labeled with $^2H_2O$ and treated with increasing doses of gemcitabine (Gem), administered every other day (as shown in FIG. 9). After 5 days, tumor, colon and bone marrow were removed using techniques well known in the art, and as described, supra. Cell proliferation was measured as described, supra. The data indicate that cell proliferation was inhibited in tumor and bone marrow cells in a dose-response manner, whereas colonocytes exhibited little inhibition. De novo DNA synthesis from all three cell types was measured concurrently using the methods of the present invention. Briefly, heavy water ($^2H_2O$) is administered to living organisms (8% $^2H_2O$ in drinking water). DNA is isolated, hydrolyzed to free dNs, and deuterium incorporation into the deoxyribose (dR) moiety of purine and pyrimidine dNs is measured by gas chromatography/mass spectrometry (GC/MS) as described, supra. The label content in dA reveals the de novo DNA synthesis (cell proliferation).

Figure 10:
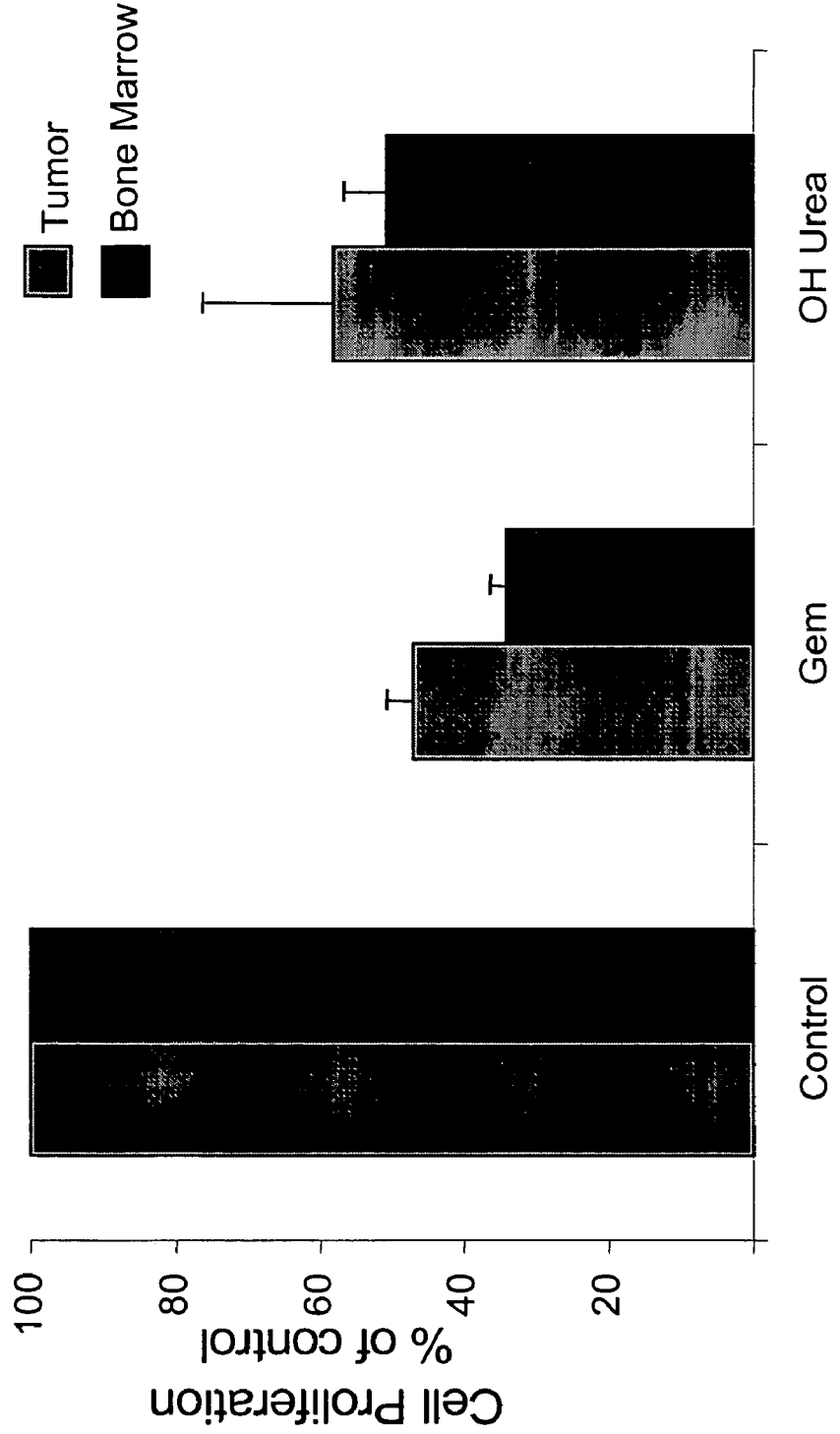
FIG. 10 depicts the in vivo inhibition of cell proliferation, relative to control animals, of Gem and hydroxyurea (HU) on tumor and bone marrow cells in female balb/C nu/nu mice. Hydroxyurea is a well known inhibitor of DNA synthesis and is a widely prescribed chemotherapeutic agent. As FIG. 10 shows, both Gem and HU decreased cell proliferation in bone marrow cells and tumor cells relative to saline-administered control mice.

Female balb/C nu/nu mice were implanted subcutaneously with approximately $10^6$ EMT7 mouse mammary carcinoma cells in matrigel. Tumors were allowed to reach ca. 1500 mm$^3$ in size. Mice were labeled with $^2H_2O$ and treated with either 125 mg/kg gemzar (gemcitabine or Gem) or 500 mg/kg hydroxyurea (HU). Gem was administered every other day; HU daily; and control saline daily. At the end of 5 days tumors were removed and cell proliferation was measured as described, supra. The data are depicted in FIG. 10. As FIG. 10 shows, Gem and HU caused reductions in cell proliferation in both tumor and bone marrow cells, relative to cells administered the control saline solution. De novo DNA synthesis from both cell types was measured concurrently (i.e., simultaneously) using the methods of the present invention as described, supra.

Nude mice were implanted with human SW1573 lung cancer cells ($5\times10^6$ cells/animal), injected with varying doses of paclitaxel, and labeled with $^2H_2O$ for 24 hours. Both vehicle (1:1 [v/v] solution of ethanol:cremephor EL) and paclitaxel stock (dissolved in 1:1 v/v solution of ethanol: cremephor EL) were diluted 1:6, prior to injection into animals, with sterile 0.1 M Phosphate Buffered Saline (PBS). Tumor cells and bone marrow cells were removed using techniques well known in the art and as described, supra.

Figure 11:
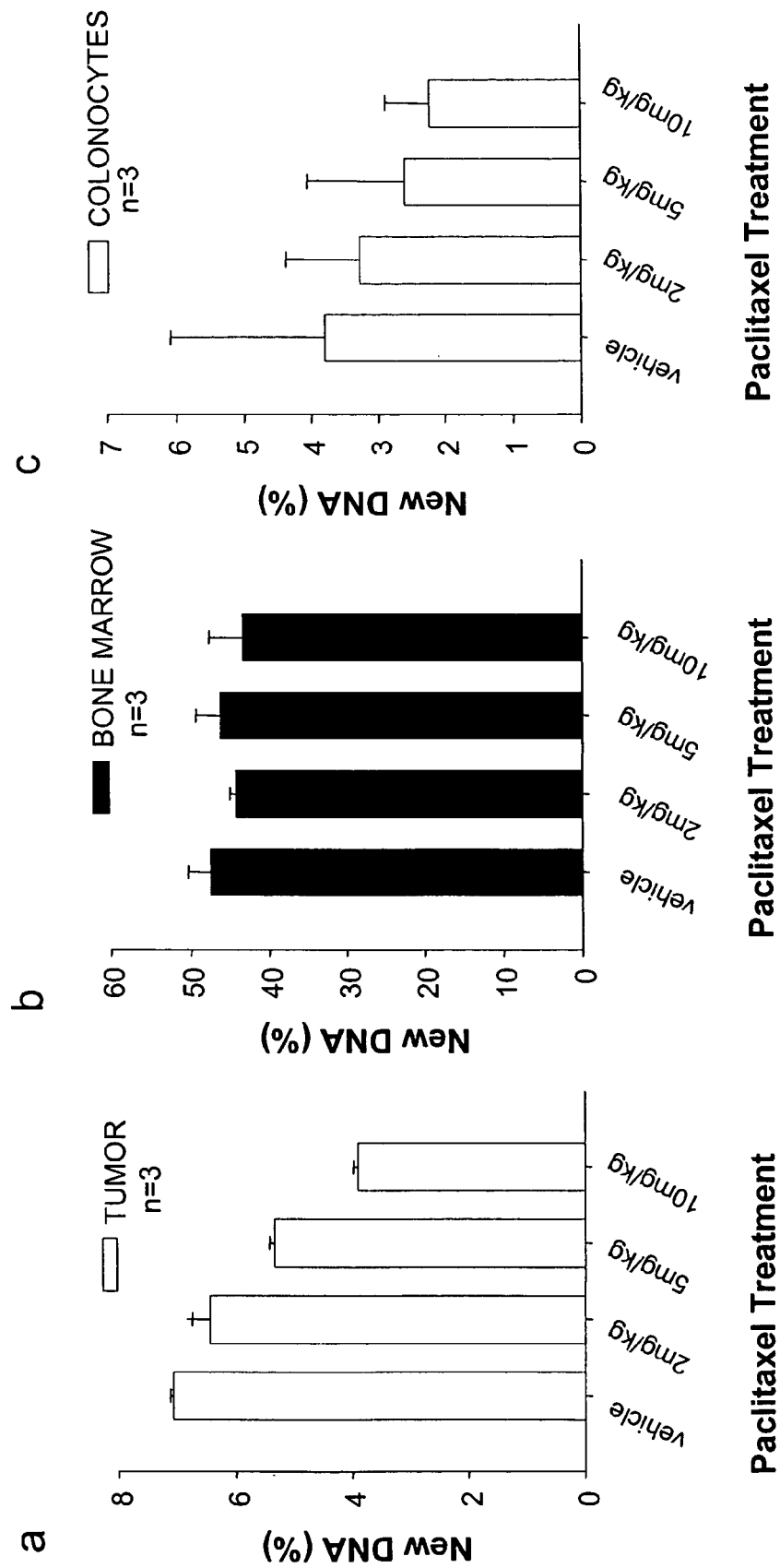
FIG. 11 depicts the in vivo inhibition of cell proliferation, relative to vehicle controls, of increasing doses of paclitaxel, an inhibitor of microtubule disassembly, on three cell types within nude mice. Panel a) depicts transplanted SW1573 human lung cancer cells, panel b) depicts mouse bone marrow cells, and panel c) depicts mouse colon cells (colonocytes). All three cell types were measured concurrently. As FIG. 11 shows, tumor cell and colonocyte proliferation were inhibited, in a dose-dependent manner, by paclitaxel whereas bone marrow cell proliferation was not.

Colonocytes were removed as follows: The colon was removed from animals and washed with 0.1 M Phosphate Buffered Saline (PBS), cut open, and incubated in PBS containing collagenase type2 (72 mg/mL) and DNase (10 µg/mL) at 37° C., gently shaken for 40 minutes. After incubation, tissue was gently scraped and cells were collected by centrifugation at 800×g for 5 minutes at 4° C. The pellet was homogenously suspended in 45% percoll in 1.6% JMEM medium. The suspension was applied on top of a 5 mL cushion of 45% (v/v) percoll in a 75% percoll gradient and centrifuged at 350×g for 30 minutes at room temperature. Colonocytes were collected and washed twice with PBS. Debris was then separated from the cell suspension using a 35 mm filter. De novo DNA synthesis from all three cell types was measured concurrently (i.e., simultaneously) using the methods of the present invention as described, supra. FIG. 11 depicts the results. As shown, paclitaxel exerted an inhibitory effect, in a dose-dependent manner, on tumor cells and colonocytes, but had little or no effect on bone marrow cells.

Example 15

Comparing Angiogenesis and Tissue Cell Proliferation in Different Tissues

The methods of the present invention when applied to angiogenesis are applicable to both animal studies and human clinical trials. The methods provide a faster and more accurate technique for evaluating the activity of potential pro-/anti-angiogenesis drugs and their real efficacy in both early drug discovery and more advanced clinical treatment settings.

The rate of angiogenesis in a tissue is measured by the endothelial cell proliferation rate. Endothelial cell proliferation was quantified by use of the heavy water ($^2H_2O$) labeling technique. Various tissues (as indicated) were digested with collagenase (1 mg/mL) into a single cell suspension. Endothelial cells were enriched by Percoll gradient centrifugation, followed by FACS (sorting on isolectin and CD31 positive cells).

Figure 14:
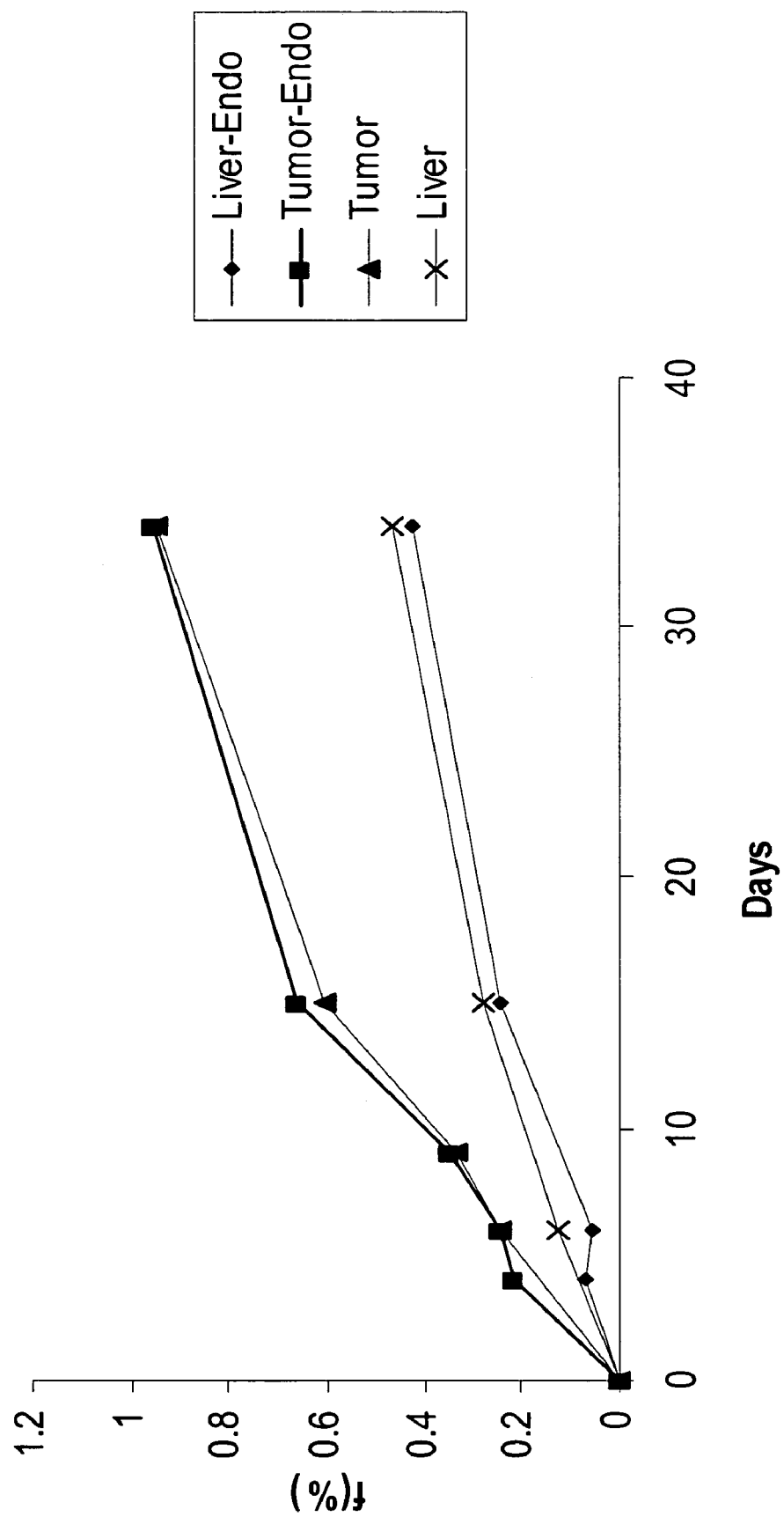
FIG. 14 depicts tumor endothelial cell proliferation, liver endothelial cell proliferation, tumor cell proliferation, and total liver cell proliferation. Measurements were conducted simultaneously. See Example 15, infra for details.

More specifically, the kinetics of angiogenesis was measured in liver and tumor xenografts. Balb/Nu mice were transplanted with human breast tumor cells. After labeling with $^2H_2O$, individual animals were sacrificed, and both tumor tissue and liver tissue were harvested from the same animal. The proliferation rates of tumor cells and tumor endothelial cells (i.e., de novo DNA synthesis) as well as liver cells and liver endothelial cells were measured concurrently (i.e., simultaneously) using the methods of the present invention as described, supra. FIG. 14 depicts the results. In FIG. 14, the proliferation rate of tumor endothelial cells is shown to be significantly higher than the rate of proliferation of liver endothelial cells. Similarly, the rate of proliferation of tumor cells was greater than the rate for liver cells (FIG. 14). The skilled artisan will realize that this technique can be used to identify angiogenesis inhibitors (i.e., anti-angiogenic compounds). For example, if one or more compounds were directly administered to the tumor xenografts of Balb/Nu mice, then the methods of the present invention would detect an inhibition of tumor endothelial cell proliferation relative to liver endothelial cell proliferation and, potentially a reduction in tumor cell proliferation relative to liver cell proliferation (if angiogenesis is limiting for tumor cell growth). Alternatively, if the one or more compounds having anti-angiogenic activity were administered systemically, then rates of tumor endothelial cell proliferation and liver endothelial cell proliferation would both change (i.e., would decrease) such that the ratio might remain unchanged. The ratio of rates of tumor cell proliferation and liver cell proliferation might then either change or not change, as determined by their relative dependence on angiogenesis for growth.

Example 16

Comparing Liver Cell Proliferation (DNA Synthesis) and Liver Fibrogenesis (Collagen Synthesis)

Drug induced liver disease is an important cause of liver failure and is the single most common cause of drug withdrawal from the market. Necrosis is a hallmark feature of hepatocellular injury regardless of the toxic mechanism. Apoptosis is also emerging as an important element in drug induced liver disease. The hepatic response to both necrosis and apoptosis is cell proliferation, replacing the lost cell mass. At low levels of toxic injury, cell proliferation may be sufficient to maintain normal histologic appearance and liver cell pool size, thereby compensating for toxic damage and preventing detection by standard histological methods. Only when the damage exceeds the liver's ability to repair itself do conventional features of liver toxicity become apparent (e.g., elevated LFT's, necrosis, fibrosis etc.).

Figure 15:
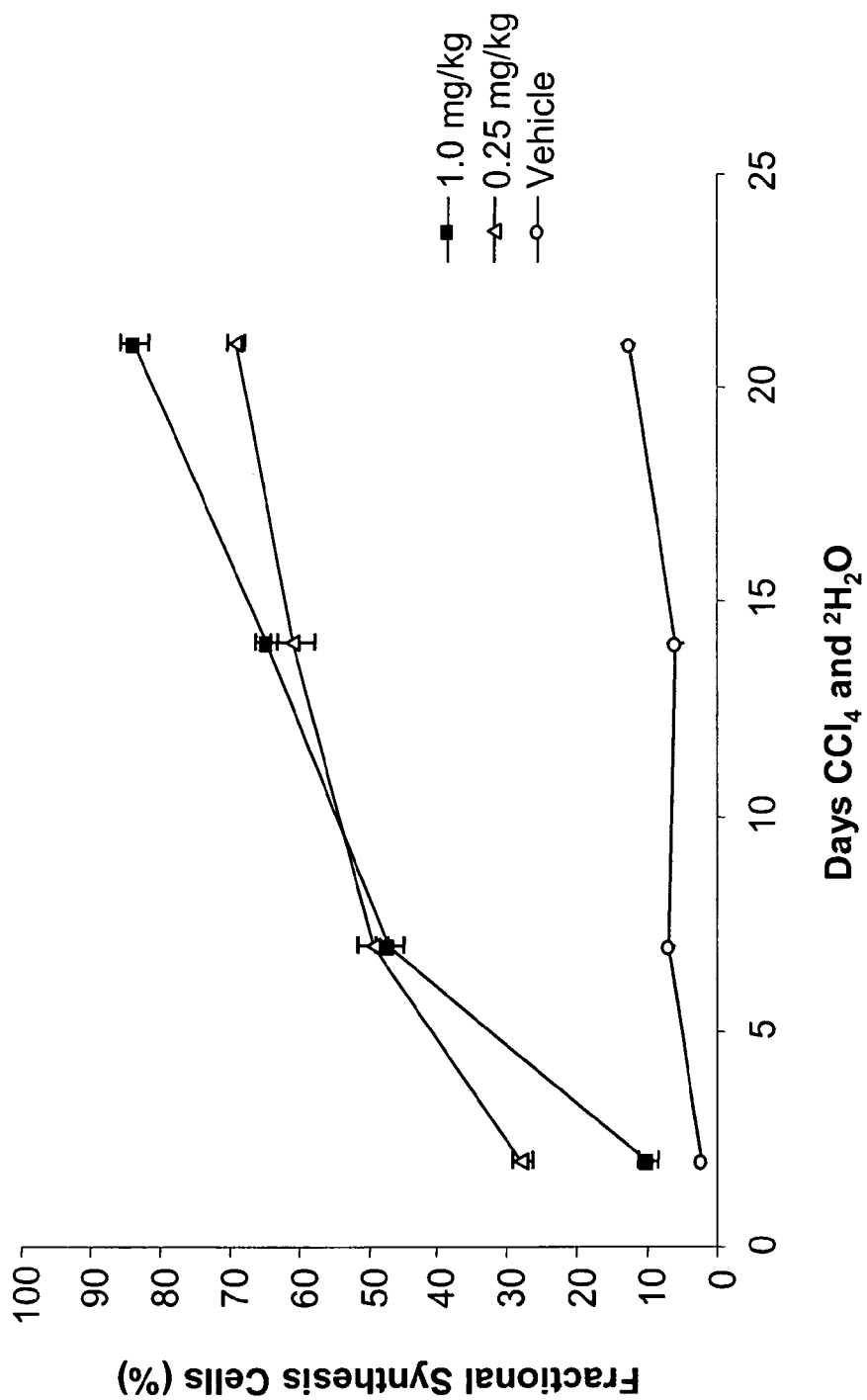
FIG. 15 depicts C57B/6 total liver cell proliferation in response to two doses of carbon tetrachloride ($CCl_4$) and to vehicle control. As FIG. 15 shows, both doses of $CCl_4$ increased total liver cell proliferation relative to vehicle control. Total liver cell proliferation was measured simultaneously with liver collagen synthesis as depicted in FIG. 16, infra.

SVJ mice were injected 2× weekly with 1.0 mL/kg or 0.25 mL/kg of $CCl_4$ or vehicle for up to 4 weeks Cell proliferation was measured at 2, 7, 14, 21 and 28 days of $^2H_2O$ administration and $CCl_4$ treatment using the methods of the present invention as described, supra. $CCl_4$ significantly increased cell proliferation at both doses (FIG. 15). Close to 100% new cells were demonstrated to be present after 4 weeks of repeated $CCl_4$ dosing.

Liver collagen synthesis was measured concurrently (i.e., simultaneously) with de novo DNA synthesis in the same $CCl_4$-treated SJV mice. Collagen was purified from 10 mg of fresh total liver homogenate as follows: using a Polytron homogenizer, collagen was isolated from soft tissue by homogenizing in 0.5 mL 100 mM NaOH. Under these conditions, collagen remains insoluble while most other proteins are readily dissolved. After centrifugation at 7,000×g for 10 minutes at 4° C., the supernatant was discarded. The pellet was washed briefly with 2 mL $H_2O$ and solubilized in reducing Laemmli sample buffer (Bio-Rad, Hercules, Calif.) after boiling for 3 minutes. The dissolved material was size-fractionated by SDS-PAGE. Using standard techniques, proteins were subsequently transferred onto PVDF, and a collagen band corresponding to the alpha monomer of collagen was excised from the resulting membrane after staining the membrane with Coomassie blue.

Acetone precipitated total liver protein and PVDF-bound collagen were hydrolyzed by treating with 6 N HCl, 16 hours at 110° C. Hydrolysates were dried and the N, O-penatflurobenzyl derivative was generated by addition of PFBBr (Pierce) at 100° C. for 1 hour. The hydroxyl group of hydroxyproline was further derivatized with methyl imidizole/acetic anhydride. Hydroxyproline was analyzed on a DB225 GC column, starting temp 100° C. increasing 10° C./min to 220° C. with selected ion monitoring of m/z 352, 353.

Figure 16:
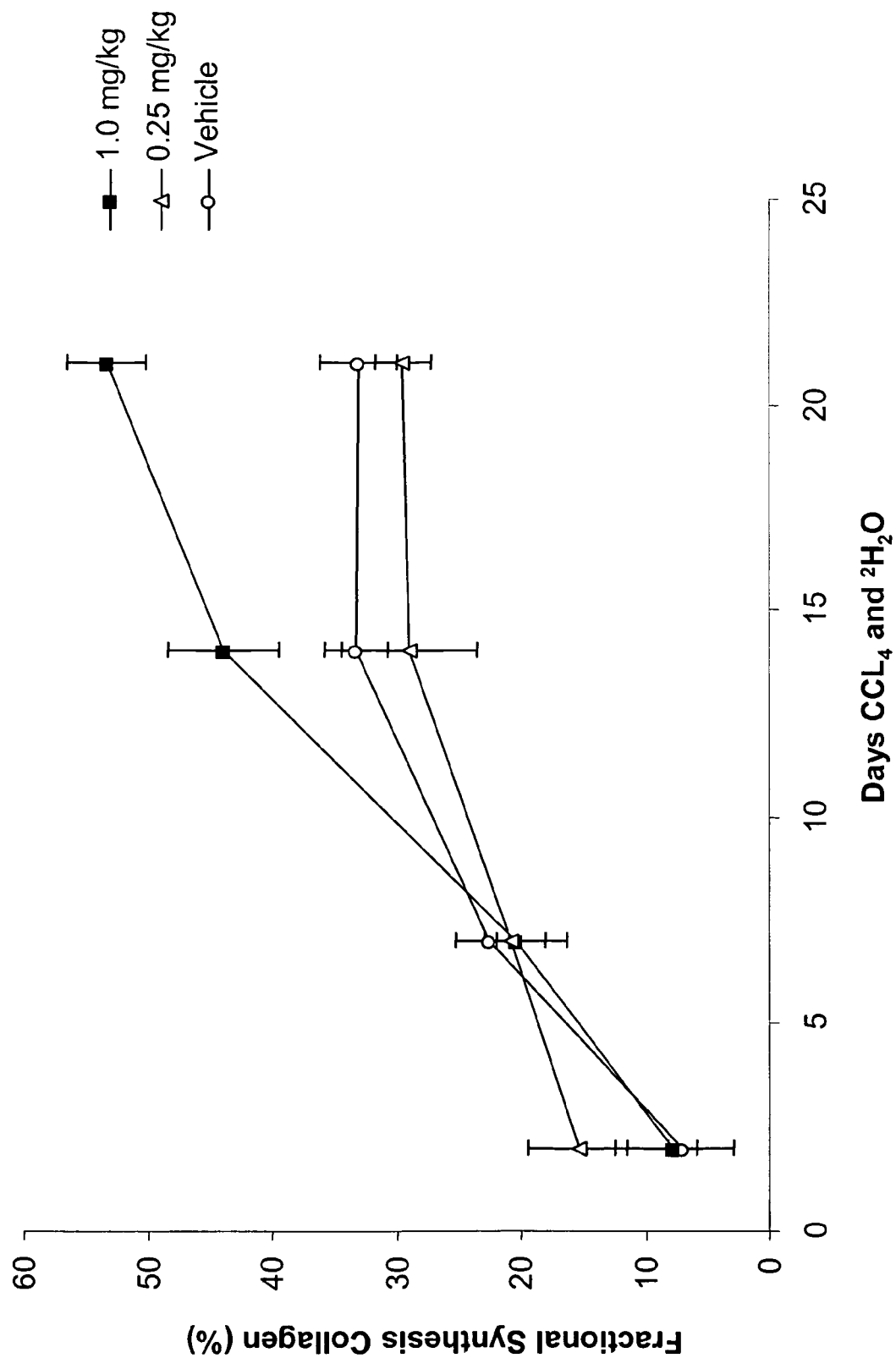
FIG. 16 depicts C57BL/6 liver collagen synthesis in response to two doses of $CCl_4$ and to vehicle control. Measurements were conducted simultaneously with total liver cell proliferation as depicted in FIG. 15, supra.

Hydroxyproline is a molecule of interest and is measured as OH-proline, the molecule being essentially unique to collagen. Because of this fact, total liver protein hydrolysate can be derivatized and the $^2H$ enrichment of hydroxyproline determined by GC/MS as described, supra. Fractional synthesis of collagen in normal and $CCl_4$-treated animals was calculated from $^2H$ incorporation into hydroxyproline from total liver protein using the methods of the present invention as described, supra. FIG. 16 depicts the results. Taking FIGS. 15 and 16 together, the methods were able to show that significant cell proliferation occurred at both doses of $CCl_4$, whereas significant collagen synthesis occurred only at the highest dose of $CCl_4$ thereby providing a sensitive technique able to distinguish between two biomarkers of liver toxicity.

Figure 17:
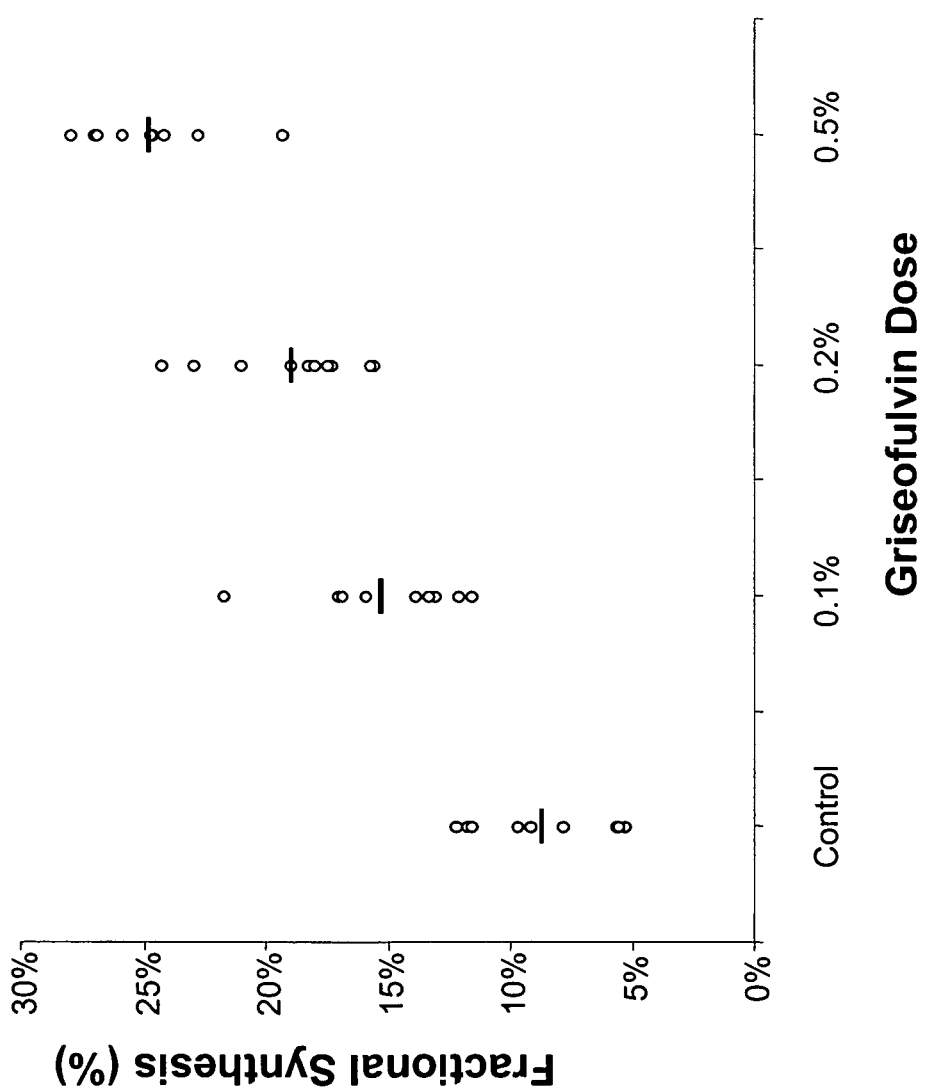
FIG. 17 depicts C57BL/6 mouse liver cell proliferation after griseofulvin administration (0.1, 0.2 and 0.5% 5 days) $p<0.05$ for all groups.

Cell proliferation and collagen synthesis (turnover) were also assessed concurrently (i.e., simultaneously) in mice (C57BL/6 and Balb/c) fed griseofulvin. Griseofulvin is recognized as a hepatotoxin, inducing cell proliferation and porphyria. Mice were administered griseofulvin in their chow (1% w/w) for 5 days. After 5 days of treatment cell proliferation (measured as described, supra) in C57BL/6 mice showed increased proliferation relative to controls (FIG. 17). Specifically, administration of griseofulvin at levels below the no observable effect level (NOEL) showed pronounced effects and dose responsiveness after 5 days (FIG. 17). Collagen turnover was also measured as described, supra, and no increase in collagen turnover was detected at the doses of griseofulvin given to the C57BL/6 mice (data not shown).

Example 17

Comparing Aβ Synthesis or other Brain Proteins to Neuronal Cell Proliferation, Microglial Cell Proliferation, and/or Myelin Synthesis Alzheimer's disease (AD) is thought to involve many factors including various brain proteins such as amyloid-beta (Aβ) protein, amyloid precursor protein (APP), and the C-terminal fragment of APP. In addition, it is thought that other factors, such as changes in neuron proliferation, neuroinflammation, and myelin kinetics is also involved. The methods of the present invention allow for the concurrent (i.e., simultaneous) measurement of all of these components or a fraction of the components thereof to, for example, evaluate whether a compound has therapeutic efficacy in a mouse model of AD, neuroinflammation not associated with AD, neurotoxicity, or other neurodegenerative diseases or conditions.

Isolating and Measuring Brain Proteins

Mice are sacrificed and brain tissue is extracted and APP and CTF are obtained. Secreted APP is extracted from mouse cerebral spinal fluid (CSF) or brain. Proteins are extracted in neutral buffer, insoluble material is removed, and proteins precipitated. Resulting material is exchanged into an ion exchange buffer, and purified by ion exchange chromatography and then size exclusion and/or reversed phase chromatography. The identity of purified protein is confirmed by ELISA and western blot.

Enrichments for Ab, APP, and CTF are performed as described, supra. Molecular flux rates for Ab, APP, and CTF are calculated as described, supra.

Isolation of Hippocampal Neurons and Tetanus Toxin Staining for Measuring Neuronal Cell Proliferation Remove Papain vial from fridge. Add 3 mL HibernateA (BrainBits, LLC, Springfield, Ill.) and place in 37° C. shaker. Remove DNAse aliquot from −20° freezer and allow to thaw in ice. Euthanize mouse using $CO_2$, withdraw blood by cardiac puncture, centrifuge blood at 3000 rpm for 10 min and remove plasma. Remove brain, wash in 5 mL HibernateA and dissect out hippocampus, cut into 0.5 mm slices and transfer to 2 ml HibernateA in trypsinizing flask. Add 3 mL Papain solution and 200 µL of DNAse to trypsinizing flask. Digest at 37° C. for 30 min. Transfer to 15 mL conical tube, centrifuge at 1500×g for 3 min, and remove supernatant. Add 2 mL HibernateA, start timer for 3 min, and triturate 10× over 1 min using a barely fire-polished siliconized Pasteur pipet. Allow to settle for 2 min and transfer the supernatant to another 15 mL conical tube Repeat above step twice to obtain 6 ml cell suspension Centrifuge at 1500×g for 3 min and remove supernatant. Resuspend in 10 mL cell dissociation buffer. Incubate for 5 min. Centrifuge at 1500×g for 3 min and remove supernatant.

Resuspend in 5 ml of 4% paraformaldehyde solution. Incubate at RT for 1 hour. Add 5 mL HibernateA and centrifuge at 1500×g for 3 min and remove supernatant. Wash 1× with 5 mL HibernateA and centrifuge at 1500×g for 3 min and remove supernatant.

Resuspend in 550 µl HibernateA. Remove 50 µL for negative control. Add 5 µL rTTC to 500 µL cell suspension (1:100 dilution).

Incubate at RT for 1 hour. Wash 2× with 5 mL HibernateA, centrifuge at 1500×g for 3 min, and remove supernatant. Resuspend in 200 µL HibernateA.

Add 2.5 ul anti-TTC antibody to the stained sample, incubate for 30–45 min at RT. Wash 2× with 5 mL HibernateA by centrifuging at 1500×g for 3 min and remove supernatant. Resuspend in 500 µl HibernateA.

Dilute 5 µL goat-anti-mouse-ALEXA 488 to 50 µl in HibernateA (1:10 dilution). Add 5 µL diluted antibody to stained sample and 0.5 µL to the negative control. Incubate at RT for 15–30 min.

Wash 2× with 5 mL HibernateA by centrifuging at 1500×g for 3 min and remove supernatant. Resuspend stained sample in 1 mL and negative control in 250 µl HibernateA. Add 1:500 PI to sample and sort.

DNA synthesis is measured as described, supra.

Isolating Microglia for the Measurement of Neuroinflammation in Alzheimer's Disease and Other Neural Diseases (Such as Neural Inflammation not Associated with Alzheimer's Disease)

Mice are labeled with $^2H_2O$ for an appropriate period. Mice are anesthetized and perfused with 10 mLs ice cold PBS (trans-cardiac perfusion). Brains are immediately harvested and placed on ice in cold PBS. Brains are then minced and shaken for 25 minutes at 37° C. in baffle flasks containing 30 mLs of PBS supplemented with 0.05% DNAse, 0.25% trypsin, 0.8% glucose, and 0.16% EDTA. Subsequently, each flask is neutralized with 30 mLs of ice cold media (1:1 DMEM:HAM's F10 supplemented with 10% FBS), and placed on ice. Tissue is then triturated repeatedly with a 10 mL pipette until all tissue fragments are dissociated. The resulting material is then filtered through a 100 micrometer filter, washed in media, and run on a discontinuous percoll gradient in order to remove non-cellular debris.

The resulting cells are stained with the macrophage specific markers F4/80 and CD11b, fixed in 4% paraformaldehyde (PFA), and then isolated by FACS. Alternatively, cells can be labeled with other cell surface or intracellular markers that can be used to sort microglia or microglial subsets by FACS or MACS. Cells can also be sorted immediately rather than fixing them in 4% PFA. The technique can also be used to isolate infiltrating leukocytes that enter the brain from the circulatory system.

DNA synthesis is measured as described, supra.

Isolating and Measuring Myelin

A set of 2-mL microcentrifuge tubes are weighed. Brains are collected from the mice and put it into the pre-weighed microcentrifuge tubes. The microcentrifuge tubes are weighed again. The net weight is the brain weight. The brain is put onto an ice-cooled glass plate, and 10 crystals of BHT are added. A razor blade is used to mince the brain for 1 minute. A spatula is used to put the minced brain back into the microcentrifuge tubes. The brain is minced well with a spatula. A portion of the minced brain is put into 13×100 mm glass tubes with PTFE screw caps ensuring the tissue is at the bottom of the tube. The rest of the brain is stored in the microcentrifuge tubes at −20° C. 2 mL of chloroform-methanol 2:1 (v/v) with BHT is added into the glass tubes and the tubes are vortexed ensuring that all of the tissues are soaked in the solvent. Let stand 3 h at room temperature in a dark area. The caps are taken off the glass tubes. The tubes are centrifuged at 2000 RCF for 10 minutes at room temperature. The supernatant (lipid extracts) is poured into 2-mL screw capped vials and the solid residue is discarded.

100 mL of developing solvent (chloroform-methanol-water: 69.15%:26.60%:4.26%) is added into the TLC separation tanks 1 h before adding the TLC plates. A 20 mL pipette is used to spot 20 mL of total cerebroside standard on lanes 1, 10, 19 of Whatman LK6DF silica gel 60 TLC plates. For each sample, a 20 mL pipette is used to spot 100 µL of lipid extracts on two neighboring lanes (50 mL/lane). Wait until TLC plates look visually dry. The TLC plates are developed in the developing tanks. Each tank holds two plates, facing each other. Normally it takes 40–45 minutes for the plates to be fully developed. After TLC plates develop, wait 15 minutes for the plates to dry. 20 iodine crystals are put into a tank specially used for iodine vapor. The tank is put on a heatblock set at 80° C. The dried TLC plates are put in the iodine tank to visualize the spots of lipids containing double bonds. The spots of total cerebroside standard are matched with those of samples. The TLC plate images are scanned by a computer. The silica gel is collected onto a weighing box and transfered to a 12×75 mm disposable glass tube. 1 mL of chloroform-methanol 2:1 is added with BHT and vortexed. Let stand until silica settles. The solvent is poured into a 13×100 mm screw cap tube. The solid residue is discarded. 1 mL of 3 N methanolic HCl is added into the tube and the tube is capped tightly. The tubes are put on a heatblock at 80° C. for 2 h. The tubes are then removed from the heating block and allowed to cool to room temperature. 1.5 mL H2O and 3 mL hexane are added into the tubes and the tubes are vortexed. 1.8–2 mL of the bottom layer (methyl glucose and methyl galactose) are transferred to GC vials. The GC vials are put into a fitted rotor of the Jouan 10.10 speedvac and the rotor is balanced and set at 60° C. Vacuum until the tubes are dry. 100 µL of acetic anhydride-pyridine 2:1 (v/v) is added to the GC vials and the vials are covered and allowed to stand for 1 h at room temperature. The vials are then blown down under N2 until dry. 100 µL ethyl acetate is added and the vials are vortexed. The mixture is transferred to GC inserts and the vials are capped with a cramper. The samples are run on the GC/MS and galactocerebroside enrichments are determined as described, supra.

All publications, patents, and patent applications cited herein are hereby incorporated by reference in their entirety for all purposes to the same extent as if each individual publication, patent, or patent application were specifically and individually indicated to be so incorporated by reference. Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit and scope of the appended claims.

I claim:

1. A method of analyzing the relative molecular flux rates of two or more biological molecules of different biochemical classes in one or more tissues or individuals, comprising:
    (a) administering isotope-labeled water to one or more tissues or individuals for a period of time sufficient for an isotope label of said isotope-labeled water to be incorporated in vivo into two or more biological molecules to form two or more isotope-labeled biological molecules;
    (b) obtaining one or more biological samples from said one or more tissues or individuals, wherein said one or more biological samples together comprise said two or more isotope-labeled biological molecules;
    (c) measuring a content, rate of incorporation and/or pattern or rate of change in content and/or pattern of isotope labeling of said two or more biological molecules to determine molecular flux rates of said two or more biological molecules; and
    (d) comparing the molecular flux rates of said two or more biological molecules to analyze the relative molecular flux rates of said two or more biological molecules;
wherein said two or more biological molecules are independently selected from the group consisting of lipids, carbohydrates, proteins, peptides, amino acids, and nucleic acids; and
wherein said isotope-labeled water is $^2H_2O$ or $H_2^{18}O$.

2. The method of claim 1 wherein said isotope labeled water is $^2H_2O$.

3. The method of claim 1 wherein said isotope labeled water is administered orally, parenterally, subcutaneously, intravascularly, or intraperitoneally.

4. The method of claim 3 wherein said isotope labeled water is administered orally.

5. The method of claim 1 wherein said one or more individuals are humans.

6. The method of claim 1 comprising the additional step of discontinuing said administering step (a) prior to performing steps (b), (c) and (d).

7. The method of claim 1 wherein said isotope-labeled water is administered in a single dose.

8. The method of claim 1 wherein said administering of said labeled water is selected from the group consisting of continuously administering, intermittently administering, administering in a single dose and administering in multiple doses.

9. The method of claim 1 wherein said biological sample is obtained pre-mortem.

10. The method of claim 9 wherein said biological sample is obtained by blood draw, urine collection, or biopsy.

11. The method of claim 1 wherein more than one biological sample is obtained from said individual.

12. The method of claim 1 wherein said biological sample is obtained post-mortem.

13. The method of claim 1 wherein said measuring step (c) includes calculating the isotope enrichments of said two or more biological molecules by mass isotopomer distribution analysis (MIDA) and applying precursor-product or exponential decay equations to determine the molecular flux rates of said two or more biological molecules.

14. The method of claim 1 wherein said comparing step (d) comprises measuring a ratio or graphical relationship of said molecular flux rates.

15. The method of claim 1 wherein step (c) comprises detecting said two or more biological molecules by NMR or mass spectrometry.

16. The method of claim 15 wherein step (c) comprises detecting said two or more biological molecules by mass spectrometry.

17. The method of claim 1 further comprising the additional step of purifying said biological molecules prior to measuring step (c).

18. The method of claim 1 further comprising the additional step of isolating said biological molecules prior to measuring step (c).

19. The method of claim 1 further comprising the additional step of hydrolyzing or otherwise degrading said biological molecules prior to measuring step (c) to form one or more smaller molecules.

20. The method of claim 1 further comprising the additional step of chemically modifying or derivatizing said biological molecules prior to measuring step (c).

21. The method of claim 1 wherein said two or more biological molecules comprises a first biological molecule and a second biological molecule and said first biological molecule is DNA and said second biological molecule is a protein.

22. The method of claim 21 wherein said biological sample is selected from the group consisting of muscle, liver, adrenal tissue, prostate tissue, colon tissue, endometrial tissue, skin, breast tissue, adipose tissue, colon, lymphoid tissue, and brain.

23. The method of claim 21 wherein said DNA and said protein are measured simultaneously.

24. The method of claim 21 wherein said biological sample comprises tumor cells.

25. The method of claim 21 wherein said biological sample comprises bacteria.

26. The method of claim 21 wherein said protein is a cellular protein and said DNA is mitochondrial DNA.

27. The method of claim 21 wherein said protein is a cellular protein and said DNA is genomic DNA.

28. The method of claim 21 wherein said first biological molecule is adipose tissue acyl-glyceride and said second biological molecule is either protein or DNA.

29. The method of claim 28 further including a third biological molecule wherein said second biological molecule is a protein and said third biological molecule is DNA.

30. The method of claim 1 wherein said one or more biological samples are obtained from somatic tissue.

31. The method of claim 30 wherein said somatic tissue is selected from the group consisting of muscle, liver, adrenal tissue, prostate tissue, colon tissue, endometrial tissue, skin, adipose tissue, breast tissue, colon, lymphoid tissue, and brain.

32. The method of claim 21 wherein said first biological molecule is lung collagen and said second biological molecule is lung fibroblast DNA.

33. The method of claim 21 wherein said first biological molecule is a protein and said second biological molecule is mRNA.

34. The method of claim 1 wherein said first biological molecule is mRNA and said second biological molecule is DNA.

35. The method of claim 1 wherein the two or more biological molecules are selected from the group consisting of apolipoprotein B, triglycerides, phospholipids, cholesterol, and cholesterol ester.

36. The method of claim 35 wherein said one or more biological samples are liver tissue and/or blood.

37. The method of claim 21 wherein said first biological molecule is a glycerol moiety of triglyceride and said second biological molecule is a fatty acid moiety of triglyceride.

38. The method of claim 21 wherein said first biological molecule is mitochondrial cardiolipin and said second biological molecule is mitochondrial DNA.

39. The method of claim 21 wherein said first biological molecule is B Iymphocyte DNA and said second biological molecule is plasma immunoglobulin.

40. The method of claim 21 wherein said first biological molecule is dermal collagen and said second biological molecule is dermal elastin.

41. The method of claim 21 wherein said first biological molecule is skin keratin and said second biological molecule is keratinocyte DNA.

* * * * *

UNITED STATES PATENT AND TRADEMARK OFFICE
CERTIFICATE OF CORRECTION

PATENT NO. : 7,262,020 B2
APPLICATION NO. : 10/872280
DATED : August 28, 2007
INVENTOR(S) : Marc K. Hellerstein Page 1 of 1

It is certified that error appears in the above-identified patent and that said Letters Patent is hereby corrected as shown below:

Col. 53 in Claim 2, line 66, please delete "isotope labeled" and replace with hyphenated --isotope-labeled--;

Col. 54 in Claim 3, line 1, please delete "isotope labeled" and replace with hyphenated --isotope-labeled--;

Col. 54 in Claim 4, line 4, please delete "isotope labeled" and replace with hyphenated --isotope-labeled--;

Col. 54 in Claim 21, line 57, please delete "comprises" and replace with --comprise--; and Col. 56 in Claim 39, line 18, please delete "B lymphocyte" and replace with --B lymphocyte--.

Signed and Sealed this

Fourteenth Day of October, 2008

JON W. DUDAS
*Director of the United States Patent and Trademark Office*